United States Patent
Melton et al.

(10) Patent No.: US 10,941,384 B2
(45) Date of Patent: Mar. 9, 2021

(54) COMPOSITIONS AND METHODS FOR PROMOTING THE GENERATION OF ENDOCRINE CELLS

(71) Applicant: President and Fellows of Harvard College, Cambridge, MA (US)

(72) Inventors: Douglas A. Melton, Lexington, MA (US); Sinisa Hrvatin, Cambridge, MA (US); Shuibing C. Chen, Arlington, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 896 days.

(21) Appl. No.: 14/777,480

(22) PCT Filed: Mar. 17, 2014

(86) PCT No.: PCT/US2014/030421
§ 371 (c)(1),
(2) Date: Sep. 15, 2015

(87) PCT Pub. No.: WO2014/145625
PCT Pub. Date: Sep. 18, 2014

(65) Prior Publication Data
US 2016/0032249 A1    Feb. 4, 2016

Related U.S. Application Data

(60) Provisional application No. 61/800,931, filed on Mar. 15, 2013.

(51) Int. Cl.
*C12N 5/071*    (2010.01)
*A61K 31/122*   (2006.01)
(Continued)

(52) U.S. Cl.
CPC .......... *C12N 5/0676* (2013.01); *A61K 31/122* (2013.01); *A61K 31/404* (2013.01);
(Continued)

(58) Field of Classification Search
None
See application file for complete search history.

(56) References Cited

U.S. PATENT DOCUMENTS

| 8,728,812 B2 | 5/2014 | Chen et al. |
| 9,157,062 B2 | 10/2015 | Chen et al. |
| 2011/0070645 A1 | 3/2011 | Chen et al. |

FOREIGN PATENT DOCUMENTS

WO    WO 2009/132083    10/2009

OTHER PUBLICATIONS

Stukenbrock, Hendrik; et al; "9-Cyano-1-azapaullone (Cazpaullone), a Glycogen Synthase Kinase-3 (GSK-3) Inhibitor Activating Pancreatic [beta]-Cell Protection and Replication" Journal of Medicinal Chemistry, 51, 2196-2207, 2008 (Year: 2008).*
(Continued)

*Primary Examiner* — David W Berke-Schlessel
(74) *Attorney, Agent, or Firm* — Morse, Barnes-Brown & Pendleton, P.C.; Lisa M. Warren, Esq.

(57) ABSTRACT

Disclosed herein are compositions and methods for the generation of insulin positive β cells, for example by exposing Pdx+ pancreatic progenitor cells to one or more compounds, and compositions and kits comprising isolated populations of insulin positive cells.

15 Claims, 7 Drawing Sheets

(51) Int. Cl.
| | |
|---|---|
| *A61K 35/39* | (2015.01) |
| *A61K 31/4178* | (2006.01) |
| *A61K 45/06* | (2006.01) |
| *A61K 31/404* | (2006.01) |
| *A61K 31/4439* | (2006.01) |
| *A61K 31/4045* | (2006.01) |

(52) U.S. Cl.
CPC ...... *A61K 31/4045* (2013.01); *A61K 31/4178* (2013.01); *A61K 31/4439* (2013.01); *A61K 35/39* (2013.01); *A61K 45/06* (2013.01); *C12N 5/0678* (2013.01); *C12N 2501/727* (2013.01); *C12N 2501/999* (2013.01)

(56) References Cited

OTHER PUBLICATIONS

Hrvatin, Exploring the Use of Human Pluripotent Stem Cells to Create Functional Pancreatic Beta-cells, Ph.D. Thesis submitted to Harvard University, Dec. 2012. pp. 1-167. p. 8, figure 1-1; p. 29, Abstract; p. 34, Figure 2-1; p. 38, Figure 2-4; p. 40, para 2; p. 41, para 2,Figure 2-6; p. 43, para 1; p. 45, para 1 to p. 47, para 2; p. 48, para 2-3; p. 51, Figure 2-8.

International Search Report for International Application PCT/US2014/30421, dated Aug. 20, 2014.

\* cited by examiner

COMPOSITIONS AND METHODS FOR PROMOTING THE GENERATION OF ENDOCRINE CELLS

RELATED APPLICATIONS

This application is a national stage filing under 35 U.S.C. 371 of International Application No. PCT/US2014/030421, filed Mar. 17, 2014, which claims the benefit of U.S. Provisional Application No. 61/800,931, filed Mar. 15, 2013. The entire teachings of the above applications are incorporated herein by reference. International Application PCT/US2014/030421 was published under PCT Article 21(2) in English.

FIELD OF THE INVENTION

Certain embodiments disclosed herein relate generally to insulin-producing cells. More particularly, certain examples disclosed herein relate to endocrine cells and insulin-producing cells that are produced by exposure of pancreatic cells or pancreatic precursors to a PKC inhibitor.

BACKGROUND OF THE INVENTION

Type I diabetes results from the destruction of insulin-producing pancreatic beta cells and therefore there are several approaches aimed at cell-based strategies to replace these cells, and rejuvenate the pancreas. The spontaneous or undirected differentiation of ES cells produces very small numbers of insulin-producing cells, barely enough for research study and far short of the numbers needed for therapeutic application.

Human embryonic stem cells (hESCs) and induced pluripotent stem cells (iPSCs) represent a potentially unlimited starting material for the generation of functional pancreatic cells for transplantation therapy and disease modeling of diabetes. Essential in this pursuit is an efficient method for the differentiation of hESCs/iPSCs down the pancreatic lineage to produce endocrine cells. By mimicking known signals used during embryonic pancreatic development in vivo, efficient stepwise protocols have been developed to differentiate hESCs first into definitive endoderm and then into pancreatic progenitors (FIG. 1A)[1-9]. However, the signals needed to produce endocrine progenitors from pancreatic progenitors, as well as insulin-expressing β cells from the endocrine progenitors, remain poorly defined. Several recent studies demonstrated that blocking TGFβ signaling and BMP signaling can improve the differentiation of pancreatic progenitors into endocrine cells[1,10,11]. However, the overall efficiency of creating insulin-producing cells is still very low. Thus, there is a need to identify the signaling pathway controlling the differentiation of pancreatic progenitors to endocrine cells, and increase the ability and efficiency of the differentiation of pancreatic progenitor cells into endocrine cells and insulin-producing cells for therapeutic use.

SUMMARY OF THE INVENTION

An essential step for therapeutic and research applications of stem cells is the ability to efficiently and reproducibly differentiate them into specific differentiated cell types. A key step of the stepwise differentiation from human embryonic stem cells (ESCs) to glucose-responding β cells is the specification from pancreatic progenitors (PP) (which express Pdx1) toward endocrine cells, also known as endocrine progenitors (EP) which are Ngn3+. Herein, the inventors have performed two independent high-content chemical screens to identify PKC inhibitors as inducers of endocrine cells from pancreatic progenitors. This is suprizing, since the inventors have previously demonstrated that PKC agonists, previously shown to increase the differentiation towards pancreatic progenitors, blocked the differentiation towards pancreatic endocrine cells. Together these results suggest a dynamic role of PKC at different stages during pancreatic development.

Moreover, based on the inventors' previous research using high throughput chemical screening to identify the small molecules that direct hESC differentiation toward definitive endoderm[12] and pancreatic progenitors[13], the inventors utilized the same approach to identify small molecules that could facilitate the further differentiation of pancreatic progenitors towards endocrine cells. To maximize the chance of success, the inventors performed two independent chemical screens that differed in the choice of hESC lines, directed differentiation protocols, chemical libraries and primary screening assays. Both screens identified PKC antagonists (e.g., PKC inhibitors) as inducers of the endocrine pancreatic lineage. Previously, the inventors have demonstrated that PKC agonists, such as indolactam V (ILV), are essential for the differentiation of pancreatic progenitors (Pdx1+ PP cells) from endoderm cells (definitive endoderm, DE cells) which are Sox17+ (see US Patent Application US 2011/0070645, which is incorporated herein in its entirety by reference). The inventors have also previously demonstrated that definitive endoderm (DE) cells can be generated from iPS and ES cells using IDE compounds, as disclosed in US Patent Application US2012/0088300, which is incorporated herein in its entirety by reference. Accordingly, herein the inventors demonstrate a highly dynamic role for PKC during pancreatic development and demonstrate improvements to current directed differentiation protocols that result in the production of up to ten-fold more endocrine cells than previously used methods and protocols. In particular, combining the methods of the present invention with those disclosed in US2012/0088300 and US 2011/0070645, or other methods to differentiate iPS cells and ES cells to pancreatic progenitors, the inventors have demonstrated the last step in the step-wise differentiation of human embryonic stem cells (ESCs) to glucose-responding β cells.

Accordingly, the present invention contributes to a strategy to increase the efficiency of beta cell formation from stem cells, where stem cells, e.g., embryonic stem cells, and derivatives are exposed to factors they would normally encounter in vivo during embryonic development. The starting point for this strategy is differentiating stem cells, e.g., embryonic stem cells, into Sox17+ definitive endoderm (DE) cells, and then converting the DE cells to Pdx1+ pancreatic progenitors (PP), which can be performed by methods as disclosed in US2012/0088300 and US 2011/0070645, or other methods to differentiate iPS cells and ES cells to pancreatic progenitors. The present invention expands on step-wise differentiation, and relates to methods and compositions for the efficient chemically mediated differentiation of pancreatic progenitor cells, such as Pdx1+ pancreatic progenitor cells, or variants thereof into endocrine cells, in particular endocrine progenitor cells that are Ngn3+. In some embodiments, the method comprises contacting a pancreatic progenitor cell with a compound or derivatives, analogues or variants thereof as disclosed herein, to induce the differentiation of the pancreatic progenitor cell to an endocrine progenitor cell, and in some embodiments, a glucose responding β-cell that is insulin positive. Such endocrine progenitors are referred herein as chemically-induced endocrine progenitor cells.

In some embodiments, the method comprises contacting a pancreatic progenitor cell with a PKC inhibitor compound, or a PKC β inhibitor compound, or a derivative, analogue or variant of the compound as follows:

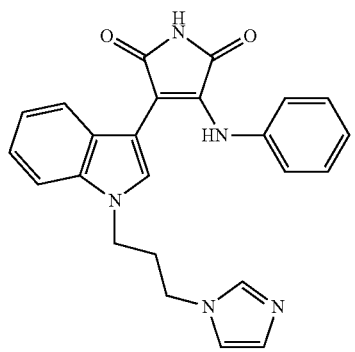 [SMILES: O=C1NC(=O)C(c2cn(CCCn3ccnc3)c3ccccc23)=C1Nc1ccccc1]

In some embodiments, the method comprises contacting a pancreatic progenitor cell with a GSK-2 inhibitor compound or a derivative, analogue or variant of the compound as follows:

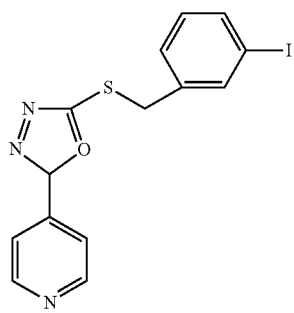

In some embodiments, the method comprises contacting a pancreatic progenitor cell with a bisindolylmaleimide compound, such as for example, but not limited to bisindolylmaleimide I, bisindolylmaleimide II, bisindolylmaleimide III, hydrochloride, or a derivative, analogue or variant of any of the compounds as follows:

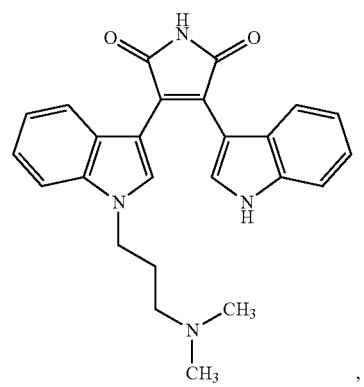

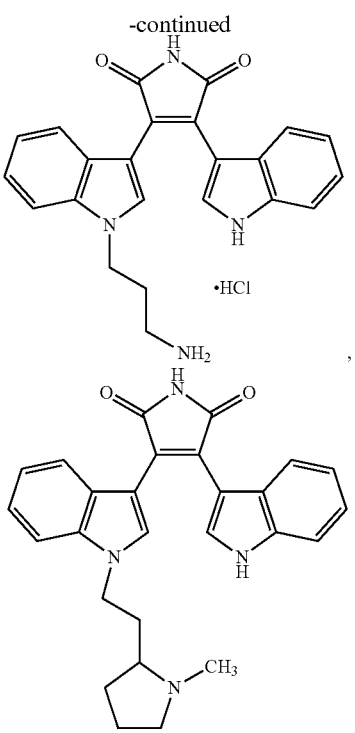

In some embodiments, the method comprises contacting a pancreatic progenitor cell with pseudohypericin or a derivative, analogue or variant of the compound as follows:

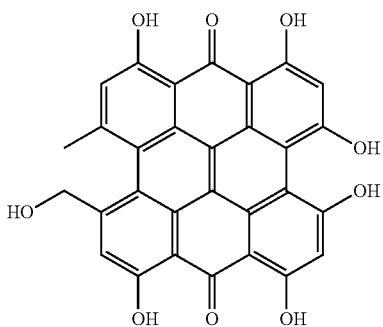 [SMILES: Cc1cc(O)c2c(=O)c3c(O)cc(O)c4c5c(O)cc(O)c6c(=O)c7c(O)cc(CO)c8c1c2c(c34)c(c65)c78]

In some embodiments, the method comprises contacting a pancreatic progenitor cell with a indorublin-3-monoxime, 5-Iodo or a derivative, analogue or variant of the following compound:

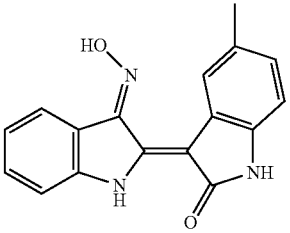 [SMILES: Cc1ccc2c(c1)/C(=C1/Nc3ccccc3/C1=N\O)C(=O)N2]

Another aspect relates to methods and compositions for the efficient differentiation of pancreatic progenitor cells, such as Pdx1+ pancreatic progenitors into endocrine cells, which express Ngn3. In some embodiments, the method comprises contacting a pancreatic progenitor cell with a PKC inhibitor, such as a PKCβ inhibitor as disclosed herein, such as GSK-3 inhibitor, or a bisindolylmaleimide compound as disclosed herein, or any compound of formula (I)-(V) or an analogue or derivative thereof to induce the differentiation of the pancreatic progenitor cells to endocrine progenitor cells which are Ngn3+. In some embodiments, the Ngn3+ endocrine cell can spontaneously differentiate into a glucose-responding β-cell, which expresses insulin.

Accordingly, the present invention provides a chemically mediated step-wise differentiation of preparing pancreatic progenitor cells that are β-cell like from Pdx1+ pancreatic progenitor cells.

The step-wise approach to generate insulin positive β-cell like cells from Pdx1+ pancreatic progenitor cells is intended as a guide, and is not intended to limit the invention except where explicitly indicated.

BRIEF DESCRIPTION OF THE DRAWINGS

Certain illustrative embodiments are described in more detail below with reference to the accompanying figures.

The patent or application file contains at least one drawing executed in color. Copies of this patent or patent application publication with color drawings will be provided by the Office upon request and payment of the necessary fee.

FIG. 1A is a schematic showing the stepwise differentiation from hESCs to pancreatic endocrine cells. DE, definitive endoderm; PP, pancreatic progenitor; EP, endocrine progenitor; EN, endocrine cells. Scheme of high-content screen beginning with a population of cells that have differentiated into pancreatic progenitors. FIGS. 1B and 1F are schematic diagrams showing the method of high-content screen, which begins with a population of cells that have differentiated into pancreatic progenitors. FIGS. 1C and 1G show the chemical structures of a PKCβ inhibotor and Bisindolylmaleimide I compound identified from the screen. FIGS. 1D and 1H show an efficacy curve of the hit compounds. Bisindolylmaleimide I treatment at 6.75 M and 27 M caused considerable auto-fluorescence and toxicity. FIG. 1E shows the effect of PKCβ on different hESC line. The hit compounds effect on HUES 8-pancreatic progenitor population. After 14 d of differentiation, the HUES 8-pancreatic progenitor populations were treated with 10 M PKCβ inhibitor for four days and then stained with NGN 3 antibody (green). NGN3, neurogenin 3. Scale bar is 100 m. FIG. 1I shows the effect of the hit compounds on H1-pancreatic progenitor population Representative images after 6 days of chemical treatment, insulin staining. Percentage of insulin-positive cells with s.d. FIG. 1J shows the effects of PKC inhibitors on H1-derived pancreatic progenitor populations. After 14 d of differentiation, the H1-derived pancreatic progenitor populations were treated with 10 M PKCβ inhibitor for 6 days and then stained with NGN3 antibody. The percentage of NGN3$^+$ cells was analyzed with the Cellomics high content screening system (Thermo Scientific). FIG. 1K shows the number of cells expressing islet after incubation with the PKC inhibitor Bis1. HUES8 pancreatic progenitors were treated with DMSO or Bis1 for 6 days in the presence of Noggin and Alk5 inhibitors. Insulin cell number with was counted over the same area in different wells. Error bars indicate s.d. n=4.

FIG. 2A shows H1 hESC-derived pancreatic progenitors which were treated for 3 days with 3 μM Bis1. Cells were stained with insulin, c-peptide, glucagon, UCN3, PDX1 and NKX6-1 antibodies. All insulin-expressing cells express c-peptide. Few insulin-expressing cells express NKX6-1 or UCN3, markers of mature human β cells. Many insulin-expressing cells co-express another endocrine marker glucagon. Scale bars are 100 μm. FIG. 2B shows the PKCβ inhibitor-treated populations can further differentiate into endocrine cells in vitro. Scheme beginning with cells that have been treated with hit chemicals, e.g., PKC inhibitors, comprises a population containing many NGN3-expressing cells. The HUES 8-derived pancreatic progenitor cells treated with DMSO were used as negative controls. Starting populations were cultured in DMEM+B27 medium for 6 days and stained with c-peptide antibody. CP: c-peptide. The PKCβ inhibitor-treated population differentiates into glucose-responding cells after transplantation under the kidney capsule of SCID-Beige mice. The PKCβ inhibitor-treated populations were collected and implanted into the left kidney of SCID-Beige mice. The DMSO-treated population was used as a negative control. 12 weeks later, the mouse sera collected at fasting condition and at 30 mins after glucose stimulation were analyzed using ELISA to measure human c-peptide expression. Error bars indicate s.d. Scale bars are 100 μm.

FIG. 3A shows number of Insulin positive cells (Ins+) after hESC-derived pancreatic progenitors cells were treated with DMSO, 1 M Bisindolylmaleimide I and 1 M PDBu for 6 days. Wells were stained for insulin and cell number counted in representative portions of the well by the Cellomics high content screening system. Error bars represent s.d. Two-tailed T-test p<0.05. FIG. 3B shows the fold old change of insulin (INS) and glucagon (GCG) transcripts by qRT-PCR of cells after 3 day treatment with 3 M BisI, 5 M TPB (PKC agonist) and Bis1+TPB. Endocrine induction is blocked by PKC agonist TPB and reversed by Bis1. Data displayed as log 2 of the fold change over DMSO. P<0.001. The decrease in INS and GCG expression due to TPB treatment is reversed by BisI. FIG. 3C shows the fold change of insulin (INS) and glucagon (GCG) transcripts by qRT-PCR of cells after 3 day treatment with TPB, Alk5 inhibitor or a combination of both. PKC agonist TPB is sufficient to block the effect of Alk5 inhibitors on endocrine induction. Data displayed as log 2 of the fold change over DMSO. P<0.001. FIG. 3D shows a summary of the model where PKC agonists induce the differentiation towards pancreatic progenitors while PKC antagonists induce the differentiation towards endocrine cells.

FIG. 4A shows the data of the primary screen. Each line represents one compound at one concentration. 2,000 compounds were tested at two concentrations: 10 μM and 1 μM. The x-axis is the 2,000 compounds with two concentrations of each. The y-axis is the number of cells positively stained by the NGN3 antibody. Primary hits (above the red line) were designated as compounds that induced NGN3 in more than 6300 NGN3$^+$ cells/well, which is 3 times higher than the average. Subsequent tests confirmed six compounds that increase both the number and percentage of NGN3$^+$ cells. The compounds were labeled with different colors. The other dots above the red line are the compounds that only increase the percentage not the number of NGN3$^+$ cells because of compound toxicity. FIG. 4B shows the chemical structures of other exemplary PKC inhibitors.

mRNA of HUES 8-derived pancreatic progenitor cells treated with DMSO was used as a control to normalize data.

Figure 6A:
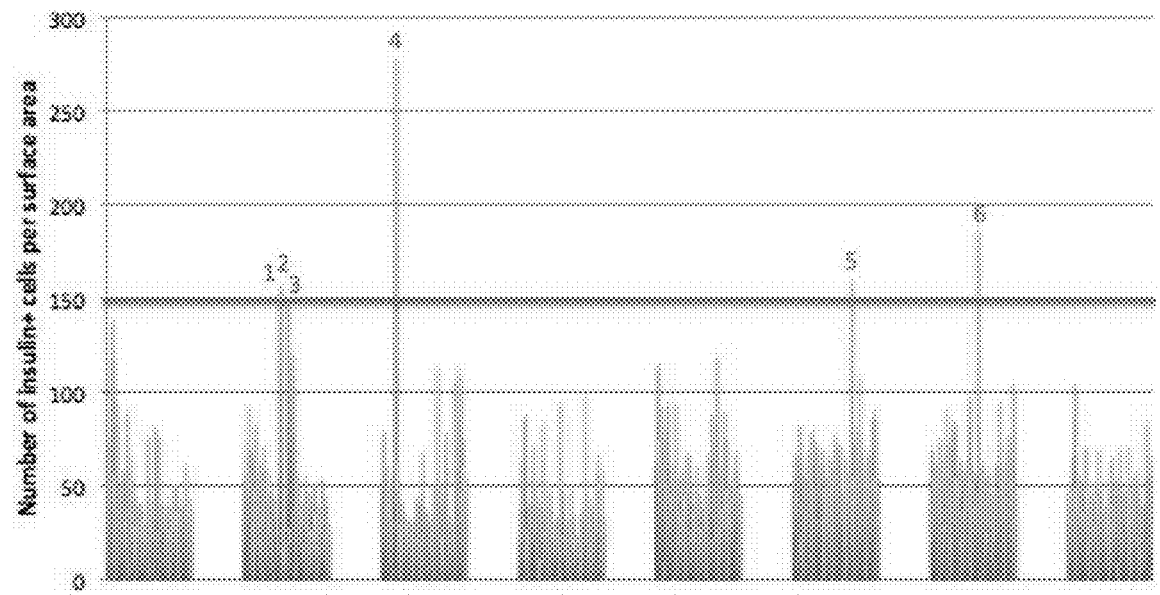
Figure 6B:
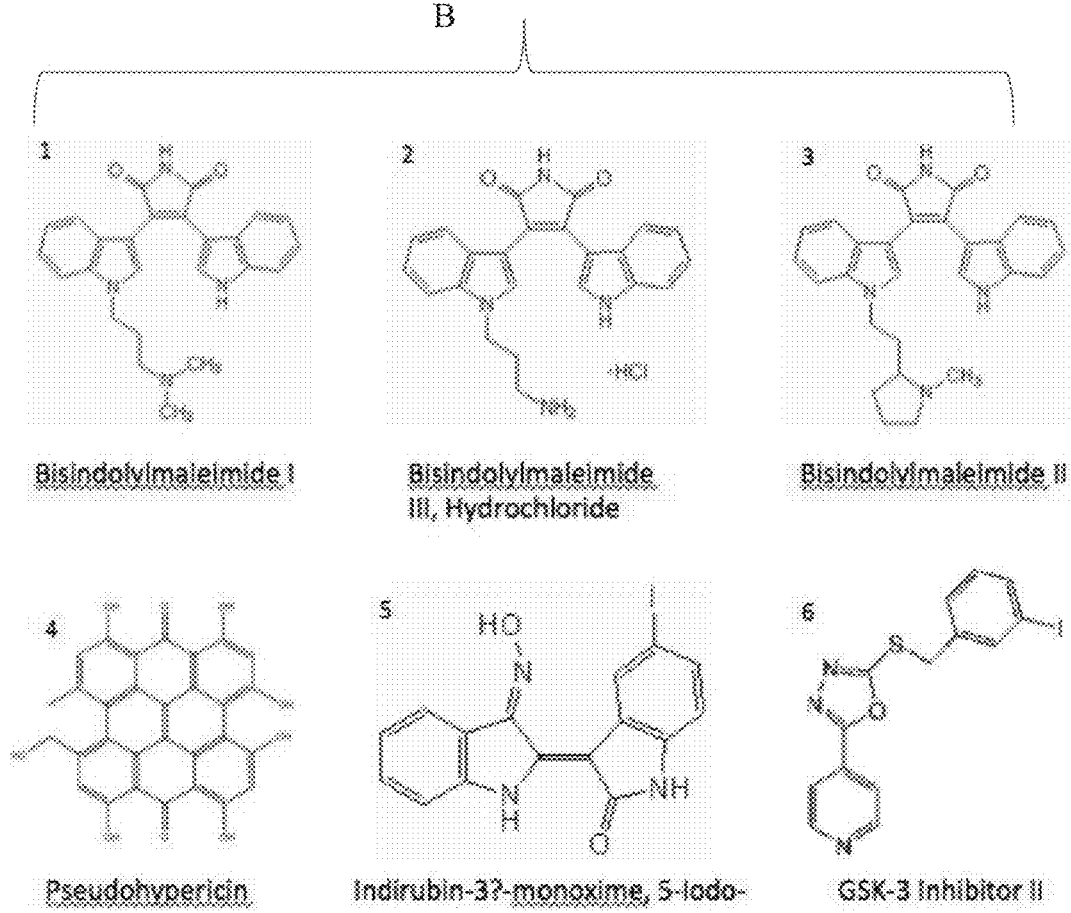

FIGS. 6A-6B show the data analysis of the second primary screen. FIG. 6A shows the data of primary screen. Each line represents one compound at 10 μM. 418 compounds and 366 DMSO controls were tested. The y-axis is the number of cells per surface area positively stained by the INS antibody. Primary hits (above the red line, numbered) were designated as compounds that induced INS in more than 148 INS' cells/defined area, which is 3 times higher than the average. FIG. 6B shows the chemical structures of exemplary hit compounds.

Figure 7:
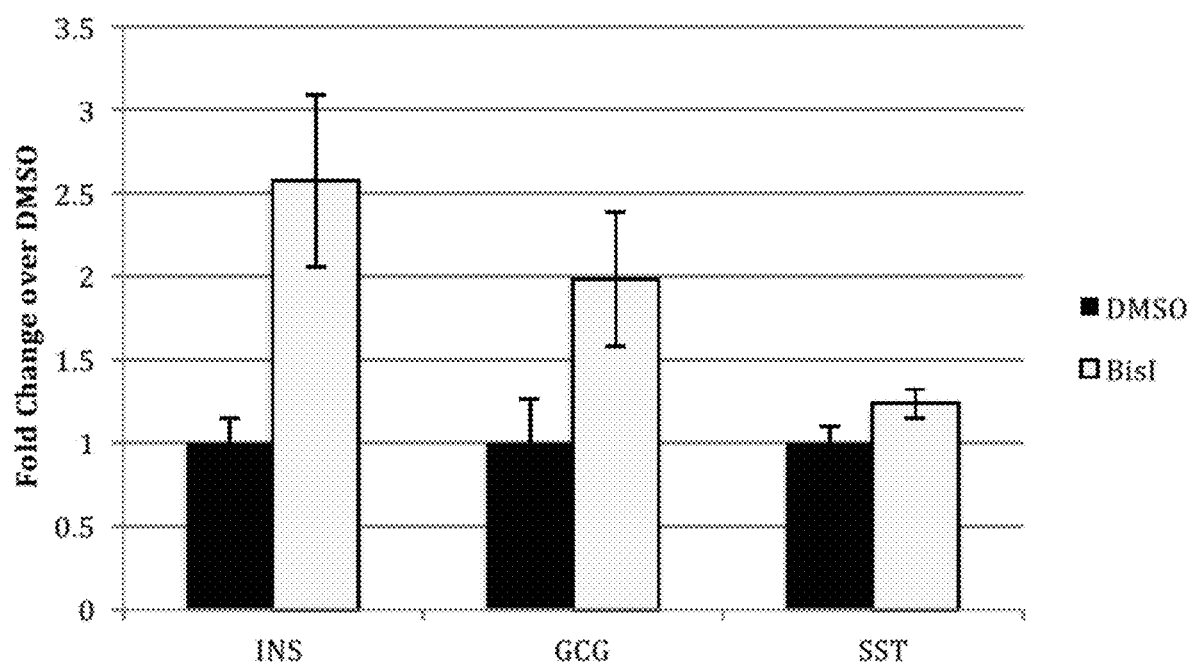

FIG. 7 shows that BisI induces expression of multiple endocrine markers. H1-derived pancreatic progenitors were treated for 3 days with DMSO or 3 μM BisI. qRT-PCR for INS, GCG and SST performed and shown as fold change over DMSO control.

DETAILED DESCRIPTION OF THE INVENTION

Described herein are methods for the generation of insulin positive β cells, by exposing Pdx+ pancreatic progenitor cells to one or more compounds described such as, for example, small molecule compounds. Also described herein are compositions comprising isolated populations of insulin positive cells. Compositions and kits comprising the compounds and/or cells described herein (e.g., made by method described herein) are also include in the description.

Definitions

For convenience, certain terms employed herein in the specification, examples and appended claims are collected here. Unless otherwise defined, all technical and scientific terms used herein have the same meaning as commonly understood by one of ordinary skill in the art to which this invention pertains.

The term "PKCβ" is used interchangeably herein with PCK beta or PKC-β, and refers to the amino acid sequences of substantially purified PKCβ obtained from any species, particularly mammalian, including bovine, ovine, porcine, murine, equine, and preferably human, from any source whether natural, synthetic, semi-synthetic, or recombinant.

The term "inhibitor" or "antagonist", as used herein in reference to a PKCβ antagonist or inhibitor, refers to a molecule which, when bound to PKCβ, decreases the amount or the duration of the effect of the biological or immunological activity of PKCβ, regardless of whether the inhibitor functions indirectly or directly on PKCβ.

The term "PKCβ inhibitor" or "PKCβ antagonist" as used herein refers to an agent that reduces or attenuates the biological activity of the PKCβ polypeptide in a cell, either by decreasing the activity of the PKCβ polypeptide or by effectively reducing the amount of PKCβ polypeptide in a cell or by decreasing the enzymatic activity of the PKCβ polypeptide. A "PKCβ inhibitor" thus refers to a molecule having the ability to inhibit a biological function of a native PKCβ, as well as a mutant PKCβ protein. Compounds that are PKCβ inhibitors include all solvates, hydrates, pharmaceutically acceptable salts, tautomers, stereoisomers, and prodrugs of the compounds. While in some embodiments PKCβ inhibitors herein specifically interact with, e.g. bind to, a PKCβ, molecules that inhibit PKCβ biological activity by interacting with other members of the PKCβ signal transduction pathway are also specifically included within this definition. Useful PKCβ inhibitors may selectively inhibit PKCβ, or may selectively inhibit calcium-independent or novel PKCβ isoforms. In some embodiments, PKCβ biological activity is inhibited by a PKCβ inhibitor as disclosed herein. Some PKCβ inhibitors may function by more than one mechanism to inhibit overall PKCβ activity in a cell.

The term a "selective" PKCβ inhibitor as used herein refers to an agent that inhibits PKCβ activity with a Ki at least 10-fold less, preferably, at least 100-fold less, than the Ki for inhibition of one or more other PKC isoforms (e.g., PKCδ, PKCε, PKCθ and PKCη).

A "PKCβ targeting treatment" is the use of one or more PKCβ inhibitors to therapeutically reduce PKCβ activity in a cell. A PKCβ inhibitors may preferably be agents that selectively inhibit PKCβ. As used herein, an agent that "selectively inhibits" PKCβ means an agent that reduces the activity of PKC beta more than it reduces the activity of any other PKC isoform.

The term "decreased PKCβ activity" means a decrease by a statistically significant amount in the total PKCβ polypeptide activity of the PKCβ enzyme as a result of inhibition with a PKCβ inhibitor compound as disclosed herein as compared to in the absence of such inhibitor.

The term "biologically active" as used herein refers to a protein having structural, regulatory, or biochemical functions of a naturally occurring molecule, and displays the activity of the molecule in a cellular and/or in vivo assay.

The term "differentiated cell" refers to any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process. Without wishing to be limited to theory, a pluripotent stem cell in the course of normal ontogeny can differentiate first to an endoderm cell that is capable of forming pancreas cells and other endoderm cell types. Further differentiation of an endoderm cell leads to the pancreatic pathway, where ~98% of the cells become exocrine, ductular, or matrix cells, and ~2% become endocrine cells. Early endocrine cells are islet progenitors, which can then differentiate further into insulin-producing cells (e.g. functional endocrine cells) which secrete insulin, glucagon, somatostatin, or pancreatic polypeptide. Endoderm cells can also be differentiate into other cells of endodermal origin, e.g. lung, liver, intestine, thymus etc.

As used herein, the term "somatic cell" refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein, the term "adult cell" refers to a cell found throughout the body after embryonic development.

The term "endoderm cell" as used herein refers to a cell which is from one of the three primary germ cell layers in the very early embryo (the other two germ cell layers are the mesoderm and ectoderm). The endoderm is the innermost of the three layers. An endoderm cell differentiates to give rise first to the embryonic gut and then to the linings of respiratory and digestive tracts (e.g. the intestine), the liver and the pancreas.

The term "a cell of endoderm origin" as used herein refers to any cell which has developed of differentiated from an endoderm cell. For example, a cell of endoderm origin includes cells of the liver, lung, pancrease, thymus, intestine, stomach and thyroid. Without wishing to be bound by theory, liver and pancreas progenitors (also referred to as pancreatic progenitors) are develop from endoderm cells in the embryonic foregut. Shortly after their specification, liver and pancreas progenitors rapidly acquire markedly different cellular functions and regenerative capacities. These changes are elicited by inductive signals and genetic regulatory factors that are highly conserved among vertebrates. Interest in the development and regeneration of the organs has been fueled by the intense need for hepatocytes and pancreatic β cells in the therapeutic treatment of liver failure and type I diabetes. Studies in diverse model organisms and humans have revealed evolutionarily conserved inductive signals and transcription factor networks that elicit the differentiation of liver and pancreatic cells and provide guidance for how to promote hepatocyte and β cell differentiation from diverse stem and progenitor cell types.

The term "definitive endoderm" as used herein refers to a cell differentiated from an endoderm cell and which can be differentiated into a pancreatic β-cell. A definitive endoderm cell expresses the marker Sox17. Other markers of definitive endoderm cells include, but are not limited to MIXL2, GATA4, HNF3b, GSC, FGF17, VWF, CALCR, FOXQ1, CMKOR1 and CRIP1. In particular, definitive endoderm cells herein express Sox17 and in some embodiments Sox17 and HNF3B, and do not express significant levels of GATA4, SPARC, APF or DAB. Definitive endoderm cells are not positive for the marker Pdx1 (e.g. they are Pdx1-negative). Definitive endoderm cells have the capacity to differentiate into cells including those of the liver, lung, pancreas, thymus, intestine, stomach and thyroid.

The terms "pancreatic progenitor" or "pancreatic precursor" are used interchangeably herein and refer to a cell which is capable of forming any of; pancreatic endocrine cells, or pancreatic exocrine cells or pancreatic duct cells.

The term "Pdx1-positive pancreatic progenitor" as used herein refers to a cell which is a pancreatic endoderm (PE) cell which has the capacity to differentiate into insulin-producing cells, such as pancreatic β-cells. A Pdx1-positive pancreatic progenitor expresses the marker Pdx1. Other markers include, but are not limited to Cdcp1, or Ptf1a, or HNF6 or Nkx2.2.

The term "pancreatic endoderm" refers to a cell of endoderm origin which is capable of differentiating into multiple pancreatic lineages, including pancreatic beta cells, but no longer has the capacity to differentiate into non-pancreatic lineages.

The term "exocrine cell" as used herein refers to a cell of an exocrine gland, i.e. a gland that discharges its secretion via a duct. In particular embodiments, an exocrine cells refers to a pancreatic exocrine cell, which is a pancreatic cell that produces enzymes that are secreted into the small intestine. These enzymes help digest food as it passes through the gastrointestinal tract. Pancreatic exocrine cells are also known as islets of Langerhans, that secrete two hormones, insulin and glucagon. A pancreatic exocrine cell can be one of several cell types: alpha-2 cells (which produce the hormone glucagon); or β-cells (which manufacture the hormone insulin); and alpha-1 cells (which produce the regulatory agent somatostatin). Non-insulin-producing exocrine cells as used herein refers to alpha-2 cells or alpha-1 cells. Note, the term pancreatic exocrine cells encompasses "pancreatic endocrine cells" which refer to a pancreatic cell that produces hormones (e.g., insulin (produced from β-cells) and glucagon (produced by alpha-2 cells) that are secreted into the bloodstream.

As used herein, the term "insulin-producing cell" refers to a cell differentiated from a pancreatic progenitor which secretes insulin. An insulin-producing cell includes pancreatic β-cells as that term is described herein, as well as pancreatic β-like cells that synthesize (i.e., transcribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. A population of insulin-producing cells e.g. produced by differentiating definitive endoderm cells to pancreatic progenitors and then subsequent differentiation into insulin-producing cells according to the methods of the present invention can be pancreatic β-cells or β-like cells (e.g., cells that have at least two characteristics of an endogenous β-cell). The novelty of the present composition and methods is not negated by the presence of cells in the population that produce insulin naturally (e.g., beta cells). It is also contemplated that the population of insulin-producing cells, e.g. produced by the methods as disclosed herein can comprise pancreatic β-cells or pancreatic β-like cells, and can also contain non-insulin-producing cells (i.e. cells of β-cell like phenotype with the exception they do not produce or secrete insulin).

As used herein, the term "endogenous β-cell" or endogenous "pancreatic β-cell" refers to an insulin-producing cell of the pancreas or a cell of a pancreatic β-cell (beta cell) phenotype. The phenotype of a pancreatic β-cell is well known by persons of ordinary skill in the art, and include, for example, secretion of insulin in response to an increase in glucose level, expression of markers such as c-peptide, PDX-1 polypeptide and Glut 2, as well as distinct morphological characteristics such as organized in islets in pancreas in vivo, and typically have small spindle like cells of about 9-15 μm diameter.

The term "pancreatic β-like cell" as used herein refers to as used herein refers to a cell produced by the methods as disclosed herein which expresses at least 15% of the amount of insulin expressed by an endogenous pancreatic beta-cell, or at least about 20% or at least about 30%, or at least about 40%, or at least about 50%, or at least about 60%, or at least about 70%, or at least about 80%, or at least about 90%, or at least about 100% or greater than 100%, such as at least about 1.5-fold, or at least about 2-fold, or at least about 2.5-fold, or at least about 3-fold, or at least about 4-fold or at least about 5-fold or more than about 5-fold the amount of the insulin secreted by an endogenous pancreatic bets-cell, or alternatively exhibits at least one, or at least two characteristics of an endogenous pancreatic beta-cell, for example, but not limited to, secretion of insulin in response to glucose, and expression of beta-cell markers, such as for example, c-peptide, Pdx1 and glut-2. In one embodiment, the pancreatic β-like cell is not an immortalized cell (e.g. proliferate indefinitely in culture). In one embodiment, the pancreatic β-like cell is not a transformed cell, e.g., a cell that exhibits a transformation property, such as growth in soft agar, or absence of contact inhibition.

The term "β-cell marker" refers to, without limitation, proteins, peptides, nucleic acids, polymorphism of proteins and nucleic acids, splice variants, fragments of proteins or nucleic acids, elements, and other analytes which are specifically expressed or present in pancreatic β-cells. Exemplary β-cell markers include, but are not limited to, pancreatic and duodenal homeobox 1 (PDX-1) polypeptide, insulin, c-peptide, amylin, E-cadherin, Hnf3β, PCI/3, Beta2, Nkx2.2, Nkx6.1, GLUT2, PC2, ZnT-8, and those described in Zhang et al., Diabetes. 50(10):2231-6 (2001). In some embodiment, the β-cell marker is a nuclear β-cell marker. In some embodiments, the β-cell marker is PDX-1 or PH3.

The term "non-insulin-producing cell" as used herein means any cell of endoderm origin that does not naturally synthesize, express, or secrete insulin constitutively or by induction. Thus, the term "non-insulin-producing cells" as used herein excludes pancreatic beta cells. Examples of non-insulin-producing cells that can be used in the methods of the present invention include pancreatic non-beta cells, such as amylase producing cells, acinar cells, cells of ductal adenocarcinoma cell lines (e.g., CD18, CD11, and Capan-I cells (see Busik et al., 1997; Schaffert et al. 1997). Non-pancreatic cells of endoderm origin could also be used, for example, non-pancreatic stem cells and cells of other endocrine or exocrine organs, including, for example, liver cells, tymus cells, thyroid cells, intestine cells, lung cells and pituitary cells. In some embodiments, the non-insulin-producing endodermal cells can be mammalian cells or, even more specifically, human cells. Examples of the present method using mammalian pancreatic non-islet, pancreatic amylase producing cells, pancreatic acinar cells are provided herein.

The term "phenotype" refers to one or a number of total biological characteristics that define the cell or organism under a particular set of environmental conditions and factors, regardless of the actual genotype.

The term "pluripotent" as used herein refers to a cell with the capacity, under different conditions, to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g. iPS cells as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refers to a pluripotent stem cell artificially derived (e.g., induced or by complete reversal) from a non-pluripotent cell, typically an adult somatic cell, for example, by inducing a forced expression of one or more genes.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with One daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "pancreas" refers to a glandular organ that secretes digestive enzymes and hormones. In humans, the pancreas is a yellowish organ about 7 in. (17.8 cm) long and 1.5 in. (3.8 cm) wide. It lies beneath the stomach and is connected to the small intestine, muscular hoselike portion of the gastrointestinal tract extending from the lower end of the stomach (pylorus) to the anal opening. Most of the pancreatic tissue consists of grapelike clusters of cells that produce a clear fluid (pancreatic juice) that flows into the duodenum through a common duct along with bile from the liver. Pancreatic juice contains three digestive enzymes: tryptase, amylase, and lipase, that, along with intestinal enzymes, complete the digestion of proteins, carbohydrates, and fats, respectively. Scattered among the enzyme-producing cells of the pancreas are small groups of endocrine cells, called the islets of Langerhans, that secrete two hormones, insulin and glucagon. The pancreatic islets contain several types of cells: alpha-2 cells, which produce the hormone glucagon; beta cells (also referred to herein as "pancreatic β-cells"), which manufacture the hormone insulin; and alpha-1 cells, which produce the regulatory agent somatostatin. These hormones are secreted directly into the bloodstream, and together, they regulate the level of glucose in the blood. Insulin lowers the blood sugar level and increases the amount of glycogen (stored carbohydrate) in the liver; glucagon has the opposite action. Failure of the insulin-secreting cells to function properly results in diabetes or diabetes mellitus.

The term "reprogramming" as used herein refers to the process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. Reprogramming as used herein also encompasses partial reversion of a cells differentiation state, for example to a multipotent state or to a somatic cell that is neither pluripotent or multipotent, but is a cell that has lost one or more specific characteristics of the differentiated cell from which it arises, e.g. direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "contacting" (i.e., contacting a Pdx+ pancreatic progenitor cell with a compound) is intended to include incubating the compound and the cell together in vitro (e.g., adding the compound to cells in culture). In some embodiments, the term "contacting" is not intended to include the in vivo exposure of cells to the compounds as disclosed herein that may occur naturally in a subject (i.e., exposure that may occur as a result of a natural physiological process). The step of contacting a Pdx+ pancreatic progenitor with a compound as disclosed herein can be conducted in any suitable manner. For example, the cells may be treated in adherent culture, or in suspension culture. It is understood that the cells contacted with a compound as disclosed herein can also be simultaneously or subsequently contacted with another agent, such as a growth factor or other differentiation agent or environments to stabilize the cells, or to differentiate the cells further. Similarly, a Pdx+ pancreatic progenitor can be contacted with a compound as disclosed herein and then with a second compound as disclosed herein. In some embodiments, the cell is contacted with a compound as disclosed herein and a second compound as disclosed herein and the contact is temporal separated, and in some embodiments, a Pdx+ pancreatic progenitor is contacted with one or more compound as disclosed herein substantially simultaneously.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "genetically modified" or "engineered" cell as used herein refers to a cell into which an exogenous nucleic acid has been introduced by a process involving the hand of man (or a descendant of such a cell that has inherited at least a portion of the nucleic acid). The nucleic acid may for example contain a sequence that is exogenous to the cell, it may contain native sequences (i.e., sequences naturally found in the cells) but in a non-naturally occurring arrangement (e.g., a coding region linked to a promoter from a different gene), or altered versions of native sequences, etc. The process of transferring the nucleic into the cell can be achieved by any suitable technique. Suitable techniques include calcium phosphate or lipid-mediated transfection, electroporation, and transduction or infection using a viral vector. In some embodiments the polynucleotide or a portion thereof is integrated into the genome of the cell. The nucleic acid may have subsequently been removed or excised from the genome, provided that such removal or excision results in a detectable alteration in the cell relative to an unmodified but otherwise equivalent cell.

The term "identity" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs known in the art. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. ScL USA 87:22264-2268, 1990) modified as in Karlin and Altschul, Proc. Natl. Acad. ScL USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm.nih.gov" for these programs. In a specific embodiment, percent identity is calculated using BLAST2 with default parameters as provided by the NCBI.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of definitive endoderm cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not definitive endoderm cells or their progeny as defined by the terms herein. In some embodiments, the present invention encompasses methods to expand a population of definitive endoderm cells, wherein the expanded population of definitive endoderm cells is a substantially pure population of definitive endoderm cells. Similarly, with regard to a "substantially pure" or "essentially purified" population of Pdx1-positive pancreatic progenitors, refers to a population of cells that contain fewer than about 20%, more preferably fewer than about 15%, 10%, 8%, 7%, most preferably fewer than about 5%, 4%, 3%, 2%, 1%, or less than 1%, of cells that are not Pdx1-positive pancreatic progenitors or their progeny as defined by the terms herein. In some embodiments, the present invention encompasses methods to expand a population of Pdx1-positive pancreatic progenitors, wherein the expanded population of Pdx1-positive pancreatic progenitors is a substantially pure population of Pdx1-positive pancreatic progenitors.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells to renew themselves by dividing into the same non-specialized cell type over long periods, and/or many months to years. In some instances, proliferation refers to the expansion of cells by the repeated division of single cells into two identical daughter cells.

The term "lineages" as used herein describes a cell with a common ancestry or cells with a common developmental fate. In the context of a cell that is of endoderm origin or is "endodermal linage" this means the cell was derived from an endoderm cell and can differentiate along the endoderm lineage restricted pathways, such as one or more developmental lineage pathways which give rise to definitive endoderm cells, which in turn can differentiate into liver cells, thymus, pancreas, lung and intestine.

As used herein, the term "xenogeneic" refers to cells that are derived from different species.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

The term "polynucleotide" is used herein interchangeably with "nucleic acid" to indicate a polymer of nucleosides. Typically a polynucleotide of this invention is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. However the term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e. the succession of letters used as abbreviations for bases) that biochemically characterizes a specific nucleic acid. A polynucleotide sequence presented herein is presented in a 5' to 3' direction unless otherwise indicated.

The terms "polypeptide" as used herein refers to a polymer of amino acids. The terms "protein" and "polypeptide" are used interchangeably herein. A peptide is a relatively short polypeptide, typically between about 2 and 60 amino acids in length. Polypeptides used herein typically contain amino acids such as the 20 L-amino acids that are most commonly found in proteins. However, other amino acids and/or amino acid analogs known in the art can be used. One or more of the amino acids in a polypeptide may be modified, for example, by the addition of a chemical entity such as a carbohydrate group, a phosphate group, a fatty acid group, a linker for conjugation, functionalization, etc. A polypeptide that has a non-polypeptide moiety covalently or non-covalently associated therewith is still considered a "polypeptide". Exemplary modifications include glycosylation and palmitoylation. Polypeptides may be purified from natural sources, produced using recombinant DNA technology, synthesized through chemical means such as conventional solid phase peptide synthesis, etc. The term "polypeptide sequence" or "amino acid sequence" as used herein can refer to the polypeptide material itself and/or to the sequence information (i.e., the succession of letters or three letter codes used as abbreviations for amino acid names) that biochemically characterizes a polypeptide. A polypeptide sequence presented herein is presented in an N-terminal to C-terminal direction unless otherwise indicated.

The term a "variant" in referring to a polypeptide could be, e.g., a polypeptide at least 80%, 85%, 90%, 95%, 98%, or 99% identical to full length polypeptide. The variant could be a fragment of full length polypeptide. The variant could be a naturally occurring splice variant. The variant could be a polypeptide at least 80%, 85%, 90%, 95%, 98%, or 99% identical to a fragment of the polypeptide, wherein the fragment is at least 50%, 60%, 70%, 80%, 85%, 90%, 95%, 98%, or 99% as long as the full length wild type polypeptide or a domain thereof having an activity of interest, such as the ability to detect the presence of a definitive endoderm cell or Pdx1-positive pancreatic progenitor. In some embodiments the domain is at least 100, 200, 300, or 400 amino acids in length, beginning at any amino acid position in the sequence and extending toward the C-terminus. Variations known in the art to eliminate or substantially reduce the activity of the protein are preferably avoided. In some embodiments, the variant lacks an N- and/or C-terminal portion of the full length polypeptide, e.g., up to 10, 20, or 50 amino acids from either terminus is lacking. In some embodiments the polypeptide has the sequence of a mature (full length) polypeptide, by which is meant a polypeptide that has had One or more portions such as a signal peptide removed during normal intracellular proteolytic processing (e.g., during co-translational or post-translational processing). In some embodiments wherein the protein is produced other than by purifying it from cells that naturally express it, the protein is a chimeric polypeptide, by which is meant that it contains portions from two or more different species. In some embodiments wherein a protein is produced other than by purifying it from cells that naturally express it, the protein is a derivative, by which is meant that the protein comprises additional sequences not related to the protein so long as those sequences do not substantially reduce the biological activity of the protein.

The term "functional fragments" as used herein refers to a polypeptide having an amino acid sequence which is smaller in size than, but substantially homologous to, the polypeptide of which it is a fragment, and where the functional fragment polypeptide sequence is about at least 50%, or 60% or 70% or at 80% or 90% or 100% or greater than 100% (for example 1.5-fold, 2-fold, 3-fold, 4-fold or greater than 4-fold) biologically active as the polypeptide of which it is a fragment. Functional fragment polypeptides may have additional functions that can include decreased antigenicity, increased DNA binding (as in transcription factors), or altered RNA binding (as in regulating RNA stability or degradation).

The term "vector" refers to a carrier DNA molecule into which a DNA sequence can be inserted for introduction into a host cell. Preferred vectors are those capable of autonomous replication and/or expression of nucleic acids to which they are linked. Vectors capable of directing the expression of genes to which they are operatively linked are referred to herein as "expression vectors". Thus, an "expression vector" is a specialized vector that contains the necessary regulatory regions needed for expression of a gene of interest in a host cell. In some embodiments the gene of interest is operably linked to another sequence in the vector. Vectors can be viral vectors or non-viral vectors. Should viral vectors be used, it is preferred the viral vectors are replication defective, which can be achieved for example by removing all viral nucleic acids that encode for replication. A replication defective viral vector will still retain its infective properties and enters the cells in a similar manner as a replicating adenoviral vector, however once admitted to the cell a replication defective viral vector does not reproduce or multiply. Vectors also encompass liposomes and nanoparticles and other means to deliver DNA molecule to a cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g EPV and EBV vectors.

The terms "regulatory sequence" and "promoter" are used interchangeably herein, and refer to nucleic acid sequences, such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

As used herein, the term "transcription factor" refers to a protein that binds to specific parts of DNA using DNA binding domains and is part of the system that controls the transfer (or transcription) of genetic information from DNA to RNA. As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or Renilla luciferase) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions". To ensure an effective selection, a population of cells can be maintained for a under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

A "reporter gene" as used herein encompasses any gene that is genetically introduced into a cell that adds to the phenotype of the stem cell. Reporter genes as disclosed in this invention are intended to encompass fluorescent, luminescent, enzymatic and resistance genes, but also other genes which can easily be detected by persons of ordinary skill in the art. In some embodiments of the invention, reporter genes are used as markers for the identification of particular stem cells, cardiovascular stem cells and their differentiated progeny. A reporter gene is generally operatively linked to sequences that regulate its expression in a manner dependent upon one or more conditions which are monitored by measuring expression of the reporter gene. In some cases, expression of the reporter gene may be determined in live cells. Where live cell reporter gene assays are used, reporter gene expression may be monitored at multiple timepoints, e.g., 2, 3, 4, 5, 6, 8, or 10 or more timepoints. In some cases, where a live cell reporter assay is used, reporter gene expression is monitored with a frequency of at least about 10 minutes to about 24 hours, e.g., 20 minutes, 1 hour, 2 hours, 3 hours, 4 hours, 5 hours, 6 hours, 7 hours, 8 hours, 9 hours, 10 hours, 12 hours, 18 hours, or another frequency from any integer between about 10 minutes to about 24 hours.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "diabetes" and "diabetes mellitus" are used interchangeably herein. The World Health Organization defines the diagnostic value of fasting plasma glucose concentration to 7.0 mmol/l (126 mg/dl) and above for Diabetes Mellitus (whole blood 6.1 mmol/1 or 110 mg/dl), or 2-hour glucose level 11.1 mmol/L or higher (200 mg/dL or higher). Other values suggestive of or indicating high risk for Diabetes Mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males:waist to hip ratio higher than 0.90; females:waist to hip ratio higher than 0.85) and/or body mass index exceeding 30 kg/m$^2$; microalbuminuria, where the urinary albumin excretion rate 20 μg/min or higher, or albumin:creatinine ratio 30 mg/g or higher). The term diabetes encompases all forms of diabetes, e.g. Type I, Type II and Type 1.5.

The terms "treat", "treating", "treatment", etc., as applied to an isolated cell, include subjecting the cell to any kind of process or condition or performing any kind of manipulation or procedure on the cell. As applied to a subject, the terms refer to providing medical or surgical attention, care, or management to an individual. The individual is usually ill or injured, or at increased risk of becoming ill relative to an average member of the population and in need of such attention, care, or management.

As used herein, the terms "treating" and "treatment" refer to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

As used herein, the terms "administering," "introducing" and "transplanting" are used interchangeably in the context of the placement of cells, e.g. insulin-producing cells or pancreatic β-cells or pancreatic β-like cells) of the invention into a subject, by a method or route which results in at least partial localization of the introduced cells at a desired site. The cells e.g. insulin-producing cells or pancreatic β-cells or pancreatic β-like cells can be implanted directly to the pancreas, or alternatively be administered by any appropriate route which results in delivery to a desired location in the subject where at least a portion of the implanted cells or components of the cells remain viable. The period of viability of the cells after administration to a subject can be as short as a few hours, e.g. twenty-four hours, to a few days, to as long as several years. In some instances, the cells can also be administered at a non-pancreatic location, such as in the liver or subcutaneously, for example, in a capsule to maintain the implanted cells at the implant location and avoid migration of the implanted cells.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration of cardiovascular stem cells and/or their progeny and/or compound and/or other material other than directly into the central nervous system, such that it enters the animal's system and, thus, is subject to metabolism and other like processes, for example, subcutaneous administration.

The term "tissue" refers to a group or layer of specialized cells which together perform certain special functions. The term "tissue-specific" refers to a source of cells from a specific tissue.

The term "halogen" refers to any radical of fluorine, chlorine, bromine or iodine.

The term "alkyl" refers to saturated non-aromatic hydrocarbon chains that may be a straight chain or branched chain, containing the indicated number of carbon atoms (these include without limitation propyl, allyl, or propargyl), which may be optionally inserted with N, O, S, S(O), or C(O). For example, $C_1$-$C_6$ indicates that the group may have from 1 to 6 (inclusive) carbon atoms in it. Exemplary alkyl groups include, but are not limited to, methyl, ethyl, propyl, isopropyl, butyl, t-butyl, and the like.

The term "alkenyl" refers to an alkyl that comprises at least one double bond. Exemplary alkenyl groups include, but are not limited to, for example, ethenyl, propenyl, butenyl, 1-methyl-2-buten-1-yl and the like.

The term "alkynyl" refers to an alkyl that comprises at least one triple bond.

The term "alkylenyl" refers to a divalent group derived from a straight or branched chain alkyl. Exemplary alkylenyls include, but are not limited to, —$CH^2$—, —CH($CH_3$)—, —C($CH_3$)$_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, and —$CH_2CH(CH_3)CH_2$—.

The term "alkenylenyl" refers to an alkylenyl that comprises at least one double bond.

The term "alkynylenyl" refers to an alkylenyl that comprises at least one triple bond.

The term "alkoxy" refers to an —O-alkyl radical.

The term "thioalkoxy" refers to an —S-alkyl radical.

The term "aryl" refers to monocyclic, bicyclic, or tricyclic aromatic ring system wherein 0, 1, 2, 3, or 4 atoms of each ring may be substituted by a substituent. Exemplary aryl groups include, but are not limited to, phenyl, naphthyl, anthracenyl, azulenyl, fluorenyl, indanyl, indenyl, naphthyl, phenyl, tetrahydronaphthyl, and the like.

The term "cyclyl" refers to saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Exemplary cycloalkyl groups include, but are not limited to, cyclopropyl, cyclobutyl, cyclopentyl, cyclopentenyl, cyclohexyl, cyclohexenyl, cycloheptyl, cyclooctyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Exemplary heteroaryl groups include, but are not limited to, phenyl, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Exemplary heterocyclyl groups include, but are not limited to piperazinyl, pyrrolidinyl, dioxanyl, morpholinyl, tetrahydrofuranyl, and the like.

The term "optionally substituted" means that the specified group or moiety, such as an aryl group, heteroaryl group and the like, is unsubstituted or is substituted with one or more (typically 1-4 substituents) independently selected from the group of substituents listed below in the definition for "substituents" or otherwise specified.

The term "substituents" refers to a group "substituted" on an alkyl, alkenyl, alkynyl, cycloalkyl, aryl, heterocyclyl, or heteroaryl group at any atom of that group. Suitable substituents include, without limitation, halo, hydroxy, oxo, nitro, haloalkyl, alkyl, alkenyl, alkynyl, alkaryl, aryl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

The terms "decrease", "reduced", "reduction", "decrease" or "inhibit" are all used herein generally to mean a decrease by a statistically significant amount. For example, "reduced", "reduction" or "decrease" or "inhibit" can mean a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e., absent as compared to a reference sample), or any decrease between 10-100% as compared to a reference level.

The terms "increased", "increase" or "enhance" or "activate" are all used herein to generally mean an increase by a statically significant amount. For example the terms "increased", "increase" or "enhance" or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

Protein Kinase C (PKC)

Protein kinase C (PKC) is a superfamily of lipid-activated Ser/Thr kinases involved in multiple signal transduction pathways. Protein kinase C ("PKC") is a key enzyme in signal transduction involved in a variety of cellular functions, including cell growth, regulation of gene expression, and ion channel activity. There are thirteen PKC-isoforms that have been identified and are classified according to their regulation by cellular signaling molecules such as diacylglycerol, phospholipids, and calcium. The protein kinase C isozymes, alpha, beta (two splice variants PKCβ1 and PKCβII) and γ, require membrane phospholipids, calcium and diacylglycerolphorbol esters for full activation. The delta, epsilon, eta, and theta forms of PKC are calcium-independent in their mode of activation. The zeta and lambda forms of PKC are independent of both calcium and diacylglycerol and are believed to require only membrane phospholipids for their activation.

The tissue-specific expression and activation of PKC-isoforms suggests that individual PKC-isoforms might be potential therapeutic targets. For diabetes, activation of PKC-beta has been demonstrated in tissues of diabetic animals and has been implicated in the development of microvascular abnormalities related to the hyperglycemic state. Genetic polymorphisms have been identified in the 5'-flanking upstream region of the PKCβ gene in Japanese patients with type II diabetes. This PKCβ genetic variation was associated with a significant increase in the susceptibility to develop diabetic vascular complications and macrovascular diseases such as coronary heart disease.

Studies on the subcellular distribution of PKC isozymes demonstrate that activation of PKC results in its redistribution in the cells (also termed translocation), such that activated PKC isozymes associate with the plasma membrane, cytoskeletalelements, nuclei, and other subcellular compartments (Saito, N. et al., Proc. Natl. Acad. Sci. USA 86:3409-3413 (1989); Papadopoulos, V. and Hall, P. F. J. Cell Biol. 108:553-567 (1989); Mochly-Rosen, D., et al., Molec. Biol. Cell (formerly CellReg.) 1:693-706, (1990)). The unique cellular functions of different PKC isozymes are determined by their subcellular location. For example, activated βIPKC is found inside the nucleus, whereas activated βIIPKC is found at theperinucleus and cell periphery of cardiac myocytes (Disatnik, M. H., et al., Exp. Cell Res. 210:287-297 (1994)). εPKC, a member of the novel PKC family independent from calcium but requiring phospholipids for activation, is found in primaryafferent neurons both in the dorsal root ganglia as well as in the superficial layers of the dorsal spinal cord.

The localization of different PKC isozymes to different areas of the cell in turn appears due to binding of the activated isozymes to specific anchoring molecules termed Receptors for Activated C-Kinase ("RACKs"). RACKs are thought to function by selectively anchoring activated PKC isozymes to their respective subcellular sites. RACKs bind only fully activated PKC and are not necessarily substrates of the enzyme. Nor is the binding to RACKs mediated via the catalytic domain of the kinase (Mochly-Rosen, D., et al., Proc. Natl. Acad. Sci. USA 88:3997-4000 (1991)). Translocation of PKC reflects binding of the activated enzyme to RACKs anchored to the cell particulate fraction and the binding to RACKs is required for PKC to produce itscellular responses (Mochly-Rosen, D., et al., Science 268:247-251 (1995)). Inhibition of PKC binding to RACKs in vivo inhibits PKC translocation and PKC-mediated function (Johnson, J. A., et al., J. Biol. Chem., 271:24962-24966 (1996a); Ron, D., et al., Proc. Natl. Acad. Sci. USA 92:492-496 (1995); Smith, B. L. and Mochly-Rosen, D., Biochem. Biophys. Res. Commun., 188:1235-1240 (1992)).

In general, translocation of PKC is required for proper function of PKC isozymes. Peptides that mimic either the PKC-binding site on RACKs (Mochly-Rosen, D., et al., J. Biol. Chem., 226:1466-1468 (1991a); Mochly-Rosen, D., et al., 1995) or the RACK-binding site on PKC (Ron, et al., 1995; Johnson, J. A., et al., 1996a) are isozyme-specific translocation inhibitors of PKC that selectively inhibit the function of the enzyme in vivo.

An inhibitor of PKC-β activity can act directly on PKC-β (e.g., an inhibitor of PKC-β) or act to reduce or eliminate the expression level of PKC-β in targeted cells, e.g., pancreatic progenitor cells.

Exemplary direct inhibitors of PKC-beta activity include, without limitation, antibodies or antibody fragments that bind specifically to PKC-beta, and small molecule PKC-beta inhibitors such as ruboxistaurin mesylate (LY333531, Lilly) (13-((dimethylamino)methyl)-10,11,14,15-tetrahydro-4,9:16,21-dimetheno-1H,13H-dibenzo(e,k)pyrrolo(3,4-h)(1,4,13)oxadiazacyclohexadecene-1,3(2H)-dione), cicletanine ((+/−)-3-(p-chlorophenyl)-1,3-dihydro-6-methylfuro(3,4-c)pyridin-7-ol), and enzastaurin (LY317615.HCl) (3-(1-methyl-1H-indol-3-yl)-4-(1-(1-(pyridin-2-ylmethyl)piperidin-4-yl)-1H-indol-3-yl)-1H-pyrrole-2,5-dione monohydrochloride).

Cicletanine when used herein when unmodified by such descriptors as racemic, enantiomeric, non-racemic, is intended to include any and all of these chemical entities: racemic cicletanine, (−) cicletanine enantiomer, (+) cicletanine enantiomer, non-racemic mixtures of the two cicletanine enantiomers.

PKC-β1 is targeted most strongly by PRE 1 (RRKKGGKDFVVKR (SEQ. ID. NO.1)) and PRE 3 (Ac-AKGIQEVKGGDAQNLIGISI-NH$_2$ (SEQ. ID. NO.2)); PKC-βII is targeted most strongly by PRE 9 (Ac-isigilg-nadk-NH$_2$ (SEQ. ID. NO.3)). US Application Publ. No. 20100041597 to Phipps et al.

3-amido-pyrrolo[3,4-C]pyrazole-5(1H,4H,6H) carbaldehyde PKC-beta inhibitors are described in U.S. Application Publ. No. 20100249128 to Botrous et al., which is hereby incorporated by reference in its entirety. Exemplary compounds in this family of PKC-beta selective inhibitors include, without limitation:

N-(5-((2R,5S)-2,5-dimethyl-1-((tetrahydro-2H-pyran-4-yl) methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl) piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-({[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl) piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and N-(5-{[2S,5R)-2,5-dimethyl-4-(tetrahydro-2H-pyran-4-ylmethyl)piperazin-1-yl]carbonyl)}-6,6-dimethyl-1,4,5,6-tetrahydropyrrolo[3,4-c]pyrazol-3-yl)-5-(trifluoromethyl) pyridine-2-carboxamide.

3-amino-pyrrolo[3,4-c]pyrazole-5(1H,4H,6H) carbaldehyde PKC-beta inhibitors are described in U.S. Application Publ. No. 20100130501 to Li et al., which is hereby incorporated by reference in its entirety. Exemplary compounds in this family of PKC-beta selective inhibitors include, without limitation:

N4-(6,6-dimethyl-5-{[(2S)-2,4,5,5-tetramethylpiperazin-1-yl]carbony-l}-1,4,5,6-tetrahydropyrrolo[3,4-c]pyrazol-3-yl)-N2-ethyl-5-fluoropyrimidine-2,4-diamine;

N$^4$-(6,6-dimethyl-5-{[(2S)-2,4,5,5-tetramethylpiperazin-1-yl]ca-rbonyl}-1,4,5,6-tetrahydropyrrolo[3,4-c]pyrazol-3-yl)-5-fluoro-N$^2$,N$^2$-dimethylpyrimidine-2,4-diamine, N$^2$-cyclopropyl-N$^4$-(6,6-dimethyl-5-{[(2S)-2,4,5,5-tetramethylpiperaz-in-1-yl]carbonyl}-1,4,5,6-tetrahydropyrrolo[3,4-c]pyrazol-3-yl)-5-fluoropyrimidine-2,4-diamine;

N$^4$-(6,6-dimethyl-5-{[(2S)-2,4,5,5-tetramethylpiperazin-1-yl]car-rbonyl}-1,4,5,6-tetrahydropyrrolo[3,4-c]pyrazol-3-yl)-5-fluoro-N$^2$-methylpyrimidine-2,4-diamine;

N$^4$-(6,6-dimethyl-5-{[(2S)-2,4,5,5-tetramethylpiperazin-1-yl]car-rbonyl}-1,4,5,6-tetrahydropyrrolo[3,4-c]pyrazol-3-yl)-5-fluoro-N$^2$-iso-propylpyrimidine-2,4-diamine;

N$^4$-(6,6-dimethyl-5-{[(2S)-2,4,5,5-tetramethylpiperazin-1-yl]car-rbonyl}-1,4,5,6-tetrahydropyrrolo[3,4-c]pyrazol-3-yl)-N$^2$-ethylpyrimidine-2,4-diamine;

N$^4$-(6,6-dimethyl-5-{[(2S)-2,4,5,5-tetramethylpiperazin-1-yl]car-rbonyl}-1,4,5,6-tetrahydropyrrolo[3,4-c]pyrazol-3-yl)-N$^2$,N$^2$-dimethylpyrimidine-2,4-diamine;

5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]-pyrazol-3-amine;

N$^4$-(5-{[(2S,5R)-2,5-dimethyl-4-(tetrahydro-2H-pyran-4-ylmethyl) piperazin-1-yl]carbonyl}-6,6-dimethyl-1,4,5,6-tetrahydropyrrolo[3,4-c]pyrazol-3-yl)-N$^2$-ethyl-5-fluoropyrimidine-2,4-diamine;

N$^4$-(5-{[(2S,5R)-2,5-dimethyl-4-(tetrahydro-2H-pyran-4-yl)piper-azin-1-yl]carbonyl}-6,6-dimethyl-1,4,5,6-tetrahydropyrrolo[3,4-c]pyrazol-3-yl)-N$^2$-ethyl-5-fluoropyrimidine-2,4-diamine;

N$^2$-ethyl-5-fluoro-N$^4$-(5-{[(2S,5R)-4-(3-methoxypropyl)-2,5-dimethylpiperazin-1-yl]carbonyl}-6,6-dimethyl-1,4,5,6-tetrahydropyrrolo[3-,4-c]pyrazol-3-yl)pyrimidine-2,4-diamine acetate salt;

N$^4$-(6,6-dimethyl-5-{[(2S,5R)-2,4,5-trimethylpiperazin-1-yl]car-bonyl}-1,4,5,6-tetrahydropyrrolo[3,4-c]pyrazol-3-yl)-N$^2$-ethyl-5-fluoropyrimidine-2,4-diamine;

4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile;

N-(2-ethyl-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine;

2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

N-(5-fluoro-2-methylpyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-(5-fluoro-2-propylpyrimidin-4-yl)-6,6-dimethyl-5-{[(2S)-2,4,5,5-tetramtethylpiperazin-1-yl]carbonyl}-1,4,5,6-tetrahydropyrrolo[3,4-c]pyrazol-3-amine;

N-(5-fluoro-2-isopropylpyrimidin-4-yl)-6,6-dimethyl-5-{[(2S)-2,4,5,-5-tetramethylpiperazin-1-yl]carbonyl}-1,4,5,6-tetrahydropyrrolo[3,4-c]pyrazol-3-amine;

N-(3-fluoro-6-methylpyridin-2-yl)-6,6-dimethyl-5-{[(2S,5R)-2,4,5-trimethylpiperazin-1-yl]carbonyl)}-1,4,5,6-tetrahydropyrrolo[3,4-c]pyrazol-3-amine;

5-{[(3S,8aS)-3,8a-dimethylhexahydropyrrolo[1,2-a]pyrazin-2(1H)-yl]carbonyl}-N-(3-fluoro-6-methylpyridin-2-yl)-6,6-dimethyl-1,4,5,6-tetrahydropyrrolo[3,4-c]pyrazol-3-amine;

N-(3-fluoro-6-methylpyridin-2-yl)-6,6-dimethyl-5-({[(3S,8aS)-3-methylhexahydropyrrolo[1,2-a]pyrazin-2(1H)-yl]carbonyl}-1,4,5,6-tetrahydropyrro-lo[3,4-c]pyrazol-3-amine;

N-(3-fluoro-6-methylpyridin-2-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(methoxymethyl)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

5-{[(2S,5R)-2,5-dimethyl-4-(tetrahydro-2H-pyran-4-ylmethyl) piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine;

5-{[(2S,5R)-2,5-dimethyl-4-(tetrahydro-2H-pyran-4-ylmethyl) piperazin-1-yl]carbonyl}-6,6-dimethyl-N-(4-methylpyrimidin-2-yl)-1,4,5,6-tetrahydropyrrolo[3,4-c]pyrazol-3-amine;

N-(2-ethoxy-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(2-ethoxy-5-fluoropyrimidin-4-yl)-6,6-dimethyl-5-{[4-ethyl(2S,5R)-2,5-dimethylpiperazin-1-yl]carbonyl})-1,4,5,6-tetrahydropyrrolo[3,-4-c]pyrazol-3-amine;

N-(2-ethoxy-5-fluoropyrimidin-4-yl)-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine;

N-(2-ethoxy-5-fluoropyrimidin-4-yl)-5-{[(2S,5R)-4-(3-methoxy propyl)-2,5-dimethylpiperazin-1-yl]carbonyl}-6,6-dimethyl-1,4,5,6-tetrahydro-pyrrolo[3,4-c]pyrazol-3-amine;

N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetra hydropyrrolo[3,4-c]pyrazol-3-amine;

N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-[5-fluoro-2-(2,2,2-trifluoroethoxy)pyrimidin-4-yl]-6,6-dimethyl-5-([(2S)-2,4,5,5-tetramethylpiperazin-1-yl]carbonyl)-1,4,5,6-tetrahydropyrrolo[3,4-c]pyrazol-3-amine;

5-{[(2S,5R)-2,5-dimethyl-4-(tetrahydro-2H-pyran-4-ylmethyl) piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-ylmethyl) piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine; and 2-((5S)-4-([3-{[5-fluoro-2-(methoxymethyl)pyrimidin-4-yl]amino}-6,6-dimethyl-4,6-dihydropyrrolo[3,4-c]pyrazol-5(1H)-yl]carbonyl)-1,5-dimethyl-piperazin-2-yl)ethanol.

(S)-3,4-[N,N'-1,1'-((2"-ethoxy)-3'''-(O)-4'''-(N,N-dimethylamino)-butane)-bis-(3,3'-indolyl)]-1(H)-pyrrole-2,5-dione or one of its salts 3-(1.H.-indol-3-yl)-4-[2-(4-methyl-piperazin-1-yl)-quinazolin-4-yl]-pyrrole-2,5-dione, 3-(1.H.-indol-3-yl)-4-[2-(piperazin-1-yl)-quinazolin-4-yl]-pyrrole-2,5-dione, 3-[3-(4,7-Diaza-spiro[2.5]oct-7-yl)-isoquinolin-1-yl]-4-(7-methyl-1H-indol-3-yl)-pyrrole-2,5-dione or a pharmaceutically acceptable salt thereof Peptide inhibitors of PKCβ can also be used on the methods, compositions and kits as disclosed herein, for example, peptide inhibitors as disclosed in U.S. Pat. No. 7,939,493 which is incorporated herein in its entirety by reference.

In some embodiments, an inhibitor is an inhibitor of a PKCβ, e.g., β1 or β2, γ, δ, or other isoform, or combinations thereof. The inhibitor can be, for example, a bis (indolyl) maleimide, for example, the PKCβ inhibitor LY333531.

Other inhibitors of PKCβ are encompassed for use in the methods, compositions and kits of the present invention, and are disclosed in U.S. Pat. Nos. 6,753,341; 6,232,299, patent applications 2011/0245256, 2011/0039770, 2011/0251203, 2008/0312241 each of which are incorporated herein in their entirety by reference.

A PKC inhibitor can be assessed using a method and screen to assess the antagonist activity of a PKC inhibitor activity of a compound according to the methods as disclosed in U.S. Pat. No. 5,776,685, which is incorporated herein in its entirety by reference.

Antibodies to PKCβ, e.g., neutralizing antibodies to PKCβ are also encompassed in the methods of the present invention.

Protein kinase C-associated kinase PKK (also known as DIK and RIP4) was initially identified as a protein kinase C β- and δ-interacting protein (Bahr et al., "DIK, a Novel Protein Kinase that Interacts with Protein Kinase Cdelta. Cloning, Characterization, and Gene Analysis," *J Biol Chem* 36350-36357 (2000); Chen et al., "Protein Kinase C-associated Kinase (PKK), a Novel Membrane-associated, Ankyrin Repeat-containing Protein Kinase,"*J Biol Chem* 276:21737-21744 (2001)). It belongs to the RIP kinase family, and shares high sequence homology at the N-terminal kinase domain with other members of this kinase family but contains unique C-terminal ankryin repeats (Meylan et al., "The RIP Kinases: Crucial Integrators of Cellular Stress," *Trends Biochem Sci* 30:151-159 (2005)). Mice deficient in PKK die soon after birth, likely due to suffocation caused by abnormal epidermal differentiation (Holland et al., "RIP4 is an Ankyrin Repeat-containing Kinase Essential for Keratinocyte Differentiation," *Curr Biol* 12:1424-1428 (2002)). It has been shown that PKK activates NF-κB when overexpressed in non-lymphoid cells (Moran et al., "Protein Kinase C-associated Kinase can Activate NFκB in Both a Kinase-dependent and a Kinase-independent Manner," *J Biol Chem* 278:21526-21533 (2003); Meylan et al., "RIP4 (DIK/PKK), a Novel Member of the RIP Kinase Family, Activates NF-κB and is Processed During Apoptosis," *EMBO Rep* 3:1201-1208 (2002); Muto et al., "Protein Kinase C-associated Kinase (PKK) Mediates Bcl10-independent NF-κB Activation Induced by Phorbol Ester," *J Biol Chem* 277:31871-31876 (2002)).

PKCβ Inhibitors

In some embodiments, the method comprises contacting a pancreatic progenitor cell with a PKC inhibitor compound, or a PKC β inhibitor compound, or a derivative, analogue or variant of the compound as follows:

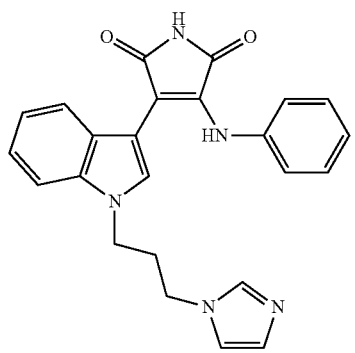 [SMILES: O=C1NC(=O)C(c2cn(CCCn3ccnc3)c3ccccc23)=C1Nc1ccccc1]

In some embodiments, the method comprises contacting a pancreatic progenitor cell with a GSK-2 inhibitor compound or a derivative, analogue or variant of the compound as follows:

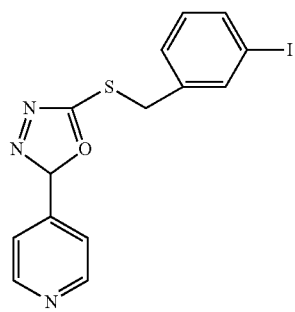

Bisindolylmaleimides

In some embodiments, the method comprises contacting a pancreatic progenitor cell with a bisindolylmaleimide compound, such as for example, but not limited to bisindolylmaleimide I, bisindolylmaleimide II, bisindolylmaleimide III, hydrochloride, or a derivative, analogue or variant of any of the compounds as follows:

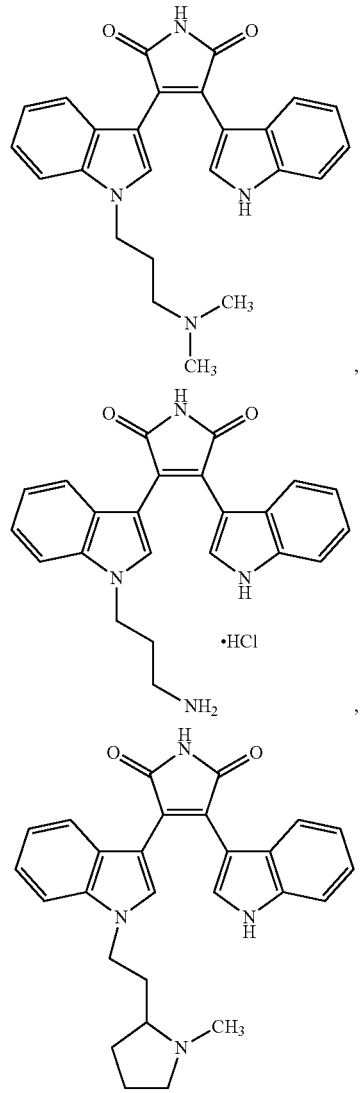

In some embodiments, the method comprises contacting a pancreatic progenitor cell with pseudohypericin or a derivative, analogue or variant of the compound as follows:

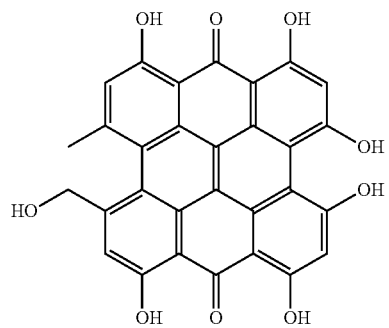 [SMILES: Cc1cc(O)c2c(=O)c3c(O)cc(O)c4c5c(O)cc(O)c6c(=O)c7c(O)cc(CO)c8c1c2c(c34)c(c65)c78]

In some embodiments, the method comprises contacting a pancreatic progenitor cell with a indorublin-3-monoxime, 5-Iodo or a derivative, analogue or variant of the following compound:

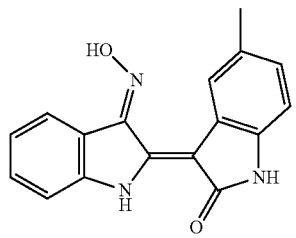 [SMILES: Cc1ccc2c(c1)/C(=C1/Nc3ccccc3/C1=N\O)C(=O)N2]

Another aspect relates to methods and compositions for the efficient differentiation of pancreatic progenitor cells, such as Pdx1+ pancreatic progenitors into endocrine cells, which express Ngn3. In some embodiments, the method comprises contacting a pancreatic progenitor cell with a PKC inhibitor, such as a PKCβ inhibitor as disclosed herein, such as GSK-3 inhibitor, or a bisindolylmaleimide compound as disclosed herein, or any compound of formula (I)-(V) or an analogue or derivative thereof to induce the differentiation of the pancreatic progenitor cells to endocrine progenitor cells which are Ngn3+. In some embodiments, the Ngn3+ endocrine cell can spontaneously differentiate into a glucose-responding β-cell, which expresses insulin.

Accordingly, the present invention provides a step-wise differentiation of preparing pancreatic progenitor cells that are β-cell like from Pdx1+ pancreatic progenitor cells.

In some embodiments of this aspect of the present invention provides methods of producing an insulin positive beta cell by contacting (e.g., culturing) a Pdx+ progenitor stem cell, with a compound as described herein, wherein the a pluripotent stem cell is contacted with a compound as disclosed herein at a concentration of about between 25 nM to 10 µM, or between about 25 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 5 µm, or about 5 µM to 10 µM.

In some embodiments, methods of producing a insulin positive beta cell by contacting (e.g., culturing) a Pdx+ progenitor cell with a compound as disclosed herein at a concentration of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM. In some embodiments, a pluripotent stem cell is contacted (e.g. cultured) with a compound as disclosed herein at a concentration of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM.

In some embodiments, a Pdx+ progenitor is contacted (e.g. cultured) with a compound of as disclosed herein at a concentration of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-100 nM, or any integer between 50-150 nM, or any integer between 100 nM-200 nM or any integer between 200 nM-500 nM. In some embodiments, the Pdx+ progenitor cell is contacted with a compound as disclosed herein at a concentration of about 100 nM to differentiate the Pdx+ progenitor cell into an insulin positive beta-cell.

In some embodiments, a Pdx+ progenitor cell is contacted (e.g. cultured) with a compound as disclosed herein, such that the Pdx+ progenitor cell is differentiated into a beta-cell which is insulin positive by contacting (e.g. culturing) the pluripotent stem cell with a compound as disclosed herein at a concentration of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-200 nM, or any integer between 100-300 nM, or any integer between 100 nM-500 nM or any integer between about 200 nM-500 nM. In some embodiments, the Pdx+ progenitor cell is contacted with a compound as disclosed herein at a concentration of about 200 nM to differentiate the Pdx+ progenitor cell into an insulin positive beta cell.

In some embodiments, a population of Pdx+ progenitor cell can be contacted or exposed to one or more of the compounds as described herein alone, and in other embodiments, a population of Pdx+ progenitor cell can be contacted with at least one additional agent, either concurrent with (e.g. in combination with), subsequent to or prior to the contact of the pluripotent cell with a compound as disclosed herein. In some embodiments, the additional compound for use in combination with compounds as disclosed herein can include, but is not limited to agents of transforming growth factor-β (TGF-β) family member (e.g., Nodal or Activin A), fibroblast growth factor (FGF) family member (e.g., FGF10), Wnt growth factor family member (e.g., Wnt3a), bone morphogenic proteins (BMPs) and/or members of the AKT/PI3K pathway. The definition and details of the TGF-β/BMP pathway are disclosed in the art e.g., Kawabata M. and Miyazono K., J. Biochem. (Tokyo), 125, 9-16 (1999); Wrana J. L., Miner. Electrolyte Metab., 24, 120-130 (1998); and Markowitz S. D., and Roberts A. B., Cytokine Growth Factor Rev., 7, 93-102 (1996). In some embodiments, a Pdx+ progenitor cell can be exposed to a compound as disclosed herein in combination with at least one additional compounds or factors including, but not limited to cyclopamine, TGF family members (TGF-alpha., Activin A, Activin B, TGF-beta-1, TGF-beta-3), exendin 4, nicotinamide, n-butyrate, DMSO, all-trans retinoic acid, GLP-I, bone morphogenic proteins (BMP-2, BMP-5, BMP-6, BMP-7), insulin-like growth factors (IGF-I, IGF-II), fibroblast growth factor (FGF7, FGF10, bFGF, FGF4), other growth factors (EGF, βcellulin, growth hormone, HGF), other hormones (prolactin, cholecytokinin, gastrin I, placental lactogen), TGF-β. family antagonists (Noggin, follistatin, chordin), IBMX, wortmannin, dexamethazone, Reg, INGAP, cAMP or cAMP activators (forskolin), and/or extracellular matrix components (laminin, fibronectin).

In certain examples, the agents such as compounds as disclosed herein can be used to induce the differentiation of Pdx+ progenitor cell into beta cells, e.g., insulin positive beta cells by exposing or contacting a population of pluripotent stem cells with an effective amount of at least one compound as described herein to differentiate the Pdx+ progenitor cell into a beta cell. Accordingly, included herein are cells and compositions made by the methods described herein. The exact amount and type of compound of as disclosed hereincan vary depending on the number of Pdx+ progenitor cells, the desired differentiation stage and the number of prior differentiation stages that have been performed.

In certain examples, a compound us used in an effective amount. As used herein, "effective amount" refers to the amount of the compound that should be present for the differentiation of at least 10% or at least 20% or at least 30% of the Pdx+ progenitor cells in a population of Pdx+ progenitor cells into beta cells, such as beta insulin-positive cells. In additional examples, a compound as disclosed herein can be present in the culture medium of the Pdx+ progenitor cells, or alternatively, the compounds as disclosed herein may be added to the Pdx+ progenitor cell during some stage of growth. In some examples, a compound as disclosed herein is used to produce the beta cells can be present in a concentration of about 10 µM/liter or less, for example about 1 µM/liter or less. In certain examples, a population of Pdx+ progenitor cells can be exposed to at least one compound as disclosed herein prior to any differentiation or during the first stage of differentiation.

Endoderm is one of the germ layers formed during animal embryogenesis. Cells generally migrate inward along the archenteron from the inner layer of the gastrula, which develops into the endoderm. Exemplary products produced by the endoderm include: gastrointestinal tract, respiratory tract, endocrine glands and organs (e.g., liver and pancreas). The endoderm generally consists at first of flattened cells, which subsequently become columnar. It can form the epithelial lining of the whole of the digestive tube except part of the mouth, pharynx and the terminal part of the rectum (which are lined by involutions of the ectoderm), the lining cells of all the glands which open into the digestive tube, including those of the liver and pancreas, the epithelium of the auditory tube and tympanic cavity, of the trachea, bronchi, and alveoli of the lungs, of the urinary bladder and part of the urethra, and that which lines the follicles of the thyroid gland and thymus.

Exemplary studies of the developmental pathways that control endoderm formation have been conducted in *Xenopous laevis*, zebrafish and mice (reviewed by Wells and Melton, 1999; Lewis and Tam, 2006). Collectively, these studies suggest a conserved mechanism for endoderm/mesoderm commitment utilizing the transforming growth factor-β (TGF-β) family member Activin A and Nodal, fibroblast growth factor (FGF) and Wnt growth factor families. Similarly, in vitro application of Activin A or Nodal to mouse or human ES cell cultures leads to endoderm induction (Kubo et al., 2004; Yasunaga et al., 2005; D'Amour et al., 2005). Other molecules that influence endoderm formation in vitro include WNTs (D'Amour et al., 2005), bone morphogenic proteins (BMPs), and members of the AKT/P13K pathway (McLean et al., 2007).

In certain examples, a method of inducing the differentiation of Pdx+ progenitor cells, is provided.

Confirmation of the Presence and the Identification of Pancreatic Beta Cells

One can use any means common to one of ordinary skill in the art to confirm the presence of a beta cell produced the induction of the differentiation of a Pdx+ progenitor cell by exposure to a compound as disclosed herein. In some embodiments, the presence of endoderm cells can be detected using suitable markers such as those listed in U.S. Pat. No. 7,326,572, which is incorporated herein by reference.

The progression of a Pdx+ progenitor cell to a beta cell can be monitored by determining the expression of markers characteristic of beta cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of pancreatic beta cells as well as the lack of significant expression of markers characteristic of the Pdx+ progenitor cell from which it was derived is determined.

As described in connection with monitoring the production of a pancreatic beta cell from a Pdx+ progenitor cell, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. Additionally, it will be appreciated that at the polypeptide level, many of the markers of pancreatic islet hormone-expressing cells are secreted proteins, such as insulin secretion. As such, techniques for measuring extracellular marker content, such as ELISA, may be utilized.

It is understood that the present invention is not limited to those markers listed as definitive endoderm markers herein, and the present invention also encompasses markers such as cell surface markers, antigens, and other gene products including ESTs, RNA (including microRNAs and antisense RNA), DNA (including genes and cDNAs), and portions thereof. Markers of definitive endoderm can be used, for example where a definitive endoderm cell expresses at least one marker from an endoderm cell. Markers of endoderm cells (which are distinct from definitive endoderm cells) include, Gata4, FoxA2, PDX1, Nodal, Sox7 and Sox17. By way of completeness, markers of mesoderm cells include, Brachycury, GSC, LEF1, Mox1 and Tie1. Markers of ectoderm cells include cripto1, EN1, GFAP, Islet 1, LIM1 and Nestin. Antibodies to markers of the three germ layers are commercially available, such as available from Abeam and other commercial antibody companies.

In some embodiments, a population of pancreatic beta cells can be replated or otherwise manipulated to begin another stage of differentiation. In certain circumstances, differentiation or maintenance of cells may be enhanced if the cells are kept in micromass clusters (for example, 50 to 5,000 cells), so that alpha, beta, and delta cells can interact directly.

Enrichment and Isolation and Purification of a Pancreatic Beta Cell

Another aspect of the present invention relates to the isolation of a population of pancreatic beta cells from a heterogeneous population of cells, such a mixed population of cells comprising Pdx+ progenitor cells from which the beta cells were derived. A population of beta cells produced by any of the above-described processes can be enriched, isolated and/or purified by using any cell surface marker present on the pancreatic beta cells which is not present on the Pdx+ progenitor cells from which it was derived. Such cell surface markers are also referred to as an affinity tag which is specific for a beta cells. Examples of affinity tags specific for beta cells are antibodies, ligands or other binding agents that are specific to a marker molecule, such as a polypeptide, that is present on the cell surface of a beta cell but which is not substantially present on other cell types (e.g. on Pdx+ progenitor cells). In some processes, an antibody which binds to a cell surface antigen on a beta cell is used as an affinity tag for the enrichment, isolation or purification of chemically induced (e.g. by contacting with a compound as disclosed herein) Pdx+ progenitor cells produced by the methods described herein. Such antibodies are known and commercially available.

The skilled artisan will readily appreciate that the processes for making and using antibodies for the enrichment, isolation and/or purification of pancreatic beta cells are also readily adaptable for the enrichment, isolation and/or purification of pancreatic beta cells. For example, in some embodiments, the reagent, such as an antibody, is incubated with a cell population comprising pancreatic beta cells, wherein the cell population has been treated to reduce intercellular and substrate adhesion. The cell population are then washed, centrifuged and resuspended. In some embodiments, if the antibody is not already labeled with a label, the cell suspension is then incubated with a secondary antibody, such as an FITC-conjugated antibody that is capable of binding to the primary antibody. The pancreatic beta cells are then washed, centrifuged and resuspended in buffer. The pancreatic beta cells suspension is then analyzed and sorted using a fluorescence activated cell sorter (FACS). Antibody-bound, fluorescent reprogrammed cells are collected separately from non-bound, non-fluorescent cells (e.g. non-definitive endoderm cells), thereby resulting in the isolation of pancreatic beta cells from Pdx+ pancreatic progenitors.

In another embodiments of the processes described herein, the isolated cell composition comprising pancreatic beta cells can be further purified by using an alternate affinity-based method or by additional rounds of sorting using the same or different markers that are specific for pancreatic beta cells. For example, in some embodiments, FACS sorting is used to first isolate a pancreatic beta cell which expresses beta cell markers from cells that do not express one of those markers (e.g. negative cells) in the cell population. A second FAC sorting, e.g. sorting the positive cells again using FACS to isolate cells that are positive for a different marker than the first sort enriches the cell population for pancreatic beta cells.

In an alternative embodiment, FACS sorting is used to separate cells by negatively sorting for a marker that is present on most Pdx+ pancreatic progenitor cells, or a marker which not present on the pancreatic beta cells.

In some embodiments of the processes described herein, pancreatic beta cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above. For example, in some embodiments, at least one copy of a nucleic acid encoding GFP or a biologically active fragment thereof is introduced into a pluripotent stem cell which is to be chemically induced into a pancreatic beta cell, where a downstream of a promoter expressed in a pancreatic beta cell, such as the insulin promoter, such that the expression of the GFP gene product or biologically active fragment thereof is under control of the insulin promoter. In some embodiments, the entire coding region of the nucleic acid, which encodes insulin is replaced by a nucleic acid encoding GFP or a biologically active fragment thereof. In other embodiments, the nucleic acid encoding GFP or a biologically active fragment thereof is fused in frame with at least a portion of the nucleic acid encoding insulin, thereby generating a fusion protein. In such embodiments, the fusion protein retains a fluorescent activity similar to GFP.

In addition to the procedures just described, chemically induced pancreatic beta cells may also be isolated by other techniques for cell isolation. Additionally, pancreatic beta cells may also be enriched or isolated by methods of serial subculture in growth conditions which promote the selective survival or selective expansion of the pancreatic beta cells. Such methods are known by persons of ordinary skill in the art.

Using the methods described herein, enriched, isolated and/or purified populations of pancreatic beta cells can be produced in vitro from pluripotent stem cells. Some preferred enrichment, isolation and/or purification methods relate to the in vitro production of human pancreatic beta cells from Pdx+ progenitor cells. In such an embodiment, where pancreatic beta cells are derived from Pdx+ progenitor cells which have been differentiated from iPS cells, the pancreatic beta cells can be autologous to the subject from whom the cells were obtained to generate the initial iPS cells.

Using the methods described herein, isolated cell populations of pancreatic beta cells are enriched in pancreatic beta cells content by at least about 2- to about 1000-fold as compared to a population of cells before the chemical induction. In some embodiments, pancreatic beta cells can be enriched by at least about 5- to about 500-fold as compared to a population before the chemical induction of the Pdx+ progenitor cell population. In other embodiments, pancreatic beta cells can be enriched from at least about 10- to about 200-fold as compared to a population before the chemical induction. In still other embodiments, pancreatic beta cells can be enriched from at least about 20- to about 100-fold as compared to a population before the chemical induction of the Pdx+ progenitor cell population. In yet other embodiments, pancreatic beta cells can be enriched from at least about 40- to about 80-fold as compared to a population before the chemical induction of the Pdx+ progenitor cell population. In certain embodiments, pancreatic beta cells can be enriched from at least about 2- to about 20-fold as compared to a population before the chemical induction of the Pdx+ progenitor cell population.

Compositions Comprising Definitive Endoderm Cells

Some embodiments of the present invention relate to cell compositions, such as cell cultures or cell populations, comprising pancreatic beta cells, wherein the definitive endoderm cells which have been derived from Pdx+ pancreatic progenitor cells. In accordance with certain embodiments, the chemically induced pancreatic beta cells are mammalian cells, and in a preferred embodiment, such pancreatic beta cells are human pancreatic beta cells.

Other embodiments of the present invention relate to compositions, such as an isolated cell population or cell culture, comprising pancreatic beta cells produced by the methods as disclosed herein. In some embodiments of the present invention relate to compositions, such as isolated cell populations or cell cultures, comprising chemically-induced pancreatic beta cells produced by the methods as disclosed herein. In such embodiments, the pancreatic beta cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the pancreatic beta cells. In some embodiments, the composition comprises a population of pancreatic beta cell which make up more than about 90% of the total cells in the cell population, for example about at least 95%, or at least 96%, or at least 97%, or at least 98% or at least about 99%, or about at least 100% of the total cells in the cell population are pancreatic beta cells.

Certain other embodiments of the present invention relate to compositions, such as an isolated cell population or cell cultures, comprise a combination of pancreatic beta cells and the Pdx+ progenitor from which the pancreatic beta cells were derived. In some embodiments, the Pdx+ pancreatic progenitor cells from which the pancreatic beta cells are derived comprise less than about 25%, less than about 20%, less than about 15%, less than about 10%, less than about 5%, less than about 4%, less than about 3%, less than about 2% or less than about 1% of the total cells in the isolated cell population or culture.

Additional embodiments of the present invention relate to compositions, such as isolated cell populations or cell cultures, produced by the processes described herein and which comprise chemically induced pancreatic beta cells as the majority cell type. In some embodiments, the methods and processes described herein produces an isolated cell culture and/or cell populations comprising at least about 99%, at least about 98%, at least about 97%, at least about 96%, at least about 95%, at least about 94%, at least about 93%, at least about 92%, at least about 91%, at least about 90%, at least about 89%, at least about 88%, at least about 87%, at least about 86%, at least about 85%, at least about 84%, at least about 83%, at least about 82%, at least about 81%, at least about 80%, at least about 79%, at least about 78%, at least about 77%, at least about 76%, at least about 75%, at least about 74%, at least about 73%, at least about 72%, at least about 71%, at least about 70%, at least about 69%, at least about 68%, at least about 67%, at least about 66%, at least about 65%, at least about 64%, at least about 63%, at least about 62%, at least about 61%, at least about 60%, at least about 59%, at least about 58%, at least about 57%, at least about 56%, at least about 55%, at least about 54%, at least about 53%, at least about 52%, at least about 51% or at least about 50% pancreatic beta cells.

In another embodiment, isolated cell populations or compositions of cells (or cell cultures) comprise human pancreatic beta cells. In other embodiments, the methods and processes as described herein can produce isolated cell populations comprising at least about 50%, at least about 45%, at least about 40%, at least about 35%, at least about 30%, at least about 25%, at least about 24%, at least about 23%, at least about 22%, at least about 21%, at least about 20%, at least about 19%, at least about 18%, at least about 17%, at least about 16%, at least about 15%, at least about 14%, at least about 13%, at least about 12%, at least about IT %, at least about 10%, at least about 9%, at least about 8%, at least about 7%, at least about 6%, at least about 5%, at least about 4%, at least about 3%, at least about 2% or at least about 1% pancreatic beta cells. In preferred embodiments, isolated cell populations can comprise human pancreatic beta cells. In some embodiments, the percentage of pancreatic beta cells in the cell cultures or populations is calculated without regard to the feeder cells remaining in the culture.

Still other embodiments of the present invention relate to compositions, such as isolated cell populations or cell cultures, comprising mixtures of pancreatic beta cells and Pdx+ progenitor cells. For example, cell cultures or cell populations comprising at least about 5 pancreatic beta cells for about every 95 Pdx+ progenitor cells can be produced. In other embodiments, cell cultures or cell populations comprising at least about 95 pancreatic beta cells cells for about every 5 Pdx+ progenitor cells can be produced. Additionally, cell cultures or cell populations comprising other ratios of pancreatic beta cells to Pdx+ progenitor cells are contemplated. For example, compositions comprising at least about 1 pancreatic progenitor cell for about every 1,000,000, or at least 100,000 cells, or a least 10,000 cells, or at least 1000 cells or 500, or at least 250 or at least 100 or at least 10 Pdx+ progenitor cell can be produced.

Further embodiments of the present invention relate to compositions, such as cell cultures or cell populations, comprising human cells, including human pancreatic beta cells which express insulin and one or two or at least 3 or more characteristics of a cell of a pancreatic beta cell.

In preferred embodiments of the present invention, cell cultures and/or cell populations of pancreatic beta cells comprise human pancreatic beta cells, that are non-recombinant cells. In such embodiments, the cell cultures and/or cell populations are devoid of or substantially free of recombinant human pancreatic beta cells.

Use of the Pancreatic Beta Cells

Another aspect relates to the use of the pancreatic beta cells produced by the methods as disclosed herein for subsequent differentiating into other cell types. In some embodiments, a pancreatic beta cell produced by a method described herein, is differentiated to a cell of a second cell type (e.g., a differentiated cell). Included herein are cells and compositions made by the methods described herein. Exemplary second cell types include those cells which are derived from endoderm such as liver, lung, stomach, intestine, and thymus as well as the pancreas. For example, in some embodiments, pancreatic beta cells may be differentiated into liver endoderm cells by contacting the definitive endoderm cell with about 10 ng/ml-100 ng/ml (preferably, about 50 ng/ml) of FGF10.

In some embodiments, a pancreatic beta cell produced by a method described herein, is differentiated into a pancreatic cell, such as, for example, pancreatic endocrine cells (alpha cells, β-cells, delta cells, Pdx1-positive pancreatic progenitors (also referred to herein as "PP" cells) and the like) or a pancreatic exocrine cell.

In certain embodiments, the pancreatic beta cells produced by the methods as disclosed herein are produced from the human or mouse Pdx1-positive progenitors, and are insulin-producing cells.

In accordance with certain examples, step-wise differentiation may be implemented to differentiate stem cells to a desired cell, such as a pancreatic cell. One method of step-wise differentiation is described in U.S. Pat. No. 7,326,572, which is incorporated herein in its entirety by reference.

In some examples, Pdx1-positive progenitors can be contacted with a compound as disclosed herein in combination with other compounds, such as, for example but not limited to, the terminal differentiation factor nicotinamide (in the presence of cyclopamine and activin A). In other examples, one or more additional stages of differentiation may be implemented. For example, it may be desirable to further differentiate or mature of the pancreatic cells into a desired cell type.

In certain examples, the desired number of stages for producing pancreatic cell types may be based, at least in part, on the intended use of the end-stage cell populations. For example, it may be desirable to produce beta cell precursors for therapy for treating metabolic disorders. In other examples, it may be desirable to further differentiate the Pdx1-positive pancreatic progenitors into insulin-producing cells or pancreatic β-cells or pancreatic β-like cells for use in treating diabetes.

Another embodiments relate to the use of a pancreatic beta cells for transplanting into a subject in need thereof, where the definitive endoderm cell differentiates in vivo into a insulin-producing cell such as a pancreatic β-cell or pancreatic β-like cell.

Another aspect relates to the use of the pancreatic beta cells produced by the methods as disclosed herein for producing into insulin-producing cells, such as pancreatic β-cells or pancreatic β-like cells.

Another embodiments relate to the use of a pancreatic beta cells as produced by the methods and compositions as disclosed herein for transplanting into a subject in need thereof, where a pancreatic beta cells can spontaneously differentiate in vivo into a insulin-producing cell such as a pancreatic β-cell or pancreatic β-like cells.

Pancreatic Beta Cells Progenitor Produced from Pdx+ Pancreatic Progenitor Cells

One can use any means common to one of ordinary skill in the art to confirm the presence of a pancreatic beta cells produced the induction of the differentiation of a Pdx+ progenitor cell as disclosed herein by exposure to the compounds as disclosed herein.

In preferred embodiments of the present invention, cell cultures and/or cell populations of pancreatic beta cells comprise human pancreatic beta cells that are non-recombinant cells. In such embodiments, the cell cultures and/or cell populations are devoid of or substantially free of recombinant human Pdx1-positive pancreatic progenitor cells.

Admixture Compositions.

Another aspect of the present invention relates to an admixture of pancreatic beta cells and at least one compound as disclosed herein for inducing the differentiation of Pdx+ progenitor cells to become pancreatic beta cells.

In another aspect of the present invention relates to composition, such as a reaction admixture comprising a pdx+ progenitor cell and at least one compound as disclosed herein. Alternatively, the present invention relates to a reaction admixture comprising (i) a population of pancreatic beta cells produced by chemical induction of differentiation of a Pdx+ progenitor cell to a pancreatic beta cell, and (ii) at least one compound as disclosed herein.

In some embodiments, the concentrations of a compound as disclosed herein added to the reaction mixture is a sufficient dose for inducing a Pdx+ progenitor cell to differentiate into a pancreatic beta cell, as described herein.

In some embodiments, the composition comprises a concentration of a compound of as disclosed herein of about between 25 nM to 10 µM, or between about 25 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 5 µm, or about 5 µM to 10 µM.

In some embodiments, a composition or admixture comprises a concentration of a compound as disclosed herein of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM. In some embodiments, a composition or admixture comprises a concentration of a compound as disclosed herein of at least about 0.1 µM, or at least about 0.2 µM, or at least about 0.3 µM, or at least about 0.4 µM, or at least about 0.5 µM, or at least about 1 µM, at least about 1.5 µM, at least about 2 µM, at least about 2.5 µM, at least about 3 µM, at least about 3.5 µM, at least about 4 µM, at least about 4.5 µM, at least about 5 µM, at least about 6 µM, at least about 7 µM, at least about 8 µM, at least about 9 µM, or at least about 10 µM, or more than 10 µM, or any inter between 0.1-0.5 µM or any integer between about 0.5-10 µM or any inter between 0.1-10 µM, or any integer between 0.5-5 µM, or any integer between 5 µM-10 µM.

In some embodiments, a composition or admixture comprises a concentration of a compound as disclosed herein of at least about at least about 20 nM, or at least about 25 nM, at least about 30 nM, at least about 35 nM, at least about 40 nM, at least about 45 nM, at least about 50 nM, or at least about 60 nM, or at least about 70 nM, or at least about 80 nM, or at least about 90 nM, or at least about 100 nM or at least about 200 nM, or at least about 300 nM or at least about 400 nM or at least about 500 nM or more than 500 nM, or any inter between 20-500 nM or any inter between 50-100 nM, or any integer between 50-150 nM, or any integer between 100 nM-200 nM or any integer between 200 nM-500 nM.

Another aspect of the present invention relates to an admixture of Pdx1-positive pancreatic progenitor cells and at least one compound as disclosed herein, for inducing the differentiation of a Pdx+ progenitor cells to become a pancreatic beta cell.

In another aspect of the present invention relates to composition, such as a reaction admixture comprising a pancreatic beta cells (e.g. produced by differentiation of a Pdx+ progenitor cell by the methods as disclosed herein) and at least one compound as disclosed herein.

In some embodiments, the concentrations of a compound as disclosed herein added to the reaction mixture is a sufficient dose for inducing a pancreatic beta cell to differentiate from a Pdx1 progenitor as described herein.

In some embodiments, the composition comprises a concentration of a compound of as disclosed herein of about between 20 nM to 5 µM, or between about 20 nM to 50 nM, or about 50 nM to 100 nM, or about 100 nM to 200 nM, or about 200 nM to about 500 nM or about 500 nM to about 1 µM, or about 1 µM to 2 µm, or about 2 µM to 4 µm, or about 2 µM to 5 µM.

In some embodiments, a composition or admixture comprises a concentration of a compound as disclosed herein of at least about 5 nM, at least about 7 nM, at least about 10 nM, at least about 12 nM, at least about 15 nM, at least about 17 nM, at least about 20 nM, at least about 25 nM, at least about 30 nM, at least about 35 nM, at least about 40 nM, at least about 45 nM, at least about 50 nM, at least about 100 nM or at least about 200 nM, or at least about 300 nM or at least about 400 nM or at least about 500 nM or more than 500 nM, or any inter between 10-500 nM or any inter between 5-50 nM, or any integer between 50-100 nM, or any integer between 100 nM-200 nM or any integer between 200 nM-500 nM.

Compositions and Kits

Described herein are compositions which comprise a cell described herein (e.g., a pancreatic beta cell or a Pdx1-positive progenitor cell). In some embodiments, the composition also includes a compound described herein and/or cell culture media. Described herein are also compositions comprising the compounds described herein (e.g. cell culture media comprising one or more of the compounds described herein). Described herein are kits.

Another aspect of the present invention relates to kits for practicing methods disclosed herein and for making pancreatic beta cells disclosed herein. In one aspect, a kit includes a Pdx+ progenitor cell and a compound as described herein, and optionally, the kit can further comprise instructions for converting a population of Pdx+ progenitor cell to a population of pancreatic beta cells using a method described herein.

In one embodiment, the kit can comprise a pancreatic beta cell for the purposes of being used as a positive control, for example to assess or monitor the effectiveness or ability of a compound as disclosed herein to chemically induce the Pdx+ progenitor cell to differentiate into a beta cell. Accordingly, the kit can comprise sufficient amount of a compound as disclosed herein for inducing the differentiation of a control Pdx+ progenitor cell population (positive control) into a population of pancreatic beta cells.

In some embodiment, the compound in the kit can be provided in a watertight or gas tight container which in some embodiments is substantially free of other components of the kit. The compound can be supplied in more than one container, e.g., it can be supplied in a container having sufficient reagent for a predetermined number of reactions e.g., 1, 2, 3 or greater number of separate reactions to induce pluripotent stem cells to pancreatic beta cells, and subsequently into pancreatic beta cells. A compound(s) described herein can be provided in any form, e.g., liquid, dried or lyophilized form. It is preferred that a compound(s) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

In some embodiments, the kit further optionally comprises information material. The informational material can be descriptive, instructional, marketing or other material that relates to the methods described herein and/or the use of a compound(s) described herein for the methods described herein.

The informational material of the kits is not limited in its instruction or informative material. In one embodiment, the informational material can include information about production of the compound, molecular weight of the compound, concentration, date of expiration, batch or production site information, and so forth. In one embodiment, the informational material relates to methods for administering the compound. Additionally, the informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In one embodiment, the informational material can include instructions to administer a compound(s) as described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or an additional agent, e.g., for inducing pluripotent stem cells (e.g., in vitro) or for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

A compound as described herein can be provided in any form, e.g., liquid, dried or lyophilized form. It is preferred that a compound(s) described herein be substantially pure and/or sterile. When a compound(s) d described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

The kit can include one or more containers for the composition containing at least one compound as described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The kit can also include a component for the detection of a marker for pancreatic beta cells. Or in some embodiments, the kit can also comprise reagents for the detection of negative markers of pancreatic beta cells, e.g. Gata4, SPARC, APF, DAB, Zic, Pax6, Flk1 or CD31 for the purposes of negative selection of non-pancreatic beta cells or for identification of cells which do not express these negative markers (e.g. pancreatic beta cells). The reagents can be, for example, an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

It may be desirable to perform an analysis of the karyotype of the pancreatic beta cell or Pdx1-positive pancreatic progenitor cell. Accordingly, the kit can include a component for karyotyping, e.g., a probe, a dye, a substrate, an enzyme, an antibody or other useful reagents for preparing a karyotype from a cell.

The kit can include a pancreatic beta cell, from the same type of pdx+ progenitor cells cell, for example for the use as a positive cell type control. The kit can also include informational materials, e.g., instructions, for use of two or more of the components included in the kit.

The informational material can be descriptive, instructional, marketing or other material that relates to the methods described herein and/or the use of a compound(s) described herein for differentiating a pluripotent stem cell according to the methods described herein. In one embodiment, the informational material can include information about production of the compound, molecular weight of the compound, concentration, date of expiration, batch or production site information, and so forth. In one embodiment, the informational material relates to methods for culturing a population of pdx+ progenitor cells in the presence of a compound as disclosed herein and optionally, informational material relating to methods for culturing a population of pdx+ progenitor cells in the presence of a compound as disclosed herein.

Methods of Administering a Cell

In one embodiment, the cells described herein, e.g. a population of pancreatic beta cells are transplantable, e.g., a population of pancreatic beta cells and/or a population of Pdx1-positive pancreatic progenitor cells can be administered to a subject. In some embodiment, the subject who is administered a population of pancreatic beta cells is the same subject from whom a pdx+ progenitor cell used to differentiate into a pancreatic beta cell was obtained (e.g. for autologous cell therapy). In some embodiments, the subject is a different subject. In some embodiments, a subject suffering from diabetes such as type I diabetes, or is a normal subject. For example, the cells for transplantation (e.g. a composition comprising a population of pancreatic beta cells) can be a form suitable for transplantation, e.g., organ transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A composition comprising a population of pancreatic beta cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6): 563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Pharmaceutical Compositions Comprising a Population of Pancreatic Beta Cells.

For administration to a subject, a cell populations produced by the methods as disclosed herein, e.g. a population of pancreatic beta cells (produced by contacting a population of Pdx+ progenitor cells with a compound as disclosed herein) can be administered to a subject, for example in a pharmaceutically acceptable compositions. These pharmaceutically acceptable compositions comprise a therapeutically-effective amount of a population of pancreatic beta cells as described above, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The phrase "therapeutically-effective amount" as used herein in respect to a population of cells means that amount of relevant cells in a population of cells, e.g, pancreatic beta cells, or composition comprising a pancreatic beta cells and/or Pdx1-positive pancreatic progenitor cells of the present invention which is effective for producing some desired therapeutic effect in at least a sub-population of cells in an animal at a reasonable benefit/risk ratio applicable to any medical treatment. For example, an amount of a population of pancreatic beta cells administered to a subject that is sufficient to produce a statistically significant, measurable change in at least one symptom of Type 1, Type 1.5 or Type 2 diabetes, such as glycosylated hemoglobin level, fasting blood glucose level, hypoinsulinemia, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Treatment of Diabetes is determined by standard medical methods. A goal of Diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycosylated hemoglobin level (HbA1c; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with complications relating to Diabetes, such as diseases of the eye, kidney disease, or nerve disease.

Delaying the onset of diabetes in a subject refers to delay of onset of at least one symptom of diabetes, e.g., hyperglycemia, hypoinsulinemia, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, or combinations thereof, for at least 1 week, at least 2 weeks, at least 1 month, at least 2 months, at least 6 months, at least 1 year, at least 2 years, at least 5 years, at least 10 years, at least 20 years, at least 30 years, at least 40 years or more, and can include the entire lifespan of the subject.

In certain embodiments, the subject is a mammal, e.g., a primate, e.g., a human. The terms, "patient" and "subject" are used interchangeably herein. Preferably, the subject is a mammal. The mammal can be a human, non-human primate, mouse, rat, dog, cat, horse, or cow, but are not limited to these examples. Mammals other than humans can be advantageously used as subjects that represent animal models of Type 1 diabetes, Type 2 Diabetes Mellitus, or pre-diabetic conditions. In addition, the methods described herein can be used to treat domesticated animals and/or pets. A subject can be male or female. A subject can be one who has been previously diagnosed with or identified as suffering from or having Diabetes (e.g., Type 1 or Type 2), one or more complications related to Diabetes, or a pre-diabetic condition, and optionally, but need not have already undergone treatment for the Diabetes, the one or more complications related to Diabetes, or the pre-diabetic condition. A subject can also be one who is not suffering from Diabetes or a pre-diabetic condition. A subject can also be one who has been diagnosed with or identified as suffering from Diabetes, one or more complications related to Diabetes, or a pre-diabetic condition, but who show improvements in known Diabetes risk factors as a result of receiving one or more treatments for Diabetes, one or more complications related to Diabetes, or the pre-diabetic condition. Alternatively, a subject can also be one who has not been previously diagnosed as having Diabetes, one or more complications related to Diabetes, or a pre-diabetic condition. For example, a subject can be one who exhibits one or more risk factors for Diabetes, complications related to Diabetes, or a pre-diabetic condition, or a subject who does not exhibit Diabetes risk factors, or a subject who is asymptomatic for Diabetes, one or more Diabetes-related complications, or a pre-diabetic condition. A subject can also be one who is suffering from or at risk of developing Diabetes or a pre-diabetic condition. A subject can also be one who has been diagnosed with or identified as having one or more complications related to Diabetes or a pre-diabetic condition as defined herein, or alternatively, a subject can be one who has not been previously diagnosed with or identified as having one or more complications related to Diabetes or a pre-diabetic condition.

As used herein, the phrase "subject in need of Pdx1-positive pancreatic progenitor cells" refers to a subject who is diagnosed with or identified as suffering from, having or at risk for developing diabetes (e.g., Type 1, Type 1.5 or Type 2), one or more complications related to diabetes, or a pre-diabetic condition.

A subject in need of pancreatic beta cells, e.g., those produced from Pdx1-positive pancreatic progenitor cells by the methods and compositions as disclosed herein can be identified using any method used for diagnosis of diabetes. For example, Type 1 diabetes can be diagnosed using a glycosylated hemoglobin (A1C) test, a random blood glucose teat and/or a fasting blood glucose test. Parameters for diagnosis of diabetes are known in the art and available to skilled artisan without much effort.

In some embodiments, the methods of the invention further comprise selecting a subject identified as being in need of additional pancreatic beta cells. A subject in need of pancreatic beta cells can be selected based on the symptoms presented, such as symptoms of type 1, type 1.5 or type 2 diabetes. Exemplary symptoms of diabetes include, but are not limited to, excessive thirst (polydipsia), frequent urination (polyuria), extreme hunger (polyphagia), extreme fatigue, weight loss, hyperglycemia, low levels of insulin, high blood sugar (e.g., sugar levels over 250 mg, over 300 mg), presence of ketones present in urine, fatigue, dry and/or itchy skin, blurred vision, slow healing cuts or sores, more infections than usual, numbness and tingling in feet, diabetic retinopathy, diabetic nephropathy, blindness, memory loss, renal failure, cardiovascular disease (including coronary artery disease, peripheral artery disease, cerebrovascular disease, atherosclerosis, and hypertension), neuropathy, autonomic dysfunction, hyperglycemic hyperosmolar coma, and combinations thereof.

In some embodiments, a composition comprising a population of pancreatic beta cells (e.g., produced from Pdx1-positive progenitors) for administration to a subject can further comprise a pharmaceutically active agent, such as those agents known in the art for treatment of diabetes and or for having anti-hyperglycemic activities, for example, inhibitors of dipeptidyl peptidase 4 (DPP-4) (e.g., Alogliptin, Linagliptin, Saxagliptin, Sitagliptin, Vildagliptin, and Berberine), biguanides (e.g., Metformin, Buformin and Phenformin), peroxisome proliferator-activated receptor (PPAR) modulators such as thiazolidinediones (TZDs) (e.g., Pioglitazone, Rivoglitazone, Rosiglitazone and Troglitazone), dual PPAR agonists (e.g., Aleglitazar, Muraglitazar and Tesaglitazar), sulfonylureas (e.g., Acetohexamide, Carbutamide, Chlorpropamide, Gliclazide, Tolbutamide, Tolazamide, Glibenclamide (Glyburide), Glipizide, Gliquidone, Glyciopyramide, and Glimepiride), meglitinides ("glinides") (e.g., Nateglinide, Repaglinide and Mitiglinide), glucagon-like peptide-1 (GLP-1) and analogs (e.g., Exendin-4, Exenatide, Liraglutide, Albiglutide), insulin and insulin analogs (e.g., Insulin lispro, Insulin aspart, Insluin glulisine, Insulin glargine, Insulin detemir, Exubera and NPH insulin), alpha-glucosidase inhibitors (e.g., Acarbose, Miglitol and Voglibose), amylin analogs (e.g. Pramlintide), Sodium-dependent glucose cotransporter T2 (SGLT T2) inhibitors (e.g., Dapgliflozin, Remogliflozin and Sergliflozin) and others (e.g. Benfluorex and Tolrestat).

In type 1 diabetes, β-cells are undesirably destroyed by continued autoimmune response. This autoimmune response may also destroy pancreatic beta cells or Pdx1-positive pancreatic progenitor cells implanted into a subject. Thus, this autoimmune response can be attenuated by use of compounds that inhibit or block such an autoimmune response. In some embodiments, a composition comprising a population of pancreatic beta cells or Pdx1-positive progenitors for administration to a subject can further comprise a pharmaceutically active agent which is a immune response modulator. As used herein, the term "immune response modulator" refers to compound (e.g., a small-molecule, antibody, peptide, nucleic acid, or gene therapy reagent) that inhibits autoimmune response in a subject. Without wishing to be bound by theory, an immune response modulator inhibits the autoimmune response by inhibiting the activity, activation, or expression of inflammatory cytokines (e.g., IL-12, IL-23 or IL-27), or STAT-4. Exemplary immune response modulators include, bbut are not limited to, members of the group consisting of Lisofylline (LSF) and the LSF analogs and derivatives described in U.S. Pat. No. 6,774,130, contents of which are herein incorporated by reference in their entirety.

A composition comprising a pancreatic beta cells can be administrated to the subject in the same time, of different times as the administration of a composition comprising pancreatic beta cells (produced from Pdx1-positive pancreatic progenitors by the methods and compositions as disclosed herein). When administrated at different times, the compositions comprising a population of pancreatic beta cells and/or Pdx1-positive progenitors for administration to a subject can be administered within 5 minutes, 10 minutes, 20 minutes, 60 minutes, 2 hours, 3 hours, 4, hours, 8 hours, 12 hours, 24 hours of administration of the other. When a composition comprising a population of pancreatic beta cells and/or a composition comprising a population of Pdx1-positive progenitors are administered in different pharmaceutical compositions, routes of administration can be different. In some embodiments, a subject is administered a composition comprising pancreatic beta cells. In other embodiments, a subject is administered a composition comprising Pdx1-positive pancreatic progenitors. In another embodiment, a subject is administered a compositions comprising a population of pancreatic beta cells mixed with a population of Pdx1-positive progenitors. In another embodiment, a subject is administered a composition comprising a population of pancreatic beta cells and a composition comprising a population of Pdx1-positive progenitors, where administration is substantially at the same time, or subsequent to each other.

Toxicity and therapeutic efficacy of administration of a compositions comprising a population of pancreatic beta cells and/or Pdx1-positive progenitors can be determined by standard pharmaceutical procedures in cell cultures or experimental animals, e.g., for determining the LD50 (the dose lethal to 50% of the population) and the ED50 (the dose therapeutically effective in 50% of the population). Compositions comprising a population of pancreatic beta cells and/or Pdx1-positive progenitors that exhibit large therapeutic indices, are preferred.

The amount of a composition comprising a population of pancreatic beta cells and/or Pdx1-postitive progenitors can be tested using several well-established animal models.

The non-obese diabetic (NOD) mouse carries a genetic defect that results in insulitis showing at several weeks of age (Yoshida et al., Rev. Immunogenet. 2:140, 2000). 60-90% of the females develop overt diabetes by 20-30 weeks. The immune-related pathology appears to be similar to that in human Type I diabetes. Other models of Type I diabetes are mice with transgene and knockout mutations (Wong et al., Immunol. Rev. 169:93, 1999). A rat model for spontaneous Type I diabetes was recently reported by Lenzen et al. (Diabetologia 44:1189, 2001). Hyperglycemia can also be induced in mice (>500 mg glucose/dL) by way of a single intraperitoneal injection of streptozotocin (Soria et al., Diabetes 49:157, 2000), or by sequential low doses of streptozotocin (Ito et al., Environ. Toxicol. Pharmacol. 9:71, 2001). To test the efficacy of implanted islet cells, the mice are monitored for return of glucose to normal levels (<200 mg/dL).

Larger animals provide a good model for following the sequelae of chronic hyperglycemia: Dogs can be rendered insulin-dependent by removing the pancreas (J. Endocrinol. 158:49, 2001), or by feeding galactose (Kador et al., Arch. Opthalmol. 113:352, 1995). There is also an inherited model for Type I diabetes in keeshond dogs (Am. J. Pathol. 105:194, 1981). Early work with a dog model (Banting et al., Can. Med. Assoc. J. 22:141, 1922) resulted in a couple of Canadians making a long ocean journey to Stockholm in February of 1925.

By way of illustration, a pilot study can be conducted by implanting a population of pancreatic beta cells or a population of Pdx1-pancreatic progenitors (or both) into the following animals: a) non-diabetic nude (T-cell deficient) mice; b) nude mice rendered diabetic by streptozotocin treatment; and c) nude mice in the process of regenerating islets following partial pancreatectomy. The number of cells transplanted is equivalent to ~1000-2000 normal human β-cells implanted under the kidney capsule, in the liver, or in the pancreas. For non-diabetic mice, the endpoints of can be assessment of graft survival (histological examination) and determination of insulin production by biochemical analysis, RIA, ELISA, and immunohistochemistry. Streptozotocin treated and partially pancreatectomized animals can also be evaluated for survival, metabolic control (blood glucose) and weight gain.

In some embodiments, data obtained from the cell culture assays and in animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising a population of pancreatic beta cells can also be estimated initially from cell culture assays. A dose may be formulated in animal models in vivo to achieve a secretion of insulin at a concentration which is appropriate in response to circulating glucose in the plasma. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the polypeptides. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of the pancreatic beta cells as disclosed herein. In one embodiment of the invention, an isolated population of pancreatic beta cells as disclosed herein may be used for the production of a pharmaceutical composition, for the use in transplantation into subjects in need of treatment, e.g. a subject that has, or is at risk of developing diabetes, for example but not limited to subjects with congenital and acquired diabetes. In one embodiment, an isolated population of the pancreatic beta cells may be genetically modified. In another aspect, the subject may have or be at risk of diabetes and/or metabolic disorder. In some embodiments, an isolated population of the pancreatic beta cells as disclosed herein may be autologous and/or allogenic. In some embodiments, the subject is a mammal, and in other embodiments the mammal is a human.

The use of an isolated population of pancreatic beta cells as disclosed herein provides advantages over existing methods because the pancreatic beta cells can be differentiated from Pdx+ progenitor cells which are differentiated from stem cells, e.g. iPS cells obtained or harvested from the subject administered an isolated population of pancreatic beta cells. This is highly advantageous as it provides a renewable source of pancreatic beta cells with can be differentiated in vitro or in vivo to insulin-producing cells (e.g. pancreatic β-like cells or cells with pancreatic β-cell characteristics) by methods commonly known by one of ordinary skill in the art, for transplantation into a subject, in particular a substantially pure population of pancreatic beta cells that do not have the risks and limitations of cells derived from other systems.

In another embodiment, an isolated population of pancreatic beta cells can be used as models for studying properties for the differentiation into insulin-producing cells, e.g. to pancreatic β-cells or pancreatic β-like cells, or pathways of development of cells of endoderm origin into pancreatic β-cells.

In some embodiments, the pancreatic beta cells may be genetically engineered to comprise markers operatively linked to promoters that are expressed when a marker is expressed or secreted, for example, a marker can be operatively linked to an insulin promoter, so that the marker is expressed when the pancreatic beta cells are differentiated into insulin-producing cells which express and secrete insulin. In some embodiments, a population of pancreatic beta cells produced from the Pdx1-positive pancreatic progenitors can be used as a model for studying the differentiation pathway of cells which differentiate into islet β-cells or pancreatic β-like cells.

In other embodiments, the pancreatic beta cells differentiated from the Pdx1-positive pancreatic progenitors can be used as models for studying the role of islet β-cells in the pancreas and in the development of diabetes and metabolic disorders. In some embodiments, the pancreatic beta cells can be from a normal subject, or from a subject which carries a mutation and/or polymorphism (e.g. in the gene Pdx1 which leads to early-onset insulin-dependent diabetes mellitus (NIDDM), as well as maturity onset diabetes of the young type 4 (MODY4), which can be used to identify small molecules and other therapeutic agents that can be used to treat subjects with diabetes with a mutation or polymorphism in Pdx1. In some embodiments, the pancreatic beta cells and/or Pdx1-positive pancreatic progenitors may be genetically engineered to correct the polymorphism in the Pdx1 gene prior to being administered to a subject in the therapeutic treatment of a subject with diabetes. In some embodiments, the pancreatic beta cells and/or Pdx1-positive pancreatic progenitors may be genetically engineered to carry a mutation and/or polymorphism.

In one embodiment of the invention relates to a method of treating diabetes or a metabolic disorder in a subject comprising administering an effective amount of a composition comprising a population of pancreatic beta cells produced from the Pdx1-positive pancreatic progenitors as disclosed herein to a subject with diabetes and/or a metabolic disorder. In a further embodiment, the invention provides a method for treating diabetes, comprising administering a composition comprising a population of pancreatic beta cells produced from Pdx1-positive pancreatic progenitors as disclosed herein to a subject that has, or has increased risk of developing diabetes in an effective amount sufficient to produce insulin in response to increased blood glucose levels.

In one embodiment of the above methods, the subject is a human and a population of pancreatic beta cells as disclosed herein are human cells. In some embodiments, the invention contemplates that a population of pancreatic beta cells as disclosed herein are administered directly to the pancreas of a subject, or is administered systemically. In some embodiments, a population of pancreatic beta cells and/or Pdx1-positive pancreatic progenitors as disclosed herein can be administered to any suitable location in the subject, for example in a capsule in the blood vessel or the liver or any suitable site where administered population of pancreatic beta cells and/or Pdx1-positive pancreatic progenitors can differentiate into insulin-producing cells and can secrete insulin in response to increased glucose levels in the subject.

The present invention is also directed to a method of treating a subject with diabetes or a metabolic disorder which occurs as a consequence of genetic defect, physical injury, environmental insult or conditioning, bad health, obesity and other diabetes risk factors commonly known by a person of ordinary skill in the art. Efficacy of treatment of a subject administered a composition comprising a population of pancreatic beta cells and/or Pdx1-positive pancreatic progenitors can be monitored by clinically accepted criteria and tests, which include for example, (i) Glycated hemoglobin (A1C) test, which indicates a subjects average blood sugar level for the past two to three months, by measuring the percentage of blood sugar attached to hemoglobin, the oxygen-carrying protein in red blood cells. The higher your blood sugar levels, the more hemoglobin has sugar attached. An A1C level of 6.5 percent or higher on two separate tests indicates the subject has diabetes. A test value of 6-6.5% suggest the subject has prediabetes. (ii) Random blood sugar test. A blood sample will be taken from the subject at a random time, and a random blood sugar level of 200 milligrams per deciliter (mg/dL)-11.1 millimoles per liter (mmol/L), or higher indicated the subject has diabetes. (iii) Fasting blood sugar test. A blood sample is taken from the subject after an overnight fast. A fasting blood sugar level between 70 and 99 mg/dL (3.9 and 5.5 mmol/L) is normal. If the subjects fasting blood sugar levels is 126 mg/dL (7 mmol/L) or higher on two separate tests, the subject has diabetes. A blood sugar level from 100 to 125 mg/dL (5.6 to 6.9 mmol/L) indicates the subject has prediabetes. (iv) Oral glucose tolerance test. A blood sample will be taken after the subject has fasted for at least eight hours or overnight and then ingested a sugary solution, and the blood sugar level will be measured two hours later. A blood sugar level less than 140 mg/dL (7.8 mmol/L) is normal. A blood sugar level from 140 to 199 mg/dL (7.8 to 11 mmol/L) is considered prediabetes. This is sometimes referred to as impaired glucose tolerance (IGT). A blood sugar level of 200 mg/dL (11.1 mmol/L) or higher may indicate diabetes.

In some embodiments, the effects of administration of a population of pancreatic beta cells produced from Pdx1-positive pancreatic progenitors as disclosed herein to a subject in need thereof is associated with improved exercise tolerance or other quality of life measures, and decreased mortality. The effects of cellular therapy with pancreatic beta cells and/or Pdx1-positive pancreatic progenitors can be evident over the course of days to weeks after the procedure. However, beneficial effects may be observed as early as several hours after the procedure, and may persist for several years.

In some embodiments, a population of pancreatic beta cells and/or Pdx1-positive pancreatic progenitors as disclosed herein may be used for tissue reconstitution or regeneration in a human patient or other subject in need of such treatment. In some embodiments compositions of populations of pancreatic beta cells and/or Pdx1-positive pancreatic progenitors can be administered in a manner that permits them to graft or migrate to the intended tissue site and reconstitute or regenerate the functionally deficient area. Special devices are available that are adapted for administering cells capable of reconstituting a population of β-cells in the pancreas or at an alternative desired location. Accordingly, the pancreatic beta cells and/or Pdx1-positive pancreatic progenitors may be administered to a recipient subject's pancreas by injection, or administered by intramuscular injection.

In some embodiments, compositions comprising a population of pancreatic beta cells and/or Pdx1-positive pancreatic progenitors as disclosed herein have a variety of uses in clinical therapy, research, development, and commercial purposes. For therapeutic purposes, for example, a population of pancreatic beta cells and/or Pdx1-positive pancreatic progenitors as disclosed herein may be administered to enhance insulin production in response to increase in blood glucose level for any perceived need, such as an inborn error in metabolic function, the effect of a disease condition (e.g. diabetes), or the result of significant trauma (i.e. damage to the pancreas or loss or damage to islet β-cells). In some embodiments, a population of pancreatic beta cells and/or Pdx1-positive pancreatic progenitors as disclosed herein are administered to the subject not only help restore function to damaged or otherwise unhealthy tissues, but also facilitate remodeling of the damaged tissues.

To determine the suitability of cell compositions for therapeutic administration, the pancreatic beta cells and/or Pdx1-positive pancreatic progenitor cells can first be tested in a suitable animal model. At one level, cells are assessed for their ability to survive and maintain their phenotype in vivo. Cell compositions comprising pancreatic beta cells and/or Pdx1-positive pancreatic progenitors can be administered to immunodeficient animals (such as nude mice, or animals rendered immunodeficient chemically or by irradiation). Tissues are harvested after a period of regrowth, and assessed as to whether the administered cells or progeny thereof are still present.

This can be performed by administering cells that express a detectable label (such as green fluorescent protein, or beta-galactosidase); that have been prelabeled (for example, with BrdU or [3H] thymidine), or by subsequent detection of a constitutive cell marker (for example, using human-specific antibody). The presence and phenotype of the administered population of pancreatic beta cells and/or Pdx1-positive pancreatic progenitors can be assessed by immunohistochemistry or ELISA using human-specific antibody, or by RT-PCR analysis using primers and hybridization conditions that cause amplification to be specific for human polynucleotides, according to published sequence data.

A number of animal models for testing diabetes are available for such testing, and are commonly known in the art, for example as disclosed in U.S. Pat. No. 6,187,991 which is incorporated herein by reference, as well as rodent models; NOD (non-obese mouse), BB_DB mice, KDP rat and TCR mice, and other animal models of diabetes as described in Rees et al, Diabet Med. 2005 April; 22(4):359-70; Srinivasan K, et al., Indian J Med Res. 2007 March; 125(3):451-7; Chatzigeorgiou A, et al., In Vivo. 2009 March-April; 23(2):245-58, which are incorporated herein by reference.

In some embodiments, a population of pancreatic beta cells and/or Pdx1-positive pancreatic progenitors as disclosed herein may be administered in any physiologically acceptable excipient, where the pancreatic beta cells and/or Pdx1-positive pancreatic progenitors may find an appropriate site for regeneration and differentiation. In some embodiments, a population of pancreatic beta cells and/or Pdx1-positive pancreatic progenitors as disclosed herein can be introduced by injection, catheter, or the like. In some embodiments, a population of pancreatic beta cells and/or Pdx1-positive pancreatic progenitors as disclosed herein can be frozen at liquid nitrogen temperatures and stored for long periods of time, being capable of use on thawing. If frozen, a population of pancreatic beta cells and/or Pdx1-positive pancreatic progenitors will usually be stored in a 10% DMSO, 50% FCS, 40% RPMI 1640 medium. Once thawed, the cells may be expanded by use of growth factors and/or feeder cells associated with culturing β pancreatic beta cells and/or Pdx1-positive pancreatic progenitors as disclosed herein.

In some embodiments, a population of pancreatic beta cells and/or Pdx1-positive pancreatic progenitors as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of pancreatic beta cells and/or Pdx1-positive pancreatic progenitors as disclosed herein will be adapted in accordance with the route and device used for administration. In some embodiments, a composition comprising a population of pancreatic beta cells and/or Pdx1-positive pancreatic progenitors can also comprise or be accompanied with one or more other ingredients that facilitate the engraftment or functional mobilization of the pancreatic beta cells and/or Pdx1-positive pancreatic progenitors. Suitable ingredients include matrix proteins that support or promote adhesion of the pancreatic beta cells and/or Pdx1-positive pancreatic progenitors, or complementary cell types, especially endothelial cells. In another embodiment, the composition may comprise resorbable or biodegradable matrix scaffolds.

In some embodiments, a population of pancreatic beta cells and/or Pdx1-positive pancreatic progenitors as disclosed herein may be genetically altered in order to introduce genes useful in differentiated progeny, e.g. genes useful in insulin-producing cells such as pancreatic β-cells, e.g. repair of a genetic defect in an individual, selectable marker, etc., or genes useful in selection against non-insulin-producing cells differentiated from a definitive endoderm cell and/or Pdx1-positive pancreatic progenitor cell or for the selective suicide of implanted pancreatic beta cells and/or Pdx1-positive pancreatic progenitors. In some embodiments, a population of pancreatic beta cells and/or Pdx1-positive pancreatic progenitors can also be genetically modified to enhance survival, control proliferation, and the like. In some embodiments, a population of pancreatic beta cells and/or Pdx1-positive pancreatic progenitors as disclosed herein can be genetically altering by transfection or transduction with a suitable vector, homologous recombination, or other appropriate technique, so that they express a gene of interest. In one embodiment, a definitive endoderm cell and/or Pdx1-positive pancreatic progenitor is transfected with genes encoding a telomerase catalytic component (TERT), typically under a heterologous promoter that increases telomerase expression beyond what occurs under the endogenous promoter, (see International Patent Application WO 98/14592, which is incorporated herein by reference). In other embodiments, a selectable marker is introduced, to provide for greater purity of the population of pancreatic beta cells and/or Pdx1-positive pancreatic progenitors. In some embodiments, a population of pancreatic beta cells may be genetically altered using vector containing supernatants over a 8-16 h period, and then exchanged into growth medium for 1-2 days. Genetically altered pancreatic beta cells can be selected using a drug selection agent such as puromycin, G418, or blasticidin, and then recultured.

Gene therapy can be used to either modify a cell to replace a gene product, to facilitate regeneration of tissue, to treat disease, or to improve survival of the cells following implantation into a subject (i.e. prevent rejection).

In an alternative embodiment, a population of pancreatic beta cells produced from Pdx1-positive pancreatic progenitors as disclosed herein can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types, such as somatostatin, glucagon, and other factors.

Many vectors useful for transferring exogenous genes into target pancreatic beta cells produced from Pdx1-positive pancreatic progenitors as disclosed herein are available. The vectors may be episomal, e.g. plasmids, virus derived vectors such as cytomegalovirus, adenovirus, etc., or may be integrated into the target cell genome, through homologous recombination or random integration, e.g. retrovirus derived vectors such MMLV, HIV-1, ALV, etc. In some embodiments, combinations of retroviruses and an appropriate packaging cell line may also find use, where the capsid proteins will be functional for infecting the pancreatic beta cells disclosed herein. Usually, pancreatic beta cells produced from Pdx1-positive pancreatic progenitors and virus will be incubated for at least about 24 hours in the culture medium. In some embodiments, the pancreatic beta cells and/or Pdx1-positive pancreatic progenitors are then allowed to grow in the culture medium for short intervals in some applications, e.g. 24-73 hours, or for at least two weeks, and may be allowed to grow for five weeks or more, before analysis. Commonly used retroviral vectors are "defective", i.e. unable to produce viral proteins required for productive infection. Replication of the vector requires growth in the packaging cell line.

The host cell specificity of the retrovirus is determined by the envelope protein, env (p120). The envelope protein is provided by the packaging cell line. Envelope proteins are of at least three types, ecotropic, amphotropic and xenotropic. Retroviruses packaged with ecotropic envelope protein, e.g. MMLV, are capable of infecting most murine and rat cell types. Ecotropic packaging cell lines include BOSC23 (Pear et al. (1993) P.N.A.S. 90:8392-8396). Retroviruses bearing amphotropic envelope protein, e.g. 4070A (Danos et al, supra.), are capable of infecting most mammalian cell types, including human, dog and mouse. Amphotropic packaging cell lines include PA12 (Miller et al. (1985) Mol. Cell. Biol. 5:431-437); PA317 (Miller et al. (1986) Mol. Cell. Biol. 6:2895-2902) GRIP (Danos et al. (1988) PNAS 85:6460-6464). Retroviruses packaged with xenotropic envelope protein, e.g. AKR env, are capable of infecting most mammalian cell types, except murine cells. In some embodiments, the vectors may include genes that must later be removed, e.g. using a recombinase system such as Cre/Lox, or the cells that express them destroyed, e.g. by including genes that allow selective toxicity such as herpesvirus TK, Bcl-Xs, etc.

Suitable inducible promoters are activated in a desired target cell type, either the transfected cell, or progeny thereof. By transcriptional activation, it is intended that transcription will be increased above basal levels in the target cell by at least about 100 fold, more usually by at least about 1000 fold. Various promoters are known that are induced in different cell types.

In one aspect of the present invention, a population of pancreatic beta cells and/or Pdx1-positive pancreatic progenitors as disclosed herein are suitable for administering systemically or to a target anatomical site. A population of pancreatic beta cells and/or Pdx1-positive pancreatic progenitors can be grafted into or nearby a subject's pancreas, for example, or may be administered systemically, such as, but not limited to, intra-arterial or intravenous administration. In alternative embodiments, a population of pancreatic beta cells and/or Pdx1-positive pancreatic progenitors of the present invention can be administered in various ways as would be appropriate to implant in the pancreatic or secretory system, including but not limited to parenteral, including intravenous and intraarterial administration, intrathecal administration, intraventricular administration, intraparenchymal, intracranial, intracisternal, intrastriatal, and intranigral administration. Optionally, a population of pancreatic beta cells and/or Pdx1-positive pancreatic progenitors are administered in conjunction with an immunosuppressive agent.

In some embodiments, a population of pancreatic beta cells and/or Pdx1-positive pancreatic progenitors can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of pancreatic beta cells and/or Pdx1-positive pancreatic progenitors can be administered to a subject the following locations: clinic, clinical office, emergency department, hospital ward, intensive care unit, operating room, catheterization suites, and radiologic suites.

In other embodiments, a population of pancreatic beta cells produced from Pdx1-positive pancreatic progenitors is stored for later implantation/infusion. A population of pancreatic beta cells produced from Pdx1-positive pancreatic progenitors may be divided into more than one aliquot or unit such that part of a population of pancreatic beta cells is retained for later application while part is applied immediately to the subject. Moderate to long-term storage of all or part of the cells in a cell bank is also within the scope of this invention, as disclosed in U.S. Patent Application Serial No. 20030054331 and Patent Application No. WO03024215, and is incorporated by reference in their entireties. At the end of processing, the concentrated cells may be loaded into a delivery device, such as a syringe, for placement into the recipient by any means known to one of ordinary skill in the art.

In some embodiments, a population of pancreatic beta cells produced from Pdx1-positive pancreatic progenitors can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of pancreatic beta cells produced from Pdx1-positive pancreatic progenitors may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Muramatsu et al., 1998).

In another aspect, in some embodiments, a population of pancreatic beta cells produced from Pdx1-positive pancreatic progenitors could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid' adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Pub. No 2002/0182211, which is incorporated herein by reference. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the cardiovascular stem cells of the invention.

Pharmaceutical compositions comprising effective amounts of a population of pancreatic beta cells produced from Pdx1-positive pancreatic progenitors are also contemplated by the present invention. These compositions comprise an effective number of pancreatic beta cells and/or Pdx1-positive pancreatic progenitors, optionally, in combination with a pharmaceutically acceptable carrier, additive or excipient. In certain aspects of the present invention, a population of pancreatic beta cells produced from Pdx1-positive pancreatic progenitors are administered to the subject in need of a transplant in sterile saline. In other aspects of the present invention, a population of pancreatic beta cells produced from Pdx1-positive pancreatic progenitors are administered in Hanks Balanced Salt Solution (HBSS) or Isolyte S, pH 7.4. Other approaches may also be used, including the use of serum free cellular media. In one embodiment, a population of pancreatic beta cells produced from Pdx1-positive pancreatic progenitors are administered in plasma or fetal bovine serum, and DMSO. Systemic administration of a population of pancreatic beta cells and/or Pdx1-positive pancreatic progenitors cells to the subject may be preferred in certain indications, whereas direct administration at the site of or in proximity to the diseased and/or damaged tissue may be preferred in other indications.

In some embodiments, a population of pancreatic beta cells can optionally be packaged in a suitable container with written instructions for a desired purpose, such as the reconstitution or thawing (if frozen) of a population of pancreatic beta cells and/or Pdx1-positive pancreatic progenitors prior to administration to a subject.

In one embodiment, an isolated population of pancreatic beta cells produced from Pdx1-positive pancreatic progenitors as disclosed herein are administered with a differentiation agent. In one embodiment, the pancreatic beta cells and/or Pdx1-positive pancreatic progenitors are combined with the differentiation agent to administration into the subject. In another embodiment, the cells are administered separately to the subject from the differentiation agent. Optionally, if the cells are administered separately from the differentiation agent, there is a temporal separation in the administration of the cells and the differentiation agent. The temporal separation may range from about less than a minute in time, to about hours or days in time. The determination of the optimal timing and order of administration is readily and routinely determined by one of ordinary skill in the art.

Diagnosis of Diabetes

Type 1 diabetes is an autoimmune disease that results in destruction of insulin-producing beta cells of the pancreas. Lack of insulin causes an increase of fasting blood glucose (around 70-120 mg/dL in nondiabetic people) that begins to appear in the urine above the renal threshold (about 190-200 mg/dl in most people). The World Health Organization defines the diagnostic value of fasting plasma glucose concentration to 7.0 mmol/l (126 mg/dl) and above for Diabetes Mellitus (whole blood 6.1 mmol/l or 110 mg/dl), or 2-hour glucose level of 11.1 mmol/L or higher (200 mg/dL or higher).

Type 1 diabetes can be diagnosed using a variety of diagnostic tests that include, but are not limited to, the following: (1) glycated hemoglobin (A1C) test, (2) random blood glucose test and/or (3) fasting blood glucose test.

The Glycated hemoglobin (A1C) test is a blood test that reflects the average blood glucose level of a subject over the preceding two to three months. The test measures the percentage of blood glucose attached to hemoglobin, which correlates with blood glucose levels (e.g., the higher the blood glucose levels, the more hemoglobin is glycosylated). An A1C level of 6.5 percent or higher on two separate tests is indicative of diabetes. A result between 6 and 6.5 percent is considered prediabetic, which indicates a high risk of developing diabetes.

The Random Blood Glucose Test comprises obtaining a blood sample at a random time point from a subject suspected of having diabetes. Blood glucose values can be expressed in milligrams per deciliter (mg/dL) or millimoles per liter (mmol/L). A random blood glucose level of 200 mg/dL (11.1 mmol/L) or higher indicates the subject likely has diabetes, especially when coupled with any of the signs and symptoms of diabetes, such as frequent urination and extreme thirst.

For the fasting blood glucose test, a blood sample is obtained after an overnight fast. A fasting blood glucose level less than 100 mg/dL (5.6 mmol/L) is considered normal. A fasting blood glucose level from 100 to 125 mg/dL (5.6 to 6.9 mmol/L) is considered prediabetic, while a level of 126 mg/dL (7 mmol/L) or higher on two separate tests is indicative of diabetes.

Type 1 diabetes can also be distinguished from type 2 diabetes using a C-peptide assay, which is a measure of endogenous insulin production. The presence of anti-islet antibodies (to Glutamic Acid Decarboxylase, Insulinoma Associated Peptide-2 or insulin), or lack of insulin resistance, determined by a glucose tolerance test, is also indicative of type 1, as many type 2 diabetics continue to produce insulin internally, and all have some degree of insulin resistance.

Testing for GAD 65 antibodies has been proposed as an improved test for differentiating between type 1 and type 2 diabetes as it appears that the immune system is involved in Type 1 diabetes etiology.

In some embodiments, the present invention provides compositions for the use of populations of pancreatic beta cells or populations of Pdx1-positive pancreatic progenitor cells produced by the methods as disclosed herein or their differentiated progeny to restore islet function in a subject in need of such therapy. Any condition relating to inadequate production of a pancreatic endocrine (insulin, glucagon, or somatostatin), or the inability to properly regulate secretion may be considered for treatment with cells (e.g. populations of pancreatic beta cells or populations of Pdx1-positive pancreatic progenitor cells) prepared according to this invention, as appropriate. Of especial interest is the treatment of Type I (insulin-dependent) diabetes mellitus.

Subjects in need thereof can be selected for treatment based on confirmed long-term dependence on administration of exogenous insulin, and acceptable risk profile. The subject receives approximately 10,000 pancreatic beta cells or Pdx1-positive pancreatic progenitor cells equivalents per kg body weight. If the cells are not autologouse, in order to overcome an allotype mismatch, the subject can be treated before surgery with an immunosuppressive agent such as FK506 and rapamycin (orally) and daclizumab (intravenously). A composition comprising a populations of pancreatic beta cells and/or population of Pdx1-positive pancreatic progenitor cells can be infused through a catheter in the portal vein. The subject can then be subjected to abdominal ultrasound and blood tests to determine liver function. Daily insulin requirement is tracked, and the subject is given a second transplant if required. Follow-up monitoring includes frequent blood tests for drug levels, immune function, general health status, and whether the patient remains insulin independent.

General approaches to the management of the diabetic patient are provided in standard textbooks, such as the Textbook of Internal Medicine, 3rd Edition, by W. N. Kelley ed., Lippincott-Raven, 1997; and in specialized references such as Diabetes Mellitus: A Fundamental and Clinical Text 2nd Edition, by D. Leroith ed., Lippincott Williams & Wilkins 2000; Diabetes (Atlas of Clinical Endocrinology Vol. 2) by C. R. Kahn et al. eds., Blackwell Science 1999; and Medical Management of Type 1 Diabetes 3rd Edition, McGraw Hill 1998. Use of islet cells for the treatment of Type I diabetes is discussed at length in Cellular Inter-Relationships in the Pancreas: Implications for Islet Transplantation, by L. Rosenberg et al., Chapman & Hall 1999; and Fetal Islet Transplantation, by C. M. Peterson et al. eds., Kluwer 1995.

As always, the ultimate responsibility for subject selection, the mode of administration, and dosage of a population of pancreatic beta cells or a population of Pdx1-positive pancreatic progenitor cells is the responsibility of the managing clinician. For purposes of commercial distribution, populations of pancreatic beta cells produced from populations of Pdx1-positive pancreatic progenitor cells as disclosed herein are typically supplied in the form of a pharmaceutical composition, comprising an isotonic excipient prepared under sufficiently sterile conditions for human administration. This invention also includes sets of population of pancreatic beta cells produced from populations of Pdx1-positive pancreatic progenitor cells that exist at any time during their manufacture, distribution, or use. The sets of populations of pancreatic beta cells comprise any combination of two or more cell populations described in this disclosure, exemplified but not limited to the differentiation of pancreatic beta cells into their subsequent differentiation e.g. into insulin-producing cells such as pancreatic β-cells or pancreatic β-like cells as the term is defined herein. In some embodiments, the cell compositions comprising populations of pancreatic beta cells produced from populations of Pdx1-positive pancreatic progenitor cells can be administered (e.g. implanted into a subject) in combination with other cell types e.g. other differentiated cell types, sometimes sharing the same genome. Each cell type in the set may be packaged together, or in separate containers in the same facility, or at different locations, under control of the same entity or different entities sharing a business relationship.

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996. The composition is optionally packaged in a suitable container with written instructions for a desired purpose, such as the treatment of diabetes.

In some embodiments, compositions comprising populations of pancreatic beta cells produced from populations of Pdx1-positive pancreatic progenitor cells can also be used as the functional component in a mechanical device designed to produce one or more of the endocrine polypeptides of pancreatic islet cells. In its simplest form, the device contains a population of pancreatic beta cells produced from populations of Pdx1-positive pancreatic progenitor cells behind a semipermeable membrane that prevents passage of the cell population, retaining them in the device, but permits passage of insulin, glucagon, or somatostatin secreted by the cell population. This includes populations of pancreatic beta cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers >3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated for use to comprise a population of pancreatic beta cells produced from a population of Pdx1-positive pancreatic progenitor cells, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

In some embodiments, the methods described herein have one or more of the following advantages over other methods of making endoderm known in the art: the ability to insulin beta cells, e.g., reduced cost of producing insulin beta cells; easier and/or simplified production of insulin beta cells, using a small molecule such as a compound described herein (for example, as opposed to a protein or other biological molecule); or increased efficiency in generating insulin beta cells. In some embodiments, a method described herein results in the production of insulin positive cells by exposure to a small molecule compound such as a compound described herein.

In some embodiments, the methods described herein have one or more of the following advantages over other methods of the generation of pancreatic lineage cells by differentiation of endoderm (e.g., definitive endoderm) relative to other methods known in the art. Exemplary advantages include the ability to produce pancreatic cells and pancreatic precursor cells at low cost, easier and simplified production of pancreatic cells and pancreatic precursor cells, and increased efficiency in generating pancreatic cells and pancreatic precursor cells. In some embodiments, the methods described herein result in the production of Pdx1+ pancreatic cells and pancreatic precursor cells from endoderm (e.g., definitive endoderm) produced by the methods described herein.

In some examples, statistically significant means there is statistical evidence that there is a difference; it does not mean the difference is necessarily large, important, or significant in the common meaning of the word. The significance level of a test is a traditional frequentist statistical hypothesis testing concept. It can be defined as the probability of making a decision to reject the null hypothesis when the null hypothesis is actually true (a decision known as a Type I error, or "false positive determination"). The decision is often made using the p-value: if the p-value is less than the significance level, then the null hypothesis is rejected. The significance level of a test can also mean a probability such that the probability of making a decision to reject the null hypothesis when the null hypothesis is actually true is no more than the stated probability. This allows for those applications where the probability of deciding to reject may be much smaller than the significance level for some sets of assumptions encompassed within the null hypothesis.

EXAMPLES

Many modifications and variations of this invention can be made without departing from its spirit and scope, as will be apparent to those skilled in the art. The specific embodiments described herein are offered by way of example only, and the invention is to be limited only in terms of the appended claims, along with the full scope of equivalents to which such claims are entitled.

Experimental Procedures hESC culture and differentiation. Protocol 1. HUES 8 and H1 cells are routinely cultured on irradiated MEF feeder cells in KnockOut DMEM (Invitrogen) supplemented with 10% (v/v) KnockOut serum replacement (Invitrogen), 0.5% (v/v) human plasma fraction (Talecris Biotech), 2 mM L-glutamine (Invitrogen), 1.1 mM 2-mercaptoethanol (Invitrogen), 1 mM nonessential amino acids (Invitrogen), 1× penicillin/streptomycin (PS, Invitrogen) and 10 ng/ml bovine FGF (Invitrogen). Cells are passaged at the ratio of 1:6 every 5 d by using 0.05% trypsin (Invitrogen). To generate the HUES-pancreatic progenitor population, HUES cells were cultured on MEF feeder cells until 80-90% confluent, then treated with 25 ng/ml Wnt3a (R&D systems)+100 ng/ml activin A (R&D systems) in RPMI (Invitrogen) supplemented with 1×L-glutamine and 1×PS for 1 d, and then 100 ng/ml activin A in RPMI supplemented with 1×L-glutamine, 1×PS and 0.2% (v/v) fetal bovine serum (FBS, Invitrogen). The medium was changed 2 d later to 50 ng/ml/FGF7 (R&D systems) in RPMI supplemented with 1×L-glutamine, 1×PS and 2% (v/v) FBS, and maintained for an additional 2 d. Cells were then transferred to 100 ng/ml Noggin (R&D systems)+0.25 µM SANT-1 (Sigma)+2 µM retinoic acid (Sigma) in DMEM supplemented with 1×L-glutamine, 1×PS and 1×B27 (Invitrogen) and cultured for an 4 d, followed by treatment with 100 ng/ml Noggin (R&D systems)+1 µM ALK5 inhibitor (Enzo)+100 nM PDBu (Sigma) in DMEM supplemented with 1×L-glutamine, 1×PS and 1×B27 (Invitrogen) and cultured for an additional 4 d. All HUES-pancreatic progenitor cells were derived using the same protocol as described above. The percentage and number of PDX1$^+$ cells and NGN3$^+$ cells were analyzed with the Cellomics high content screening system (Thermo Scientific). PKCβ inhibitor was purchased from Calbiochem.

High-content screen 1. The quality of all compounds was assured by the vender as greater than 90% pure. The library includes compounds from Sigma LOPAC (at world wide web at: "sigmaaldrich.com/chemistry/drug-discovery/validation-libraries/lopac1280-navigator.html/"), and a home-made libraries containing activators and inhibitors of signaling pathways. Data were normalized as fold change compared with DMSO control. Hit compounds were defined as those higher than threefold compared to the DMSO control. Individual samples of hit compounds were picked from the original library and confirmed with the same method as in the primary screen for three times. Three compounds were confirmed for further assay.

Screen 1: Generation of efficacy curve. The HUES 8-pancreatic progenitor population was generated and plated onto 96-well plates with the same method as the high-content screen. After overnight incubation, the hit compounds were added at final concentrations of 30 µM, 10 µM, 3.3 µM, 1.1 µM, 370 nM, 123 nM, 41 nM, and 14 nM. Six days later, the cells were stained with NGN3 antibody and the plates were analyzed with the Cellomics high content screening system (Thermo Scientific).

Screen 1: Immunostaining. Cells were fixed with 10% (v/v) formalin solution (Sigma) for 20 min at room temperature (22-24° C.). Immunostaining was carried out with standard protocols. The following primary antibodies were used: goat anti-PDX1 (1:500, R&D system, AF2419); guinea pig anti-insulin (1:1,000, Dako, A0564); rabbit anti-glucagon (1:200, Cell Signaling, 2760); rabbit anti-c-peptide (1:500, Linco, 4020-01); and sheep anti-NGN3 (1:100, RnD systems, AF3444). Alexa-488-, Alexa-555- and Alexa-647- conjugated donkey antibodies against mouse, rabbit, guinea pig, goat, and sheep (Invitrogen), were used at 1:500 dilution.

hESC culture and differentiation. Protocol 2. Human ESCs were routinely cultured on hESC-certified matrigel (BD Biosciences) in mouse embryonic fibroblast conditioned hES media (MEF-CM). MEF-CM media was produced by conditioning hESC media for 24 days on a confluent layer of mouse embryonic fibroblasts and subsequently adding 20 ng/ml bFGF (Invitrogen). hES media was composed of DMEM/F12 (GIBCO) media supplemented with 20% KnockOut Serum Replacement (GIBCO), 2 mM Lglutamine (L-Glu, GIBCO), 1.1 mM 2-mercaptoethanol (GIBCO), 1 mM nonessential amino acids (GIBCO), 1× penicillin/strepto-mycin (P/S,GIBCO). Cells were passaged at the ratio of 1:6-1:20 every 4-7 days using TrypLE Express (Invitrogen).

To initiate differentiation the cells were dissociated using TrypLE Express to single cells and seeded at 150,000 cell/cm2 onto 1:30 dilution of growth factor reduced matrigel (BD Biosciences) in DMEM/F12 in MEF-CM media with 10 μM Y27632 (StemGent). Two days following seeding the differentiation was started. Cells were exposed to RPMI 1640 (Invitrogen) supplemented with 2% reagent grade BSA (Proliant) and 20 ng/ml human Wnt3a (R&D Systems)+100 ng/ml rhActivinA (R&D Systems)+8 ng/ml bFGF (Invitrogen) for the first day (stage 1.1). During day 2 and 3 the day1 media was used with the exception of Wnt3a (stage 1.2). During days 4-5 cells were treated with RPMI+ 2% BSA+50 ng/ml FGF7 (Peprotech) (stage 2). For days 6-9 cells were treated with DMEM-HG (Invitrogen)+0.1% Albumax BSA (Invitrogen)+1:200 ITS-X (Invitrogen)+50 ng/ml FGF7 (Peprotech)+2 μM RA (Sigma)+0.25 μM SANT-1 (Sigma)+20 ng/ml rhActivinA (R&D Systems)+ 100 ng/ml rhNoggin (R&D Systems) (stage 3). During days 10-12 cells were treated with DMEM-HG (Invitrogen)+ 0.1% Albumax BSA (Invitrogen)+1:200 ITS-X (Invitrogen)+100 ng/ml rhNoggin (R&D Systems)+0.25 μM SANT-1 (Sigma)+100 nM PDBu (EMD Biosciences) (stage 4). During days 13-15 cells were treated with DMEM-HG (Invitrogen)+0.1% Albumax BSA (Invitrogen)+1:200 ITS-X (Invitrogen)+100 ng/ml rhNoggin (R&D Systems)+1 μM Alk5 inhibitor (Axxora) (stage 5). PKC inhibitor Bisindolylmaleimide I (VWR) was added during stage 5.

High-content screen 2. The compound libraries used for this study: 400 compounds, including bioactive molecules, natural products, and 400 compounds that are known modulators of development or signaling pathways. For the chemical screen the day 8 cells were dispersed into single cells, using TrypLE, and replated at 150,000 cells/well of a 96 well plate in the presence of stage 3 media and 10 μM Y27632. Compounds were added to the wells on day 10 in stage 4 media, then again on days 12 and 14 in stage 5 media. Media was changed every other day suing the treatment. Cells were fixed using 4% paraformaldehyde (PFA, Sigma) on day 15 and stained using mouse antiglucagon and rabbit anti-c-peptide antibodies.

Screen 2: Immunostaining. Following 4% PFA fixation, cells were 3×5 min washed in PBS and blocked with 10% donkey serum (Jackson Immunoresearch) in PBS/0.3% Triton X. Primary antibodies were incubated overnight at 4 C. Secondary antibodies were incubated for 1 hr at room temperature. The following primary antibodies and dilutions were used: rabbit anti-cpeptide (1:1000, BCBC), rat anti-c-peptide (1:500, DSHB, GN-ID4), guinea pig anti-insulin (1:1000, DAKO, A0564), guinea pig anti-glucacon (1:500, DAKO), mouse anti-glucagon (1:500, Sigma Aldrich, G2654), goat anti-PDX1 (R&D Systems AF2419), mouse anti-NKX6.1 (DSHB, F55A12), rabbit anti-UCN3 (1:500, Phoenix Pharmaceuticals, H-019-28).

Kidney capsule implantation and tissue preparation. All animal experiments were performed following an approved protocol of Harvard University under assurance # A3593-1 (protocol 93-15). The cells were washed with DPBS 3 times and collected for transplantation. The cells were then lifted with a cell scraper, collected by centrifugation and resuspended in 50 μl PBS. About 40 μl (3-4×10$^6$ cells) of cell clumps were implanted into the left kidney of avertin-anesthetized SCID-Beige mice. 12 weeks later, the mouse sera were collected after overnight fasting condition or 30 mins after 3 g/kg D-Glucose treatment by IP injection. The c-peptide levels in mouse sera were measured using the human c-peptide ELISA kit (Alpco Diagnostics or Millipore).

Example 1

Human embryonic stem cells (hESCs) and induced pluripotent stem cells (iPSCs) represent a potentially unlimited starting material for the generation of functional pancreatic cells for transplantation therapy and disease modeling of diabetes. Essential in this pursuit is an efficient method for the differentiation of hESCs/iPSCs down the pancreatic lineage to produce endocrine cells. By mimicking known signals used during embryonic pancreatic development in vivo, efficient stepwise protocols have been developed to differentiate hESCs first into definitive endoderm and then into pancreatic progenitors (FIG. 1A)[1-9]. However, the signals needed to produce endocrine progenitors from pancreatic progenitors, as well as insulin-expressing β cells from the endocrine progenitors, remain poorly defined. Several recent studies reported that blocking TGFβ signaling and BMP signaling can improve the differentiation of pancreatic progenitors into endocrine cells[1,10,11]. However, the overall efficiency of creating insulin-producing cells is still very low. Thus, additional work needs to be done to dissect the signaling pathway controlling the differentiation of pancreatic progenitors to endocrine cells.

Based on the inventors previous success using high throughput chemical screening to identify the small molecules that direct hESC differentiation toward definitive endoderm[12] (as disclosed in US Patent Application US2012/008830) and pancreatic progenitors[13] (as disclosed in US Patent Application: US2011/0070645), the inventors herein utilized the same approach to identify small molecules that could facilitate the further differentiation of pancreatic progenitors towards endocrine cells. To maximize the chance of success, the inventors performed two independent chemical screens that differed in the choice of hESC lines, directed differentiation protocols, chemical libraries and primary screening assays. Both screens identified PKC antagonists as inducers of the endocrine pancreatic lineage. Together with our previous work implicating PKC agonists in the induction of pancreatic progenitors, we suggest a highly dynamic role for PKC during pancreatic development and propose improvements to current directed differentiation protocols that result in the production of up to ten-fold more endocrine cells.

Figures 1A, 1B, 1C, 1D, 1E, 1F, 1G, 1H, 1I, 1J, 1K:
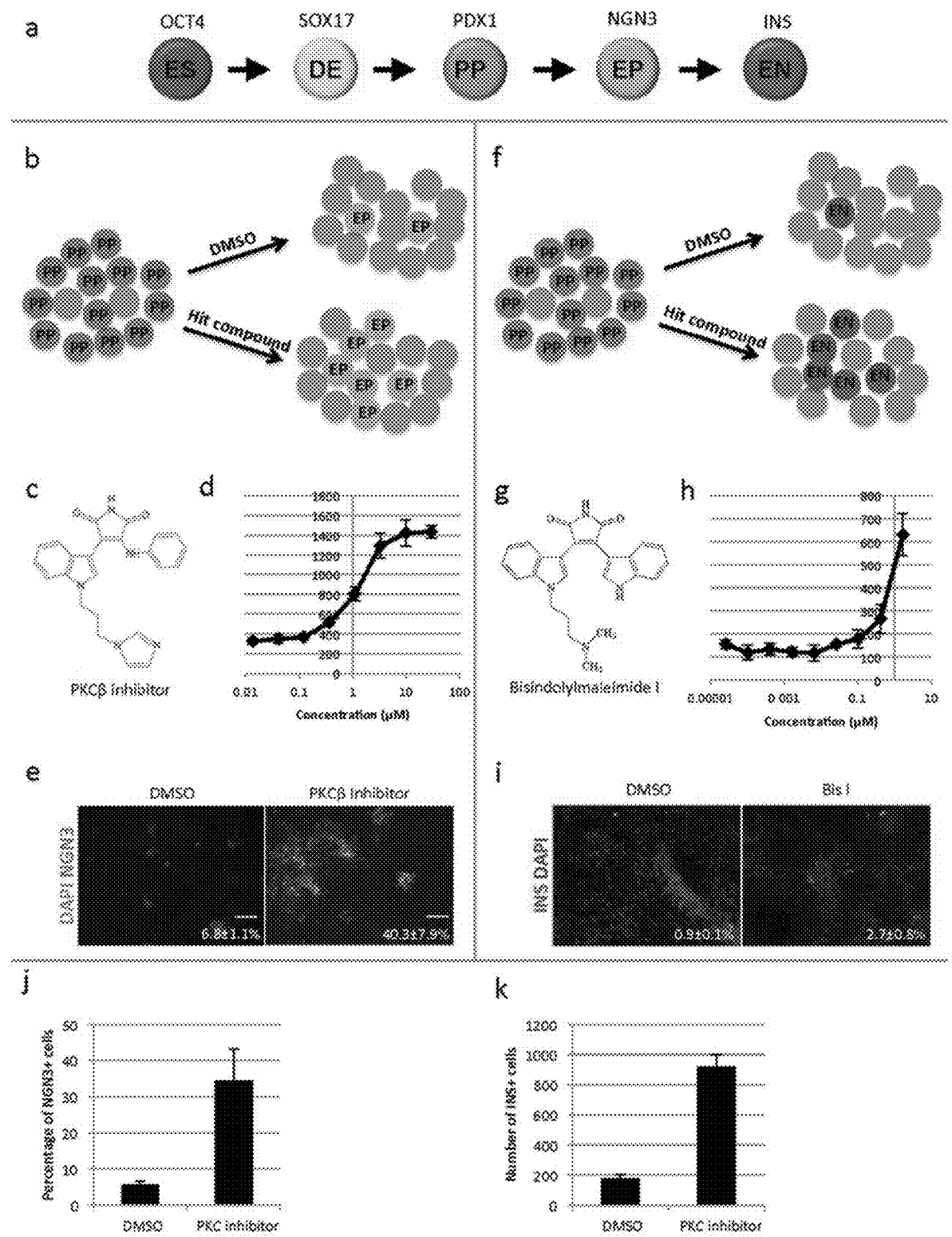
FIGS. 1A-1K show high-content screens to increase the number of NGN3-expressing and insulin-expressing cells.

Lineage tracing studies in mice have shown that production of hormone-expressing endocrine cells from pancreatic progenitors (marked by expression of Pancreatic and Duodenal Homeobox 1, PDX1) requires an intermediate stage, termed endocrine progenitor, in which cells express the key transcription factor Neurogenin 3 (NGN3)[14]. NGN3 expression is transient during embryonic development, raising questions about whether a screen set up to detect this necessary intermediate stage (NGN3 expression) could be successful. Thus two screens were designed to identify compounds that could promote endocrine differentiation. In the first screen (see Table 1), the inventors screened for compounds that could increase the percentage and the total number of NGN3+ endocrine progenitors produced from PDX1+ hESC-derived pancreatic progenitors (FIG. 1B). Concurrently, the inventors performed a screen for compounds that could promote the appearance of insulin-expressing endocrine cells from PDX1+ progenitors after prolonged culture.

Figures 4A, 4B:
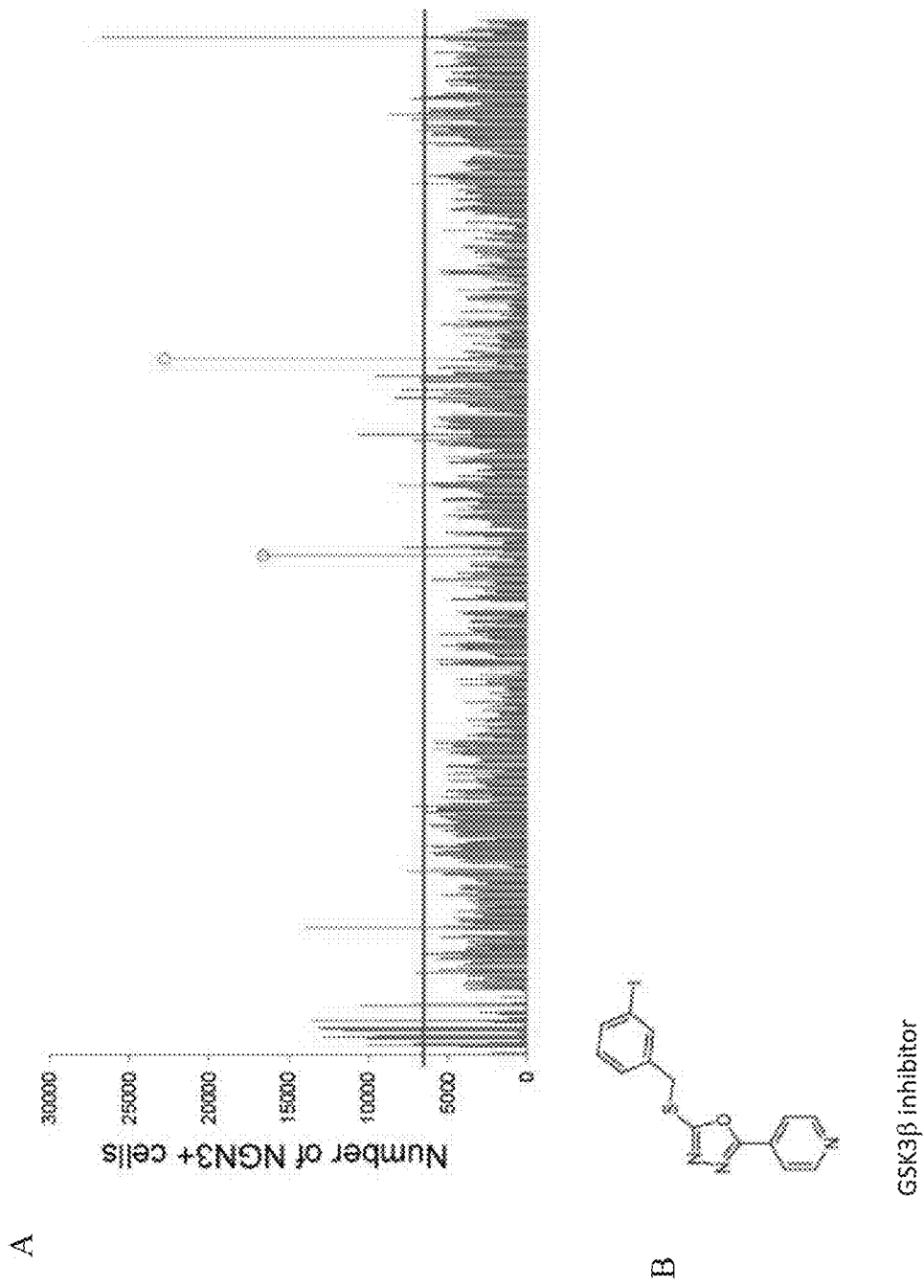
FIGS. 4A-4B show the data analysis of the first primary screen.
Figure 5:
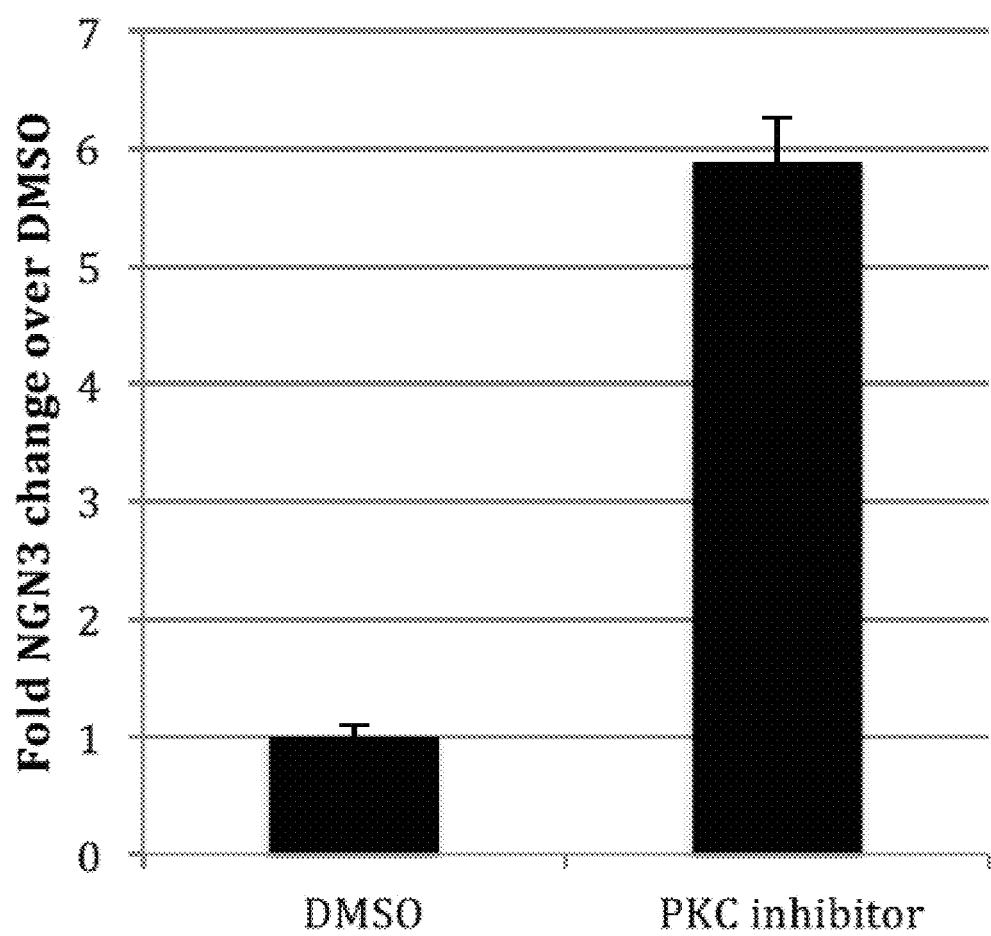
FIG. 5 shows the results of a qRT-PCR analysis of the expression of NGN3 in the chemically-treated populations.

For the first screen, to detect compounds that could promote the appearance of NGN3+ endocrine progenitors, the inventors differentiated HUES8 hESC cells using a modified version of previously published protocols[13] (see Methods section, Protocol 1), to produce a population containing 71.2 6.5% PDX1+ pancreatic progenitors. Compounds from a library containing 2000 chemicals, including signaling pathway regulators, kinase inhibitors, natural products, and FDA approved drugs (detailed library information is described in the Methods) were individually tested at 10M and 1 M final concentrations, corresponding to 0.1% and 0.01% DMSO respectively. After six days culture, cells were stained with an antibody against NGN3 and analyzed with a Cellomics high content imaging reader (Thermo Scientific). In DMSO control conditions, 6.8 1.1% cells stained positively for NGN3. Two primary hits increased the number of NGN3 expressing cells more than three fold (FIG. 4). Among these, a PKCβ inhibitor shown as follows:

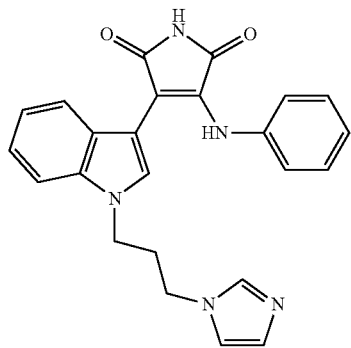 [SMILES: O=C1NC(=O)C(c2cn(CCCn3ccnc3)c3ccccc23)=C1Nc1ccccc1]

was selected for follow up studies due to the high efficacy and low toxicity (FIG. 1C). PKCβ inhibitor treatment increased the total number of NGN3+ cells in a dose dependent manner (EC50=7.8 µM, FIG. 1D), increasing the percentage of NGN3+ cells to a maximum of 40.3 7.9%, nearly 7-fold higher than the DMSO-treated controls (6.8 1.1%) (FIG. 1E). Quantitative RT-PCR analysis confirmed that the PKCβ inhibitor-treated cells showed higher expression of NGN3 mRNA compared to DMSO controls (FIG. 4).

Example 2

In parallel with the screen described above, the inventors carried out a second screen (see Table 2) to increase the total number of insulin-expressing cells produced from pancreatic progenitors (FIG. 1F). In order to discover novel pathways to increase the total number of insulin-producing cells, both control and experimental conditions were treated with compounds that had been previously shown to facilitate the induction of the endocrine lineage, namely Noggin (a BMP inhibitor) and Alk5 inhibitor (a TGF inhibitor)[1,10]. The hESC line H1 was differentiated (see Methods section—Protocol 2) until stage 3 day 4 (S3D4) to produce a population containing approximately 80% PDX1+ pancreatic progenitors, at which time a collection of 418 kinase inhibitors, signaling pathway regulators, and natural products were individually tested at 10 M final concentrations, corresponding to 0.1% DMSO. After 6 days of compound treatment, cells were fixed, stained using an insulin antibody, and analyzed using by high-content imaging on a Cellomics instrument. The screen identified 6 compounds that increased the number of insulin expressing cells >3 fold over the DMSO controls (FIG. 6B).

Notably, in light of the results of the first screen, 4 of the 6 hit compounds were classified as PKC inhibitors. Since 3 hit compounds were in the bisindolylmaleimide family, the inventors selected Bisindolylmaleimide I (BisI) with the following structure:

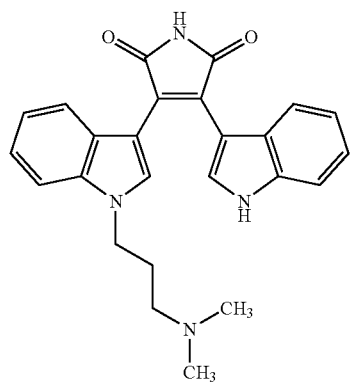 [SMILES: CN(C)CCCn1cc(C2=C(c3c[nH]c4ccccc34)C(=O)NC2=O)c2ccccc21]

for subsequent studies (FIG. 1G). BisI increased the total number of insulin-expressing cells in a dose dependent manner (EC50=848 nM, FIG. 1H). Significant auto-fluorescence and toxicity hampered dose-curve measurements at 6.75 M and 27 M. 1 M BisI induced up to 2.7 0.8% insulin-expressing cells, compared with 0.9 0.1% for DMSO-treated controls (FIG. 1I). Consistent with our earlier finding that PKC inhibition induces the endocrine lineage, BisI treatment moderately increased mRNA expression of multiple hormones expressed downstream of NGN3, including insulin (2.6 0.5-fold), glucagon (2.2 0.4-fold), and somatostatin (1.25 0.1 fold) (FIG. 7).

Example 3

To confirm that the effects of individual PKC inhibitors were not cell line specific, the inventors tested them on the differentiation of both HUES8 and H1 cell lines. H1 pancreatic progenitors treated with PKCβ3 inhibitor had a higher percentage of NGN3-expressing cells (34 8%) than DMSO treated controls (5.71%) (FIG. 1j). Similarly, BisI increased the numbers of insulin-expressing cells in HUES8 up to 7.5 fold in the presence of Noggin and Alk5 inhibitor (FIG. 1K). Thus, our parallel screening approaches identified a broad utility for PKC inhibition in the induction of the endocrine pancreatic lineage from hESC-derived pancreatic progenitors.

Figure 2A:
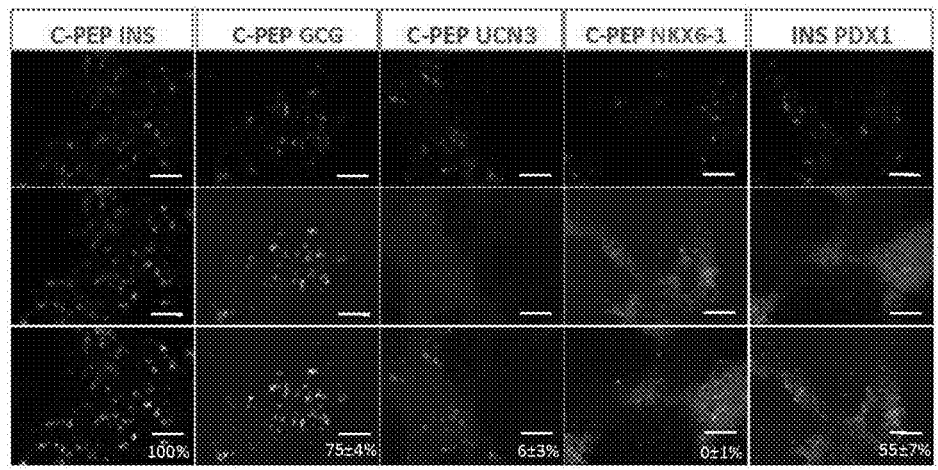
FIGS. 2A-2B show the characterization of cells derived by PKC inhibitor treatment.

Previous work showed that insulin-producing cells generated by in vitro differentiation of hESCs are not fully functional beta-cells. The inventors therefore sought to determine whether insulin-expressing cells produced through the inhibition of PKC more closely resembled normal beta (β) cells. The inventors observed that insulin-expressing cells differentiated in the presence of BisI displayed many features common to other insulin-expressing cells produced using in vitro differentiation1,3,4,10,15-[17], in that they are often polyhormonal, and lack expression of mature β cell markers Nkx6 and Ucn3 (FIG. 2A). The inventors therefore conclude that the insulin-expressing cells produced in vitro following PKC inhibition resemble those which have been previously reported and are not true β cells.

Example 4

Figure 2B:
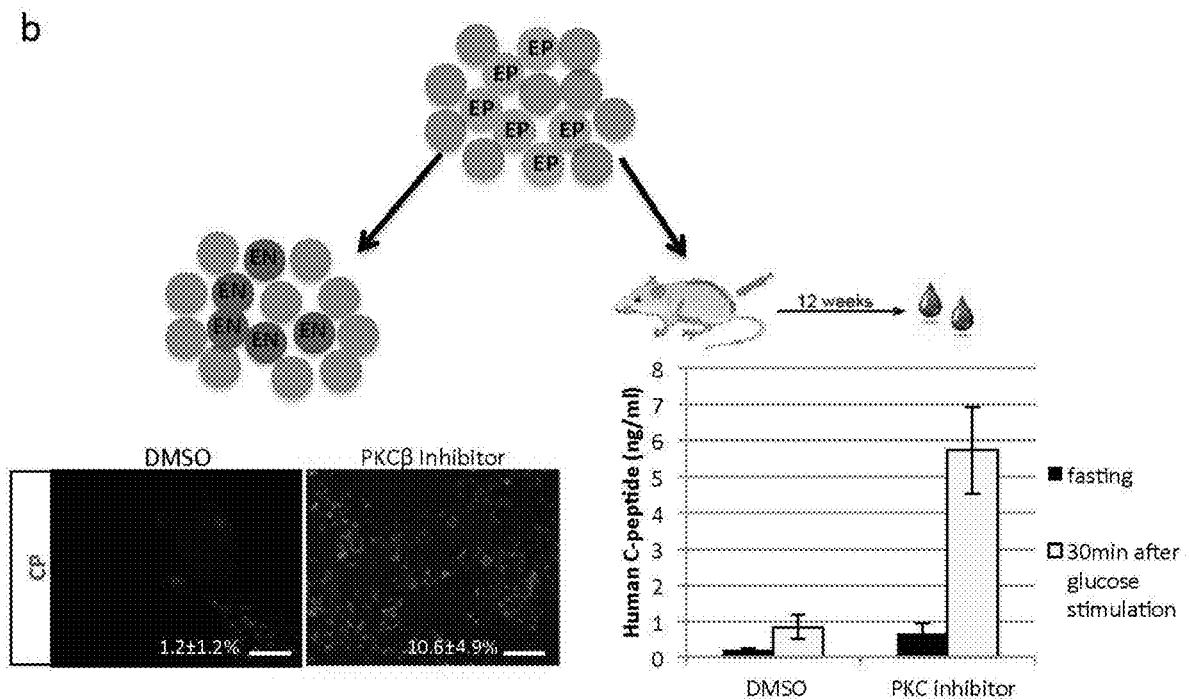

The inventors next investigated the developmental potential of cell populations enriched for NGN3+ cells that were induced by PKC inhibition. Endocrine progenitors generated after a 6 day treatment with PKCβ inhibitor were further differentiated in vitro for an additional 6 days in spontaneous differentiation medium (DMEM+B27 medium without additional chemical or growth factors). More c-peptide (a byproduct of insulin biosynthesis)-expressing cells were detected in the derivatives of PKCβ inhibitor treated cells (12.5 5.8%) than the derivatives of control cells (DMSO-treated, 1.2 1.2%; FIG. 2b). Next, the developmental competence of NGN3 progenitors was assessed using an in vivo transplantation assay[12,16]. Control or PKCβ inhibitor-treated cells were transplanted under the kidney capsule of SCID-beige mice. Following a 12-week incubation period, the cells were assayed for insulin secretion a glucose-stimulated c-peptide assay. Human c-peptide levels in the serum were significantly higher upon glucose injection than during fasting, indicating that PKCβ inhibitor treated endocrine progenitor stage cells are capable of giving rise to mature β-like cells in vivo (FIG. 2B).

Figures 3A, 3B, 3C, 3D:
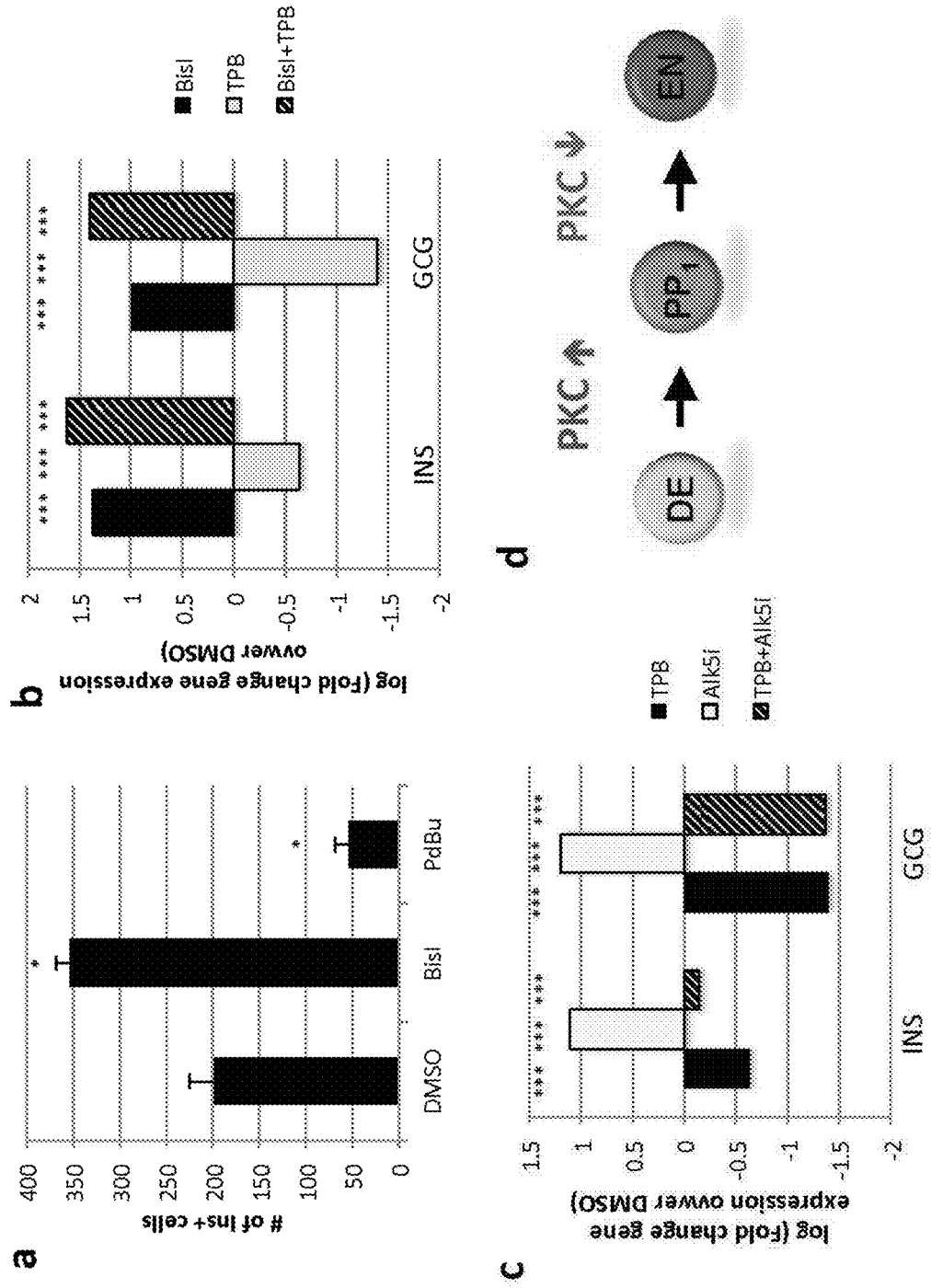
FIGS. 3A-3D show PKC agonists block the formation of insulin-expressing cells.

Given that PKC antagonists can induce endocrine progenitors the converse treatment, namely PKC activation, should block endocrine induction. Indeed, PKC activation with phorbol 12,13-dibutyrate (PdBu) caused a dramatic and robust (3.7-fold) decline in endocrine differentiation as measured by the number of insulin+ cells after a three-day treatment of H1-derived pancreatic progenitors (see Methods Protocol 2) (FIG. 3A), To confirm this result a different PKC agonist, (2S,5S)-(E,E)-8-(5-(4-(trifluoromethyl)phenyl)-2,4-pentadienoylamino)benzolactam (TPB) was shown by qRT-PCR to decrease the expression of endocrine hormones insulin and glucagon. The effect of TPB was reversed in the presence of BisI indicating that both TPB and Bis1 act specifically through PKC activation or inhibition (FIG. 3B). Recently Rezania et al. using a different directed differentiation protocol reported that a strong PKC activation decreased NGN3 and NEUROD1 expression, confirming robustness of our findings[18]. Several groups have reported that TGF inhibition is sufficient to increase the numbers of pancreatic endocrine cells[1,10,11]. Herein, the inventors demonstrated that PKC agonists were sufficient to block endocrine induction in the presence of TGF inhibitors, suggesting that PKC inactivation is required for endocrine induction by TGF inhibition (FIG. 3C).

In sum, the inventors have demonstrated herein the application of high-content chemical screening for investigating pathways capable of directing the differentiation of hESCs toward the pancreatic lineage. The inventors have performed two high-content chemical screens and identified PKC antagonists that enhanced differentiation of hESC-derived pancreatic progenitors toward the endocrine lineage. Conversely, PKC agonists blocked differentiation towards insulin-producing cells even in the presence of TGFβ inhibitors. Previously, the inventors have reported that (−)-Indolactam V, a PKC activator, promotes the generation of pancreatic progenitors[13] (see US Patent Application US2011/0070645, incorporated herein in its entirety by reference). Together with our current findings, the inventors have demonstrated that PKC plays a dynamic role in human pancreatic development: PKC signaling promotes the generation of pancreatic progenitors, while PKC inhibition in necessary for the subsequent differentiation towards pancreatic endocrine cells (FIG. 3D).

Unbiased chemical screens are a useful approach to identify novel pathways and reagents to control stem cells differentiation. The compounds identified by the inventors herein can be used in methods to establish an efficient strategy to differentiate hESCs/iPSCs into functional β cells.

TABLE 1

| Small molecule screening data - Screen 1 | | |
|---|---|---|
| Catagory | Paremeter | Description |
| Assay | Type of assay | In vitro, cell based |
| | Target | Human NGN3 |
| | Primary measurement | Detection by immunofluorescence of cell number |
| | Key reagents | sheep anti-NGN3 (1:100, RnD systems, AF3444) |
| | Assay Protocol | The HUES 8- pancreatic progenitor population was generated and plated onto 96-well plates. After overnight incubation, the compounds were added at final concentrations of 10 μM, and 1 μM. Six days later, the cells were stained with NGN3 antibody and the plates were analyzed with the Cellomics high content screening system (Thermo Scientific). |
| Library | Libarary Size | 2000 |
| | Library composition | 2000 chemicals, including signaling pathway regulators, kinase inhibitors, natural products, and FDA approved drugs |
| | Source | The library includes compounds from Sigma LOPAC (http://www.sigmaaldrich.com/chemistry/drug-discovery/validation-libraries/lopac1280-navigator.html/)and an in-house library. |
| Screen | Format | Four 96 well plates |
| | Concentration(s) tested | 10 μM, 1 μM; 0.1%, 0.01% DMSO |

TABLE 1-continued

Small molecule screening data - Screen 1

| Catagory | Paremeter | Description |
|---|---|---|
| | Plate controls | DMSO |
| | Reagent/compound dispensing system | Manual pin transfer |
| | Detection instrument and software | Cellomics high content imaging reader (ThermoScientific). |
| | Assay validation/QC Correction factors | Standard Deviation of Controls |
| | Normalization | Fold change compared to DMSO |
| Post-HTS analysis | Hit Criteria | >3 fold higher number of NGN3+ cells per area |
| | Hit rate | 2/2016 |
| | Additional assay(s) | Retesting of initial hits, dose response |
| | Confirmation of hit purity and structure | Compounds were repurchased (Callbiochem) |

TABLE 2

Small molecule screening data - Screen 2

| Catagory | Paremeter | Description |
|---|---|---|
| Assay | Type of assay | In vitro, cell based |
| | Target | Human C-peptide |
| | Primary measurement | Detection by immunofluorescence of cell number |
| | Key reagents | rabbit anti-c-peptide (1:1000, BCBC) |
| | Assay Protocol | The compound libraries used for this study:. For the chemical screen the day 8 cells were dispersed into single cells, using TrypLE, and replated at 150,000 cells/well of a 96 well plate in the presence of stage 3 media and 10 µM Y27632. Compounds were added to the wells on day 10 in stage 4 media, then again on days 12 and 14 in stage 5 media. Media was changed every other day suing the treatment. Cells were fixed using 4% paraformaldehyde (PFA, Sigma) on day 15 and stained using mouse antiglucagon and rabbit anti-c-peptide antibodies. |
| Library | Libarary Size | 418 |
| | Library composition | 418 compounds, including bioactive molecules, natural products and compounds that are known modulators of development or signaling pathways |
| | Source | In-house |
| Screen | Format | Four 96 well plates |
| | Concentration(s) tested | 10 µM, 0.1% DMSO |
| | Plate controls | DMSO |
| | Reagent/compound dispensing system | Manual pin transfer |
| | Detection instrument and software | Cellomics high content imaging reader (Thermo Scientific). |
| | Assay validation/QC Correction factors | Standard Deviation of Controls |
| | Normalization | Fold Change compared to DMSO |
| Post-HTS analysis | Hit Criteria | >3 fold higher number of insulin+ cells per area |
| | Hit rate | 6/418 |
| | Additional assay(s) | Retesting of initial hits, dose response |
| | Confirmation of hit purity and structure | Compounds were repurchased (Callbiochem) |

REFERENCES

All references cited herein are incorporated herein by reference in their entirety as if each individual publication or patent or patent application was specifically and individually indicated to be incorporated by reference in its entirety, 1 Nostro, M. C. et al. Stage-specific signaling through TGFbeta family members and WNT regulates patterning and pancreatic specification of human pluripotent stem cells. *Development* 138, 861-871, doi:10.1242/dev.055236 (2011).
2 D'Amour, K. A. et al. Efficient differentiation of human embryonic stem cells to definitive endoderm. *Nat Biotechnol* 23, 1534-1541, doi:10.1038/nbt1163 (2005).
3 D'Amour, K. A. et al. Production of pancreatic hormone-expressing endocrine cells from human embryonic stem cells. *Nat Biotechnol* 24, 1392-1401, doi:10.1038/nbt1259 (2006).
4 Kroon, E. et al. Pancreatic endoderm derived from human embryonic stem cells generates glucose-responsive insulin-secreting cells in vivo. *Nat Biotechnol* 26, 443-452, doi:10.1038/nbt1393 (2008).
5 Wells, J. & Melton, D. Vertebrate endoderm development. *Annual review of cell and developmental biology* 15, 393-803, doi:10.1146/annurev.cellbio.15.1.393 (1999).
6 Jiang, J. et al. Generation of insulin-producing islet-like clusters from human embryonic stem cells. *Stem Cells* 25, 1940-1953, doi:10.1634/stemcells.2006-0761 (2007).
7 Jiang, W. et al. In vitro derivation of functional insulin-producing cells from human embryonic stem cells. *Cell research* 17, 333-344, doi:10.1038/cr.2007.28 (2007).
8 Tateishi, K. et al. Generation of insulin-secreting islet-like clusters from human skin fibroblasts. *J Biol Chem* 283, 31601-31607, doi:10.1074/jbc.M806597200 (2008).
9 Zhang, D. et al. Highly efficient differentiation of human ES cells and iPS cells into mature pancreatic insulin-producing cells. *Cell research* 19, 429-438, doi:10.1038/cr.2009.28 (2009).
10 Rezania, A. et al. Production of functional glucagon-secreting α-cells from human embryonic stem cells. *Diabetes* 60, 239-247, doi:10.2337/db10-0573 (2011).
11 Kunisada, Y., Tsubooka-Yamazoe, N., Shoji, M. & Hosoya, M. Small molecules induce efficient differentiation into insulin-producing cells from human induced pluripotent stem cells. *Stem cell research* 8, 274-284, doi:10.1016/j.scr.2011.10.002 (2012).
12 Borowiak, M. et al. Small molecules efficiently direct endodermal differentiation of mouse and human embryonic stem cells. *Cell stem cell* 4, 348-358, doi:10.1016/j.stem.2009.01.014 (2009).
13 Chen, S. et al. A small molecule that directs differentiation of human ESCs into the pancreatic lineage. *Nat Chem Biol* 5, 258-265, doi:10.1038/nchembio.154 (2009).
14 Gu, G., Dubauskaite, J. & Melton, D. A. Direct evidence for the pancreatic lineage: NGN3+ cells are islet progenitors and are distinct from duct progenitors. *Development* 129, 2447-2457 (2002).
15 Blum, B. et al. Functional beta-cell maturation is marked by an increased glucose threshold and by expression of urocortin 3. *Nature biotechnology* 30, 261-264, doi:10.1038/nbt.2141 (2012).
16 Kelly, O. G. et al. Cell-surface markers for the isolation of pancreatic cell types derived from human embryonic stem cells. *Nat Biotechnol* 29, 750-756, doi:10.1038/nbt.1931 (2011).
17 Maehr, R. et al. Generation of pluripotent stem cells from patients with type 1 diabetes. *Proceedings of the National Academy of Sciences of the United States of America* 106, 15768-15773, doi:10.1073/pnas.0906894106 (2009).
18 Rezania, A. et al. Maturation of Human Embryonic Stem Cell-Derived Pancreatic Progenitors into Functional Islets Capable of Treating Pre-existing Diabetes in Mice. *Diabetes*, doi:10.2337/db11-1711 (2012).

What is claimed is:

1. A method for producing a pancreatic β-cell from pdx+ pancreatic progenitor cell comprising contacting a population of Pdx+ pancreatic progenitor cells with at least one PKC inhibitor to induce the differentiation of at least one Pdx+ pancreatic progenitor cell into a pancreatic β-cell expressing insulin.

2. The method of claim 1, wherein the inhibitor is an inhibitor of PKCβ.

3. The method of claim 1, wherein the inhibitor is a compound with the following structure or a derivative, analogue or variant of the compound:

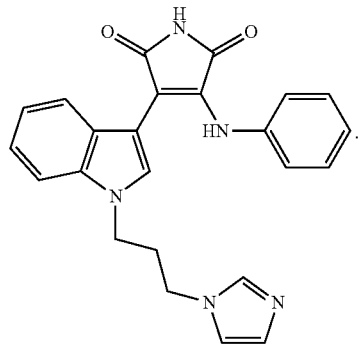 [SMILES: O=C1NC(=O)C(c2cn(CCCn3ccnc3)c3ccccc23)=C1Nc1ccccc1]

4. The method of claim 1, wherein the inhibitor is a GSK-2 compound with the following structure or a derivative, analogue or variant of the compound:

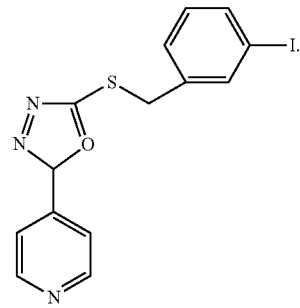

5. The method of claim 1, wherein the inhibitor of PKC is a bisindolylmaleimide.

6. The method of claim 5, wherein a bisindolylmaleimide is selected from the group consisting of: bisindolylmaleimide I, bisindolylmaleimide II, bisindolylmaleimide III, hydrochloride, or a derivative, analogue or variant.

7. The method of claim 5, wherein the derivative or variant or analogue thereof is selected from a derivative or variant of analogue of a compound selected from:

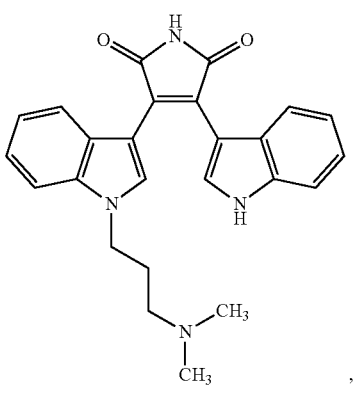

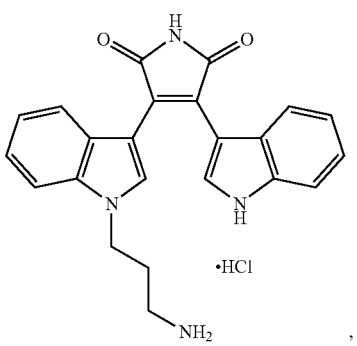

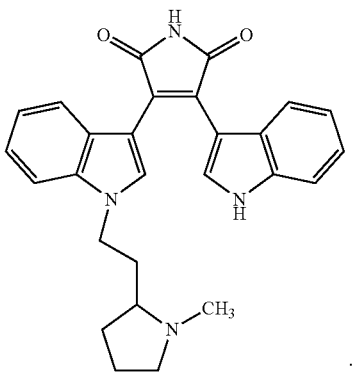

8. The method of claim 1, wherein the inhibitor is a pseudohypericin, or a derivative, analogue or variant of the compound:

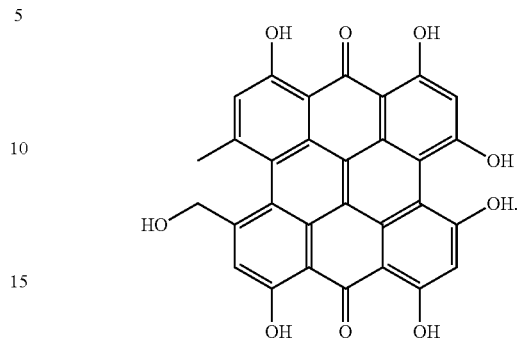

9. The method of claim 1, wherein the PKC inhibitor is indorublin-3-monoxime, 5-Indo or a derivative, analogue or variant of the following compound:

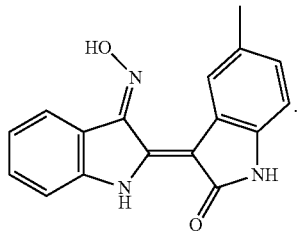 [SMILES: Cc1ccc2c(c1)/C(=C1/Nc3ccccc3/C1=N\O)C(=O)N2]

10. The method of claim 1, wherein at least 20% of the Pdx+ pancreatic progenitor cells in the population are induced to differentiate into pancreatic beta cells.

11. The method of claim 1, wherein at least 40% of the Pdx+ pancreatic progenitor cells in the population are induced to differentiate into pancreatic beta cells.

12. The method of claim 1, wherein between 80-90% of the Pdx+ pancreatic progenitor cells in the population are induced to differentiate into pancreatic beta cells.

13. The method of claim 1, further comprising exposing the Pdx+ pancreatic progenitor cell population to at least one additional agent.

14. The method of claim 1, wherein the pancreatic β-cells have at least one characteristic of endogenous pancreatic β cells or differentiate into a cell with at least one characteristic of endogenous pancreatic β cells.

15. The method of claim 14, wherein the at least one characteristic of an endogenous pancreatic β-cell is secretion of insulin in response to glucose.

* * * * *

UNITED STATES PATENT AND TRADEMARK OFFICE
CERTIFICATE OF CORRECTION

PATENT NO. : 10,941,384 B2
APPLICATION NO. : 14/777480
DATED : March 9, 2021
INVENTOR(S) : Douglas A. Melton et al.

Page 1 of 1

It is certified that error appears in the above-identified patent and that said Letters Patent is hereby corrected as shown below:

In the Claims

Column 76, Claim 9, Line 20, please delete "5-Indo" and insert --5-Iodo--

Signed and Sealed this
Third Day of August, 2021

Drew Hirshfeld
*Performing the Functions and Duties of the
Under Secretary of Commerce for Intellectual Property and
Director of the United States Patent and Trademark Office*